US008835500B2

(12) United States Patent
Laurin et al.

(10) Patent No.: US 8,835,500 B2
(45) Date of Patent: Sep. 16, 2014

(54) PHARMACEUTICAL FORMULATIONS OF AMYLOID INHIBITING COMPOUNDS

(75) Inventors: Julie Laurin, St-Lazare (CA); Denis Garceau, Kirkland (CA)

(73) Assignee: BHI Limited Partership, Laval (CA)

( * ) Notice: Subject to any disclaimer, the term of this patent is extended or adjusted under 35 U.S.C. 154(b) by 526 days.

(21) Appl. No.: 12/362,971

(22) Filed: Jan. 30, 2009

(65) Prior Publication Data

US 2009/0182056 A1 Jul. 16, 2009

Related U.S. Application Data

(63) Continuation of application No. 11/103,656, filed on Apr. 12, 2005, now abandoned, which is a continuation-in-part of application No. 10/871,549, filed on Jun. 18, 2004, now abandoned, and a continuation-in-part of application No. PCT/IB2004/002381, filed on Jun. 21, 2004.

(60) Provisional application No. 60/480,984, filed on Jun. 23, 2003, provisional application No. 60/512,116, filed on Oct. 17, 2003, provisional application No. 60/640,108, filed on Dec. 29, 2004.

(51) Int. Cl.
*A61K 31/185* (2006.01)
*A61K 9/28* (2006.01)
*A61K 9/20* (2006.01)

(52) U.S. Cl.
CPC ............. *A61K 9/2886* (2013.01); *A61K 9/2054* (2013.01); *A61K 9/20* (2013.01); *A61K 9/2846* (2013.01); *A61K 31/185* (2013.01); *Y10S 514/974* (2013.01)
USPC .......................................... 514/578; 514/974

(58) Field of Classification Search
None
See application file for complete search history.

(56) References Cited

U.S. PATENT DOCUMENTS

| | | | |
|---|---|---|---|
| 3,658,966 A | 4/1972 | Tsunoo | |
| 3,920,833 A | 11/1975 | Cook | |
| 4,255,448 A | 3/1981 | Fariello | |
| 4,657,704 A | 4/1987 | Yamamoto | |
| 5,614,220 A | 3/1997 | Fukui et al. | |
| 5,643,562 A | 7/1997 | Kisilevsky et al. | |
| 5,683,718 A * | 11/1997 | Errigo | |
| 5,728,375 A | 3/1998 | Kisilevsky et al. | |
| 5,840,294 A | 11/1998 | Kisilevsky et al. | |
| 5,972,328 A | 10/1999 | Kisilevsky et al. | |
| 6,015,835 A | 1/2000 | Miyamoto | |
| 6,030,341 A | 2/2000 | Skates et al. | |
| 6,310,073 B1 | 10/2001 | Kisilevsky et al. | |
| 6,316,501 B1 | 11/2001 | Miyamoto | |
| 6,368,629 B1 | 4/2002 | Watanabe et al. | |
| 6,376,557 B1 | 4/2002 | Zaveri | |
| 6,670,399 B2 | 12/2003 | Green et al. | |
| 7,253,306 B2 | 8/2007 | Kong et al. | |
| 2002/0022657 A1 | 2/2002 | Gervais et al. | |
| 2004/0220138 A1 | 11/2004 | Gervais et al. | |
| 2005/0031651 A1 | 2/2005 | Gervais et al. | |
| 2005/0031654 A1 | 2/2005 | Eymard | |
| 2005/0038000 A1 | 2/2005 | Kong et al. | |
| 2005/0038117 A1 | 2/2005 | Kong et al. | |
| 2005/0085553 A1 | 4/2005 | Miyamato | |
| 2005/0096385 A1 | 5/2005 | Kong et al. | |
| 2005/0143462 A1 | 6/2005 | Kong et al. | |
| 2005/0215562 A1 | 9/2005 | Tremblay et al. | |
| 2006/0079578 A1 | 4/2006 | Laurin et al. | |

FOREIGN PATENT DOCUMENTS

| | | |
|---|---|---|
| EP | 0533352 | 3/1993 |
| EP | 0797992 | 10/1997 |
| EP | 1473032 | 11/2004 |
| WO | WO 93-03714 | 3/1993 |
| WO | WO 94/22437 | 10/1994 |
| WO | WO 96/28187 | 9/1996 |
| WO | WO 99-40909 | 8/1999 |
| WO | WO 99/59571 | 11/1999 |
| WO | WO 01/85093 | 11/2001 |
| WO | WO 2004/058239 | 7/2004 |
| WO | WO 2004/112762 A2 | 12/2004 |
| WO | WO 2009/019534 A2 | 2/2009 |

OTHER PUBLICATIONS

The Merck Manual ("Amyloidosis", Merck Manual online, Apr. 2008, downloaded from "http://www.merck.com/mmhe/print/sec25/ch304/ch304a.html" on Jan. 16, 2009, pp. 1-3 of 3.*
Mehran, et al.: "Pharmacological Activity of Alzhemed in Mild-to-Moderate Alzheimer's Disease (AD) Patients" Announcement on Apr. 14, 2004 of Results From Phase II Extension Study.
Tonini, et al.: "An In Vitro Study of the Relationship Between GABA Receptor Function and Propulsive Motility in the Distal Colon of the Rabbit", Br J Pharmacol. Dec. 1989; 98(4):1109-18.
Maggi, et al.: "GABA A Receptor Medicated Neurogenic Inhibition of Motility in the Small Intestine of Urethane-Anaesthetized Rats" Gen Pharmacol. 1986; 17(2):167-71.
Ishizawa: "Effects of GABA and Homotaurine on the Colonic Motility of the Guinea Pig" Nippon Heikatsukin Gakkai Zasshi. Dec. 1987; 23(6):441-7.
Kimura, et al.: "Taurine" (Sulfur-Containing Amino Acids) 1979 pp. 179-186.
Ong: "Uptake Inhibitors Potentiate y-Aminobutyric Acid-Induced Contractile Responses in the Isolated Ileum of the Guinea-Pig" Br. J. Pharmac. (1987), 91, pp. 9-15.
Kimura, et al.: "Effect of Taurine on Drug Adsorption From the Rat Gastrointestinal Tract" J. Pharm. Dyn. (1981) 4, pp. 35-41.

(Continued)

*Primary Examiner* — Savitha Rao
*Assistant Examiner* — Gregg Polansky
(74) *Attorney, Agent, or Firm* — McCarter & English, LLP; Danielle L. Herritt; Emily Dertz

(57) ABSTRACT

Therapeutic formulations and methods for inhibiting amyloid deposition in a subject, whatever its clinical setting, are described. Therapeutic formulations and methods for preventing or treating amyloidosis and/or amyloid-related disease are also described.

18 Claims, 4 Drawing Sheets

(56) References Cited

OTHER PUBLICATIONS

Krantis, et al.: "Rat Gastroduodenal Motility In Vivo: Interaction of GABA and VIP in Control of Spontaneous Relaxations" Am J Physiol Gastrointest Liver Physiol 275: 1998: vol. 275, Issue 5, G897-G903.

Dietmaier, et al.: "Acamprosate" Micromedex, Inc., Publication Jun. 1996.

Munzar, et al.: "Clinical Study of a Urinary Competitive ELISA for Neural Thread Protein in Alzheimer Disease" Neurology and Clinical Neurophysiology, vol. 2002, No. 1; pp. 1-8.

Kodama et al., "Gastric Mucosal Damage Caused by Monochloramine in the Rat and Protective Effect of Taurine: Endoscopic Observation Through Gastric Fistula," Endoscopy, 2000, 294-299, 32, Georg Thieme, Verlag Suttgart—New York.

"Amyloidosis," Special Subjects: Merck Manual Home Edition, , 2007, http://www.merck.com/mmhe/sec25/ch304ch304a.htm#sec25-ch304-ch304a-281.

Burggren, et al.: "Structural and Functional Neuroimaging in Alzheimer's Disease: An Update" Neurochem Inc. Medicinal Chemistry 2002, No. 2, pp. 385-393.

Sair, et al.: "In Vivo Amyloid Imaging in Alzheimer's Disease" Neuroradiology (2004) 46: pp. 93-104.

The Merck Manual, 17$^{th}$ Edition (1999), pp. 1293-1294 and 1337-1338.

Kisilevsky et al., "Arresting Amyloidosis In Vivo Using Small-Molecule Anionic Sulphonates or Sulphates: Implications for Alzheimer's Disease," Nature Medicine, Feb. 1995, 143-148, vol. 1, No. 2, Canada.

Amyloidosis, 2 pages. Merck Manual Online, http://www.merck.com.mmhesec25/ch304ch304a.html#sec25-ch304a-218. 2007.

Fraser, P.E. et al: Arresting Amyloidosis In Vivo Using Small-Molecule Anionic Sulphonates or Sulphates: Implications for Alzheimer's Disease; Nat Med; 1995; 1: 143-8.

Robinson M.J.: "Coating of Pharmaceutical Dosage Forms"; In: Osol A, Ed. Remington's Pharmaceutical Sciences; Easton, PA; Mach Publishing Company, 1980; 1585-93.

'Herpesvirus Infections': In: Beers MH, Berkow R, Eds. The Merck Manual of Diagnosis and Therapy. Whitehouse Station, NJ: Merck Research Laboratories, 1999: 1293-338.

U.S. Appl. No. 10/871,549, Office Action dated Sep. 25, 2008, 18 pages.

Fariello, et al., "Homotaurine: A GABA agonist with anticonvulsant effects," Brain Res. Bull., 1980, 5 (Suppl. 2), pp. 691-699.

Fariello, et al., "Homotaurine (3-aminopropanesulfonic acid; 3APS) protects from the convulsant and cytotoxic effect of systematically administered kainic acid," Neurology (NY), 1982, 32, 241-245.

English language Abstract of Rumpf, P., "Preparation d'acides aminoalcoylsulfoniques en vue d'une etude physicochimique comparative," Bull. Soc. Chim. Fr., 1938, 5, pp. 871-888, (with full article).

Sen, N.P., "Synthesis and properties of homotaurine," Can. J. Chem., 1962, 40, 2189-91.

* cited by examiner

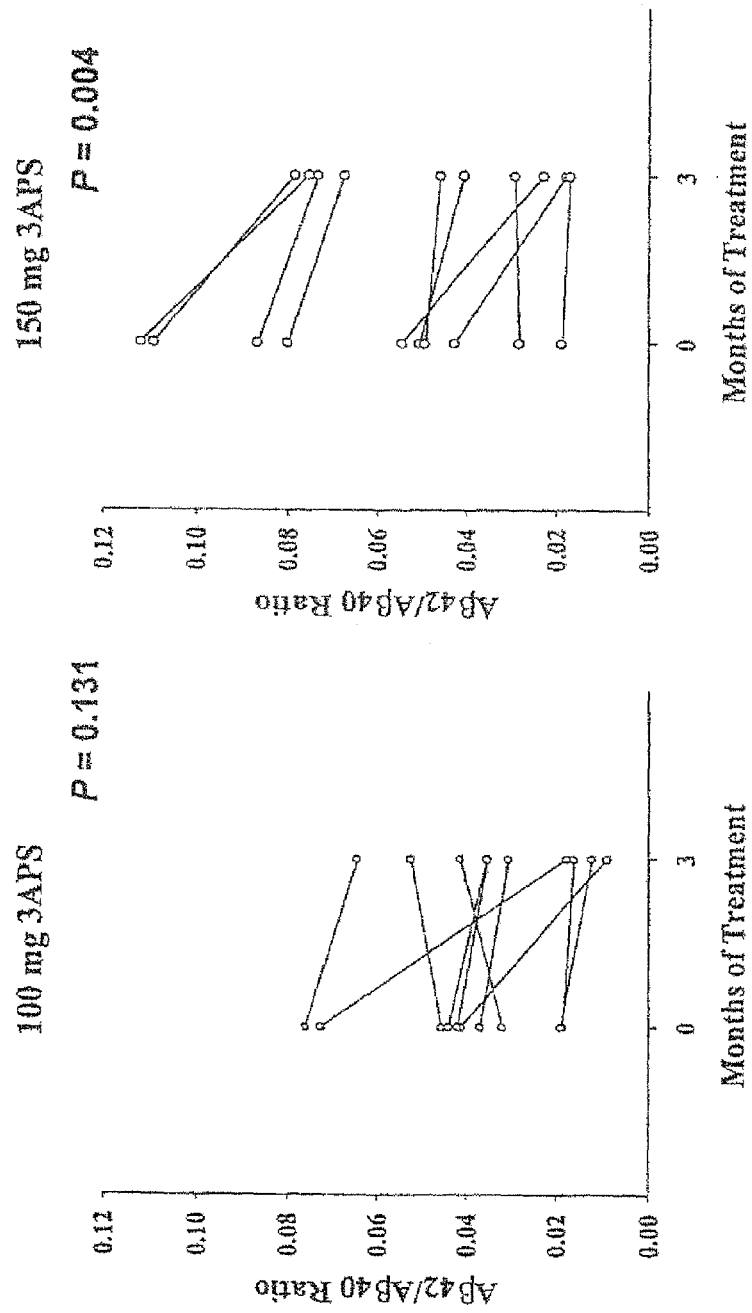

PHARMACEUTICAL FORMULATIONS OF AMYLOID INHIBITING COMPOUNDS

This application is a continuation of U.S. patent application Ser. No. 11/103,656, filed Apr. 12, 2005 now abandoned, which is a continuation-in-part of U.S. patent application Ser. No. 10/871,549, filed Jun. 18, 2004 now abandoned, and a continuation-in-part of PCT application No. PCT/IB2004/002381, filed Jun. 21, 2004, and claims priority of U.S. provisional Patent Application No. 60/480,984, filed Jun. 23, 2003, U.S. Provisional Patent Application No. 60/512,116, filed Oct. 17, 2003, and U.S. Provisional Patent Application No. 60/640,108, filed Dec. 29, 2004.

RELATED APPLICATIONS

This application is related to U.S. provisional application no. 60/436,379, filed Dec. 24, 2002, entitled Combination Therapy for the Treatment of Alzheimer's Disease, U.S. provisional application 60/482,214, filed Jun. 23, 2003, U.S. utility patent application Ser. No. 10/746,138, filed Dec. 24, 2003, and International patent application no. PCT/CA2003/002011, entitled Therapeutic Formulations for the Treatment of Beta-Amyloid Related Diseases. This application is related to U.S. provisional patent application No. 60/482,058, filed Jun. 23, 2003, U.S. provisional patent application No. 60/512,135, filed Oct. 17, 2003, both entitled Synthetic Process for Preparing Compounds for Treating Amyloidosis, and U.S. application Ser. No. 10/871,543, filed Jun. 18, 2004, entitled Improved Pharmaceutical Drug Candidates and Method for Preparation Thereof. This application is also related to U.S. provisional patent application No. 60/480,918, filed Jun. 23, 2003, identified by U.S. provisional application 60/512,017, filed Oct. 17, 2003, U.S. patent application Ser. No. 10/871,613, filed Jun. 18, 2004, entitled Methods for Treating Protein Aggregation Disorders. This application is also related to U.S. provisional patent application No. 60/480,906, filed Jun. 23, 2003, identified by U.S. provisional patent application No. 60/512,047, filed Oct. 17, 2003, U.S. application Ser. No. 10/871,514, filed Jun. 18, 2004, and U.S. application Ser. No. 10/871,365, filed Jun. 18, 2004, all entitled Methods and Compositions for Treating Amyloid-Related Diseases; and U.S. provisional patent application No. 60/480,928, also filed 23 Jun. 2003, U.S. provisional patent application No. 60/512,018, filed Oct. 17, 2003, and U.S. application Ser. No. 10/871,512, filed Jun. 18, 2004, all entitled Methods and Compositions for the Treatment of Amyloid- and Epileptogenesis-Associated Diseases; This application is also related to Method for Treating Amyloidosis, U.S. patent application Ser. No. 08/463,548, now U.S. Pat. No. 5,972,328. This application is also related to Pharmaceutical Formulations of Amyloid Inhibiting Compounds, U.S. provisional patent application No. 60/640,108, filed Dec. 29, 2004.

The entire contents of each of the foregoing patent applications and patents are expressly incorporated by reference in their entirety including, without limitation, the specification, claims, and abstract, as well as any figures, tables, or drawings thereof.

BACKGROUND OF THE INVENTION

Amyloidosis refers to a pathological condition characterized by the presence of amyloid fibrils. Amyloid is a generic term referring to a group of diverse but specific protein deposits (intracellular or extracellular) which are seen in a number of different diseases. Though diverse in their occurrence, all amyloid deposits have common morphologic properties, stain with specific dyes (e.g., Congo red), and have a characteristic red-green birefringent appearance in polarized light after staining. They also share common ultrastructural features and common X-ray diffraction and infrared spectra.

Amyloid-related diseases can either be restricted to one organ or spread to several organs. The first instance is referred to as "localized amyloidosis" while the second is referred to as "systemic amyloidosis."

Some amyloid diseases can be idiopathic, but most of these diseases appear as a complication of a previously existing disorder. For example, primary amyloidosis (AL amyloid) can appear without any other pathology or can follow plasma cell dyscrasia or multiple myeloma.

Secondary amyloidosis is usually seen associated with chronic infection (such as tuberculosis) or chronic inflammation (such as rheumatoid arthritis). A familial form of secondary amyloidosis is also seen in other types of familial amyloidosis, e.g., Familial Mediterranean Fever (FMF). This familial type of amyloidosis is genetically inherited and is found in specific population groups. In both primary and secondary amyloidosis, deposits are found in several organs and are thus considered systemic amyloid diseases.

"Localized amyloidoses" are those that tend to involve a single organ system. Different amyloids are also characterized by the type of protein present in the deposit. For example, neurodegenerative diseases such as scrapie, bovine spongiform encephalitis, Creutzfeldt-Jakob disease, and the like are characterized by the appearance and accumulation of a protease-resistant form of a prion protein (referred to as AScr or PrP-27) in the central nervous system. Similarly, Alzheimer's disease, another neurodegenerative disorder, is characterized by neuritic plaques and neurofibrillary tangles. In this case, the amyloid plaques found in the parenchyma and the blood vessel are formed by the deposition of fibrillar Aβ amyloid protein. Other diseases such as adult-onset diabetes (type II diabetes) are characterized by the localized accumulation of amyloid fibrils in the pancreas.

Once these amyloids have formed, there is no known, widely accepted therapy or treatment which significantly dissolves amyloid deposits in situ, prevents further amyloid deposition or prevents the initiation of amyloid deposition.

Each amyloidogenic protein has the ability to undergo a conformational change and to organize into β-sheets and form insoluble fibrils which may be deposited extracellularly or intracellularly. Each amyloidogenic protein, although different in amino acid sequence, has the same property of forming fibrils and binding to other elements such as proteoglycan, amyloid P and complement component. Moreover, each amyloidogenic protein has amino acid sequences which, although different, show similarities such as regions with the ability to bind to the glycosaminoglycan (GAG) portion of proteoglycan (referred to as the GAG binding site) as well as other regions which promote β-sheet formation, Proteoglycans are macromolecules of various sizes and structures that are distributed almost everywhere in the body. They can be found in the intracellular compartment, on the surface of cells, and as part of the extracellular matrix. The basic structure of all proteoglycans is comprised of a core protein and at least one, but frequently more, polysaccharide chains (GAGs) attached to the core protein. Many different GAGs have been discovered including chondroitin sulfate, dermatan sulfate, keratan sulfate, heparin, and hyaluronan.

In specific cases, amyloid fibrils, once deposited, can become toxic to the surrounding cells. For example, the Aβ fibrils organized as senile plaques have been shown to be associated with dead neuronal cells, dystrophic neurites, astrocytosis, and microgliosis in patients with Alzheimer's disease. When tested in vitro, oligomeric (soluble) as well as fibrillar Aβ peptide was shown to be capable of triggering an activation process of microglia (brain macrophages), which would explain the presence of microgliosis and brain inflammation found in the brain of patients with Alzheimer's disease. Both oligomeric and fibrillar Aβ peptide can also induce neuronal cell death in vitro. See, e.g., M P Lambert, et al., Proc. Natl. Acad. Sci. USA 95, 6448-53 (1998).

In another type of amyloidosis seen in patients with type II diabetes, the amyloidogenic protein IAPP, when organized in oligomeric forms or in fibrils, has been shown to induce β-islet cell toxicity in vitro. Hence, appearance of IAPP fibrils in the pancreas of type II diabetic patients contributes to the loss of the β islet cells (Langerhans) and organ dysfunction which can lead to insulinemia.

Another type of amyloidosis is related to $\beta_2$ microglobulin and is found in long-term hemodialysis patients. Patients undergoing long term hemodialysis will develop $\beta_2$-microglobulin fibrils in the carpal tunnel and in the collagen rich tissues in several joints. This causes severe pain, joint stiffness and swelling.

Amyloidosis is also characteristic of Alzheimer's disease. Alzheimer's disease is a devastating disease of the brain that results in progressive memory loss leading to dementia, physical disability, and death over a relatively long period of time. With the aging populations in developed countries, the number of Alzheimer's patients is reaching epidemic proportions.

People suffering from Alzheimer's disease develop a progressive dementia in adulthood, accompanied by three main structural changes in the brain: diffuse loss of neurons in multiple parts of the brain; accumulation of intracellular protein deposits termed neurofibrillary tangles; and accumulation of extracellular protein deposits termed amyloid or senile plaques, surrounded by misshapen nerve terminals (dystrophic neurites) and activated microglia (microgliosis and astrocytosis). A main constituent of these amyloid plaques is the amyloid-β peptide (Aβ), a 39-43 amino-acid protein that is produced through cleavage of the β-amyloid precursor protein (APP). Extensive research has been conducted on the relevance of Aβ deposits in Alzheimer's disease, see, e.g., Selkoe, Trends in Cell Biology 8, 447-453 (1998). Aβ naturally arises from the metabolic processing of the amyloid precursor protein ("APP") in the endoplasmic reticulum ("ER"), the Golgi apparatus, or the endosomal-lysosomal pathway, and most is normally secreted as a 40 ("Aβ1-40") or 42 ("Aβ1-42") amino acid peptide (Selkoe, Annu. Rev. Cell Biol. 10, 373-403 (1994)). A role for Aβ as a primary cause for Alzheimer's disease is supported by the presence of extracellular Aβ deposits in senile plaques of Alzheimer's disease, the increased production of Aβ in cells harboring mutant Alzheimer's disease associated genes, e.g., amyloid precursor protein, presenilin I and presenilin II; and the toxicity of extracellular soluble (oligomeric) or fibrillar Aβ to cells in culture. See, e.g., Gervais, Eur. Biopharm. Review, 40-42 (Autumn 2001); May, DDT 6, 459-62 (2001). Although symptomatic treatments exist for Alzheimer's disease, this disease cannot be prevented or cured at this time.

Alzheimer's disease is characterized by diffuse and neuritic plaques, cerebral angiopathy, and neurofibrillary tangles. Plaque and blood vessel amyloid is believed to be formed by the deposition of insoluble Aβ amyloid protein, which may be described as diffuse or fibrillary. Both soluble oligomeric Aβ and fibrillar Aβ are also believed to be neurotoxic and inflammatory.

Another type of amyloidosis is cerebral amyloid angiopathy (CAA). CAA is the specific deposition of amyloid β fibrils in the walls of leptomingeal and cortical arteries, arterioles and veins. It is commonly associated with Alzheimer's disease, Down's syndrome and normal aging, as well as with a variety of familial conditions related to stroke or dementia (see Frangione et al., Amyloid: J. Protein Folding Disord. 8, Suppl. 1, 36-42 (2001)).

Presently available therapies for treatment of β-amyloid diseases are almost entirely symptomatic, providing only temporary or partial clinical benefit. Although some pharmaceutical agents have been described that offer partial symptomatic relief, no comprehensive pharmacological therapy is currently available for the prevention or treatment of, for example, Alzheimer's disease.

SUMMARY OF THE INVENTION

This invention provides methods, compositions, and formulations that are useful in the treatment of amyloidosis. The methods of the invention involve administering to a subject a therapeutic composition or formulation that inhibits amyloid deposition. Accordingly, the compositions and methods of the invention are useful for inhibiting amyloidosis disorders in which amyloid deposition occurs. The methods of the invention may be used therapeutically to treat amyloidosis or may be used prophylactically in a subject susceptible to amyloidosis.

In one aspect, the methods of the present invention are based, at least in part, on inhibiting an interaction between an amyloidogenic protein and a constituent of a basement membrane to inhibit amyloid deposition. In particular embodiments, the constituent of the basement membrane is a glycoprotein or proteoglycan, preferably agrin, perlecan, or heparan sulfate proteoglycan. A therapeutic compound used in the method of the invention can interfere with binding of a basement membrane constituent to a target binding site on an amyloidogenic protein, thereby inhibiting amyloid deposition. In other embodiments, a therapeutic compound used in the method of the invention can enhance clearance of amyloid β from the brain, thereby inhibiting amyloid deposition. In other embodiments, a therapeutic compound used in the method of the invention can inhibit neurodegeneration or cellular toxicity induced by amyloid (e.g., by soluble or insoluble amyloid, e.g., fibrils, by amyloid deposition and/or by amyloid-β, as described herein).

In another aspect, the invention relates to the use of alkylsulfonic acids in the treatment of amyloid-related diseases.

Accordingly, in one aspect, the invention is directed to a method for inhibiting amyloid deposition in a subject comprising administering to the subject an effective amount of a therapeutic formulation comprising a therapeutic compound formulated to significantly reduce or prevent gastrointestinal intolerance, such that amyloid deposition is inhibited.

In another aspect, the invention pertains to a method of treating or preventing an amyloid-related disease, e.g., Aβ-related disease, in a subject, comprising administering to a subject a therapeutic amount of a therapeutic formulation comprising a therapeutic compound formulated to significantly reduce or prevent gastrointestinal intolerance, such that the amyloid-related disease is treated or prevented.

In an additional aspect, the invention is a method for inhibiting amyloid deposition in a subject comprising administering to the subject an effective amount of a therapeutic formulation comprising a therapeutic compound formulated to significantly reduce or prevent gastrointestinal intolerance, such that the therapeutic compound inhibits an interaction between an amyloidogenic protein and a constituent of a basement membrane to inhibit amyloid deposition.

Another aspect of the invention involves a method for inhibiting amyloid deposition in a subject comprising administering to the subject an effective amount of a therapeutic formulation comprising a therapeutic compound formulated to significantly reduce or prevent gastrointestinal intolerance, such that the therapeutic compound inhibits neurodegeneration or cellular toxicity induced by amyloid (e.g., by soluble or insoluble amyloid, e.g., fibrils, by amyloid deposition and/or by amyloid-β, as described herein).

In another aspect, the invention is directed to a method for inhibiting amyloid deposition in a subject comprising administering to the subject an effective amount of a therapeutic formulation comprising a therapeutic compound formulated to significantly reduce or prevent gastrointestinal intolerance, such that the therapeutic compound enhances clearance of amyloid β from the brain.

In yet another aspect, the invention pertains to a method for inhibiting amyloid deposition in a subject comprising orally administering to the subject an effective amount of a therapeutic formulation comprising a therapeutic compound formulated to significantly reduce or prevent gastrointestinal intolerance.

An additional aspect of the invention is a pharmaceutical composition for inhibiting amyloid deposition in a subject comprising a therapeutic formulation comprising a therapeutic compound formulated to significantly reduce or prevent gastrointestinal intolerance, in an amount sufficient to inhibit amyloid deposition in a subject, and a pharmaceutically acceptable vehicle.

In another aspect, the invention is directed to a pharmaceutical composition for treating amyloidosis comprising a therapeutic formulation comprising a therapeutic compound formulated to significantly reduce or prevent gastrointestinal intolerance, in an amount sufficient to treat amyloidosis in a subject, and a pharmaceutically acceptable vehicle.

In another aspect, the present invention pertains to a pharmaceutical composition for treating or preventing an amyloid-related disease, e.g., Aβ-related disease, comprising a therapeutic formulation comprising a therapeutic compound formulated to significantly reduce or prevent gastrointestinal intolerance, in an amount sufficient to prevent or treat an amyloid-related disease in a subject, and a pharmaceutically acceptable vehicle.

In yet another aspect, the invention pertains to a method for reducing amyloid deposits in a subject having amyloid deposits, the method comprising administering to the subject an effective amount of a therapeutic formulation comprising a therapeutic compound formulated to significantly reduce or prevent gastrointestinal intolerance, such that amyloid deposits are reduced in the subject.

Another aspect of the invention is directed to a method for inhibiting the binding of a chemokine to a glycosaminoglycan in a subject comprising administering to the subject a therapeutic formulation comprising a therapeutic compound formulated to significantly reduce or prevent gastrointestinal intolerance, such that the binding of a chemokine to a glycosaminoglycan is inhibited.

Yet another aspect of the invention is directed to a method for modulating interaction between a bacterium and a glycosaminoglycan in a human comprising administering to the human an effective amount of a therapeutic formulation comprising a therapeutic compound formulated to significantly reduce or prevent gastrointestinal intolerance.

In an additional aspect, the invention pertains to a method for treating a bacterial infection in a human comprising administering to the human an effective amount of a therapeutic formulation comprising a therapeutic compound formulated to significantly reduce or prevent gastrointestinal intolerance.

In another aspect, the invention is a method for modulating interaction between a virus and a glycosaminoglycan in a subject comprising administering to the subject an effective amount of a therapeutic formulation comprising a therapeutic compound formulated to significantly reduce or prevent gastrointestinal intolerance.

Another aspect of the invention is a method for treating a viral infection in a subject comprising administering to the subject a therapeutic formulation comprising an effective amount of a therapeutic formulation comprising a therapeutic compound formulated to significantly reduce or prevent gastrointestinal intolerance.

Yet another aspect of the invention is directed to a method of preventing, treating or inhibiting cerebral amyloid angiopathy in a subject, comprising administering an effective amount of a therapeutic formulation comprising a therapeutic compound formulated to significantly reduce or prevent gastrointestinal intolerance.

In an additional aspect, the invention pertains to a method of preventing, treating or inhibiting cerebral amyloid angiopathy, comprising contacting a blood vessel wall cell with a therapeutic formulation comprising a therapeutic compound formulated to significantly reduce or prevent gastrointestinal intolerance, such that cerebral amyloid angiopathy is prevented, treated, or inhibited.

In another aspect, the invention pertains to a method of preventing, treating or inhibiting cerebral amyloid angiopathy, comprising contacting a blood vessel wall cell with a therapeutic compound of a therapeutic formulation, formulated to significantly reduce or prevent gastrointestinal intolerance, such that cerebral amyloid angiopathy is prevented, treated, or inhibited.

An additional aspect of the present invention is directed to a method of preventing, treating or inhibiting Alzheimer's disease in a subject, comprising administering to the subject an effective amount of a therapeutic formulation comprising a therapeutic compound formulated to significantly reduce or prevent gastrointestinal intolerance.

An additional aspect of the present invention is directed to a method of preventing, treating or inhibiting Alzheimer's disease in a subject, comprising administering to the subject an effective amount of a therapeutic formulation comprising a therapeutic compound formulated to significantly reduce or prevent gastrointestinal intolerance, such that Alzheimer's disease is prevented, treated, or inhibited.

In another aspect, the invention is directed to a packaged pharmaceutical composition for inhibiting amyloid deposition in a subject, comprising a container holding a therapeutically effective amount of a therapeutic formulation comprising a therapeutic compound formulated to significantly reduce or prevent gastrointestinal intolerance; and instructions for using the compound for inhibiting amyloid deposition in a subject.

In yet another aspect, the invention pertains to a packaged pharmaceutical composition for treating amyloidosis in a subject, comprising a container holding a therapeutically effective amount of a therapeutic formulation comprising a therapeutic compound formulated to significantly reduce or prevent gastrointestinal intolerance; and instructions for using the compound for treating amyloidosis in a subject.

In yet another aspect, the invention pertains to a packaged pharmaceutical composition for treating Alzheimer's disease in a subject, comprising a container holding a therapeutically effective amount of a therapeutic formulation comprising a therapeutic compound formulated to significantly reduce or prevent gastrointestinal intolerance; and instructions for using the compound for treating Alzheimer's disease in a subject.

Another aspect of the invention is a packaged pharmaceutical composition for treating a viral infection, comprising a container holding a therapeutically effective amount of a therapeutic formulation comprising a therapeutic compound formulated to significantly reduce or prevent gastrointestinal intolerance; and instructions for using the compound for treating the viral infection.

In an additional aspect, the invention is directed to a packaged pharmaceutical composition for treating a bacterial infection, comprising a container holding a therapeutically effective amount of a therapeutic formulation comprising a therapeutic compound formulated to significantly reduce or prevent gastrointestinal intolerance; and instructions for using the therapeutic compound for treating the bacterial infection.

In another aspect, the invention pertains to a packaged pharmaceutical composition for inhibiting the binding of a chemokine to a glycosaminoglycan, comprising a container holding a therapeutically effective amount of a therapeutic formulation comprising a therapeutic compound formulated to significantly reduce or prevent gastrointestinal intolerance; and instructions for using the therapeutic compound for inhibiting the binding of a chemokine to a glycosaminioglycan.

In yet another aspect, the invention pertains to method of making a therapeutic formulation comprising combining a therapeutically effective amount of a therapeutic compound and a pharmaceutically acceptable vehicle, wherein the therapeutic formulation is formulated to significantly reduce or prevent gastrointestinal intolerance.

An additional aspect of the invention is directed to a pharmaceutical formulation comprising greater than 5% by weight of 3-amino-1-propanesulfonic acid ("3-APS").

In another aspect, the invention is a pharmaceutical formulation comprising a therapeutic compound and greater than 1% by weight of an additional agent.

In yet another aspect, the invention pertains to a method for inhibiting amyloid deposition in a subject comprising administering to the subject an effective amount of a therapeutic formulation comprising a therapeutic compound formulated with an enteric-coating, such that amyloid deposition is inhibited.

Another aspect of the invention is directed to a method for inhibiting amyloid deposition in a subject comprising administering to the subject an effective amount of a therapeutic formulation comprising a therapeutic compound formulated with an agent that modifies the release of the therapeutic compound, such that amyloid deposition is inhibited.

Additionally, a further aspect of the invention is a pharmaceutical composition for inhibiting amyloid deposition in a subject comprising a therapeutic compound formulated with an enteric-coating, such that amyloid deposition is inhibited.

In another aspect, the present invention pertains to a pharmaceutical composition for inhibiting amyloid deposition in a subject comprising a therapeutic compound formulated with all agent that modifies the release of the therapeutic compound, such that amyloid deposition is inhibited.

In yet another aspect, the invention pertains to a method of formulating a gastrointestinal intolerance enhanced pharmaceutical composition comprising: combining a pre-selected therapeutic compound with a pharmaceutically acceptable carrier, wherein the therapeutic compound is pre-selected for its ability to significantly reduce or prevent gastrointestinal intolerance, forming a gastrointestinal intolerance enhanced pharmaceutical composition.

In an additional aspect, the invention is directed to a method for preventing or treating amyloid-related disease in a subject comprising administering to the subject an effective amount of a therapeutic formulation comprising a therapeutic compound formulated with an enteric-coating, such that amyloid-related disease is prevented or treated.

Another aspect of the invention is a method for preventing or treating amyloid-related disease in a subject comprising administering to the subject an effective amount of a therapeutic formulation comprising a therapeutic compound formulated with an agent that modifies the release of the therapeutic compound, such that amyloid-related disease is prevented or treated.

In another aspect, the invention is directed to a pharmaceutical composition for preventing or treating amyloid-related disease in a subject comprising a therapeutic compound formulated with an enteric-coating.

In yet another aspect, the invention pertains to a pharmaceutical composition for preventing or treating amyloid-related disease in a subject comprising a therapeutic compound formulated with an agent that modifies the release of the therapeutic compound.

Another aspect of the invention is a method for inhibiting amyloid deposition in a subject comprising administering to the subject an effective amount of a therapeutic formulation comprising a therapeutic compound formulated to significantly reduce or prevent gastrointestinal intolerance, wherein the therapeutic formulation is formulated as described in Example 6, such that amyloid deposition is inhibited.

Yet another aspect of the invention pertains to a method of treating or preventing an amyloid-related disease in a subject comprising administering to a subject a therapeutic amount of a therapeutic formulation comprising a therapeutic compound formulated to significantly reduce or prevent gastrointestinal intolerance, wherein the therapeutic formulation is formulated as described in Example 6, such that the amyloid-related disease is treated or prevented.

In another aspect, the invention is a method for inhibiting amyloid deposition in a subject comprising administering to the subject an effective amount of a therapeutic formulation comprising a therapeutic compound formulated to significantly reduce or prevent gastrointestinal intolerance, wherein the therapeutic formulation is formulated as described in Example 6, such that the therapeutic compound inhibits an interaction between an amyloidogenic protein and a constituent of a basement membrane to inhibit amyloid deposition.

In yet another aspect, the invention is directed to a method for inhibiting amyloid deposition in a subject comprising administering to the subject an effective amount of a therapeutic formulation comprising a therapeutic compound formulated to significantly reduce or prevent gastrointestinal intolerance, wherein the therapeutic formulation is formulated as described in Example 6, such that the therapeutic compound inhibits neurodegeneration or cellular toxicity induced by amyloid.

An additional aspect of the invention pertains to a method for inhibiting amyloid deposition in a subject comprising administering to the subject an effective amount of a therapeutic formulation comprising a therapeutic compound formulated to significantly reduce or prevent gastrointestinal intolerance, wherein the therapeutic formulation is formulated as described in Example 6, such that the therapeutic compound enhances clearance of amyloid $\beta$ from the brain.

In an additional aspect, the invention is a method for inhibiting amyloid deposition in a subject comprising orally administering to the subject an effective amount of a therapeutic formulation comprising a therapeutic compound formulated to significantly reduce or prevent gastrointestinal intolerance, wherein the therapeutic formulation is formulated as described in Example 6, such that amyloid deposition is inhibited.

Another aspect of the invention is directed to a pharmaceutical composition for inhibiting amyloid deposition in a subject comprising a therapeutic formulation comprising a therapeutic compound formulated to significantly reduce or prevent gastrointestinal intolerance, in an amount sufficient to inhibit amyloid deposition in a subject, and a pharmaceutically acceptable vehicle, wherein the therapeutic formulation is formulated as described in Example 6.

In yet another aspect, the invention is a pharmaceutical composition for treating amyloidosis comprising a therapeutic formulation comprising a therapeutic compound formulated to significantly reduce or prevent gastrointestinal intolerance, in an amount sufficient to treat amyloidosis in a subject, and a pharmaceutically acceptable vehicle, wherein the therapeutic formulation is formulated as described in Example 6.

An additional aspect of the invention is directed to a pharmaceutical composition for treating or preventing an amyloid-related disease comprising a therapeutic formulation comprising a therapeutic compound formulated to significantly reduce or prevent gastrointestinal intolerance, in an amount sufficient to prevent or treat an amyloid-related disease in a subject, and a pharmaceutically acceptable vehicle, wherein the therapeutic formulation is formulated as described in Example 6.

In an additional aspect, the invention pertains to a method for reducing amyloid deposits in a subject having amyloid deposits, the method comprising administering to the subject an effective amount of a therapeutic formulation comprising a therapeutic compound formulated to significantly reduce or prevent gastrointestinal intolerance, wherein the therapeutic formulation is formulated as described in Example 6, such that amyloid deposits are reduced in the subject.

In another aspect, the invention is directed to a method for inhibiting the binding of a chemokine to a glycosaminoglycan in a subject comprising administering to the subject a therapeutic formulation comprising a therapeutic compound formulated to significantly reduce or prevent gastrointestinal intolerance, wherein the therapeutic formulation is formulated as described in Example 6, such that the binding of a chemokine to a glycosaminoglycan is inhibited.

Another aspect of the invention pertains to a method for modulating interaction between a bacterium and a glycosaminoglycan in a human comprising administering to the human an effective amount of a therapeutic formulation comprising a therapeutic compound formulated to significantly reduce or prevent gastrointestinal intolerance, wherein the therapeutic formulation is formulated as described in Example 6.

An additional aspect of the invention pertains to a method for treating a bacterial infection in a human comprising administering to the human an effective amount of a therapeutic formulation comprising a therapeutic compound formulated to significantly reduce or prevent gastrointestinal intolerance, wherein the therapeutic formulation is formulated as described in Example 6.

In another aspect, the invention is directed to a method for modulating interaction between a virus and a glycosaminoglycan in a subject comprising administering to the subject an effective amount of a therapeutic formulation comprising a therapeutic compound formulated to significantly reduce or prevent gastrointestinal intolerance, wherein the therapeutic formulation is formulated as described in Example 6.

In yet another aspect, the invention is a method for treating a viral infection in a subject comprising administering to the subject a therapeutic formulation comprising an effective amount of a therapeutic formulation comprising a therapeutic compound formulated to significantly reduce or prevent gastrointestinal intolerance, wherein the therapeutic formulation is formulated as described in Example 6.

Another aspect of the invention pertains to a method of preventing, treating or inhibiting cerebral amyloid angiopathy in a subject, comprising administering an effective amount of a therapeutic formulation comprising a therapeutic compound formulated to significantly reduce or prevent gastrointestinal intolerance, wherein the therapeutic formulation is formulated as described in Example 6.

In an additional aspect, the invention is directed to a method of preventing, treating or inhibiting cerebral amyloid angiopathy, comprising contacting a blood vessel wall cell with a therapeutic formulation therapeutic formulation comprising a therapeutic compound formulated to significantly reduce or prevent gastrointestinal intolerance, wherein the therapeutic formulation is formulated as described in Example 6, such that cerebral amyloid angiopathy is prevented, treated, or inhibited.

An additional aspect of the invention pertains to a method of preventing, treating or inhibiting cerebral amyloid angiopathy, comprising contacting a blood vessel wall cell with a therapeutic compound of a therapeutic formulation therapeutic formulation, formulated to significantly reduce or prevent gastrointestinal intolerance, wherein the therapeutic formulation is formulated as described in Example 6, such that cerebral amyloid angiopathy is prevented, treated, or inhibited.

In another aspect, the invention is directed to a method of preventing or treating Alzheimer's disease in a subject, comprising administering to the subject an effective amount of a therapeutic formulation comprising a therapeutic compound formulated to significantly reduce or prevent gastrointestinal intolerance, wherein the therapeutic formulation is formulated as described in Example 6.

In yet another aspect, the invention is a packaged pharmaceutical composition for inhibiting amyloid deposition in a subject, comprising a container holding a therapeutically effective amount of a therapeutic formulation comprising a therapeutic compound formulated to significantly reduce or prevent gastrointestinal intolerance, wherein the therapeutic formulation is formulated as described in Example 6; and instructions for using the compound for inhibiting amyloid deposition in a subject.

Another aspect of the invention pertains to a packaged pharmaceutical composition for treating amyloidosis in a subject, comprising a container holding a therapeutically effective amount of a therapeutic formulation comprising a therapeutic compound formulated to significantly reduce or prevent gastrointestinal intolerance, wherein the therapeutic formulation is formulated as described in Example 6; and instructions for using the compound for treating amyloidosis in a subject.

An additional aspect of the invention pertains to a packaged pharmaceutical composition for treating a viral infection, comprising a container holding a therapeutically effective amount of a therapeutic formulation comprising a therapeutic compound formulated to significantly reduce or prevent gastrointestinal intolerance, wherein the therapeutic formulation is formulated as described in Example 6; and instructions for using the compound for treating the viral infection.

In another aspect, the invention is directed to a packaged pharmaceutical composition for treating a bacterial infection, comprising a container holding a therapeutically effective amount of a therapeutic formulation comprising a therapeutic compound formulated to significantly reduce or prevent gastrointestinal intolerance, wherein the therapeutic formulation is formulated as described in Example 6; and instructions for using the therapeutic compound for treating the bacterial infection.

In yet another aspect, the invention is a packaged pharmaceutical composition for inhibiting the binding of a chemokine to a glycosaminoglycan, comprising a container holding a therapeutically effective amount of a therapeutic formulation comprising a therapeutic compound formulated to significantly reduce or prevent gastrointestinal intolerance, wherein the therapeutic formulation is formulated as described in Example 6; and instructions for using the therapeutic compound for inhibiting the binding of a chemokine to a glycosaminoglycan.

An additional aspect of the invention pertains to a method of making a therapeutic formulation comprising combining a therapeutically effective amount of a therapeutic compound and a pharmaceutically acceptable vehicle, wherein the therapeutic formulation is formulated to significantly reduce or prevent gastrointestinal intolerance, and wherein the therapeutic formulation is formulated as described in Example 6.

In another aspect, the invention is directed to a method for inhibiting amyloid deposition in a subject comprising administering to the subject an effective amount of a therapeutic formulation comprising a therapeutic compound formulated with ala enteric-coating, wherein the therapeutic formulation is formulated as described in Example 6, such that amyloid deposition is inhibited.

In yet another aspect, the invention is a method for inhibiting amyloid deposition in a subject comprising administering to the subject an effective amount of a therapeutic formulation comprising a therapeutic compound formulated with an agent that modifies the release of the therapeutic compound, wherein the therapeutic formulation is formulated as described in Example 6, such that amyloid deposition is inhibited.

Another aspect of the invention pertains to a pharmaceutical composition for inhibiting amyloid deposition in a subject comprising a therapeutic compound formulated with an enteric-coating, wherein the therapeutic formulation is formulated as described in Example 6.

In an additional aspect, the invention is directed to a pharmaceutical composition for inhibiting amyloid deposition in a subject comprising a therapeutic compound formulated with an agent that modifies the release of the therapeutic compound, wherein the therapeutic formulation is formulated as described in Example 6.

An additional aspect of the invention pertains to a method of formulating a gastrointestinal intolerance enhanced pharmaceutical composition comprising: combining a pre-selected therapeutic compound with a pharmaceutically acceptable carrier, wherein the therapeutic compound is pre-selected for its ability to significantly reduce or prevent gastrointestinal intolerance, forming a gastrointestinal intolerance enhanced pharmaceutical composition as described in Example 6.

In another aspect, the invention is directed to a method for preventing or treating amyloid-related disease in a subject comprising administering to the subject an effective amount of a therapeutic formulation comprising a therapeutic compound formulated with an enteric-coating, wherein the therapeutic formulation is formulated as described in Example 6, such that amyloid-related disease is prevented or treated.

In yet another aspect, the invention is a method for preventing or treating amyloid-related disease in a subject comprising administering to the subject an effective amount of a therapeutic formulation comprising a therapeutic compound formulated with an agent that modifies the release of the therapeutic compound, wherein the therapeutic formulation is formulated as described in Example 6, such that amyloid-related disease is prevented or treated.

Another aspect of the invention pertains to a pharmaceutical composition for preventing or treating amyloid-related disease in a subject comprising a therapeutic compound formulated with an enteric-coating, wherein the therapeutic formulation is formulated as described in Example 6.

An additional aspect of the invention pertains to a pharmaceutical composition for preventing or treating amyloid-related disease in a subject comprising a therapeutic compound formulated with an agent that modifies the release of the therapeutic compound, wherein the therapeutic formulation is formulated as described in Example 6.

In another aspect, the invention is directed to a method of preventing, treating or inhibiting Alzheimer's disease in a subject, comprising administering to the subject an effective amount of a therapeutic formulation comprising a therapeutic compound formulated to significantly reduce or prevent gastrointestinal intolerance, wherein the therapeutic formulation is formulated as described in Example 6, such that Alzheimer's disease is prevented, treated, or inhibited.

In yet another aspect, the invention is a packaged pharmaceutical composition for treating Alzheimer's disease in a subject, comprising a container holding a therapeutically effective amount of a therapeutic formulation comprising a therapeutic compound formulated to significantly reduce or prevent gastrointestinal intolerance, wherein the therapeutic formulation is formulated as described in Example 6; and instructions for using the compound for treating Alzheimer's disease in a subject.

Another aspect of the invention is a formulation, preferably oral, comprising 3-amino-1-propanesulfonic acid (i.e., 3-APS) or a pharmaceutically acceptable salt thereof in an effective amount to treat amyloidosis, inhibit or prevent amyloid deposition and/or treat or prevent an amyloid-related disease and a pharmaceutically acceptable vehicle, wherein the formulation has a mean plasma concentration pharmacokinetic (PK) profile such that, when the formulation is administered in a dose of 50 mg of the active agent, e.g., to patients suffering from mild to moderate Alzheimer's disease, e.g., in a fasted state, said PK profile has at least one of the following parameters: a mean $AUC_{0-t}$ of about 1321 ng·h/mL, a mean $AUC_\infty$ of about 1396 ng·h/mL, a mean Cmax of about 310 ng/mL, and a median Tmax of about 6 hours (each parameter being within ±50%, more preferably ±40% and particularly preferably ±20% of said respective value, (see Example 10 below)), or, when the formulation is administered in another dose amount, a mean $AUC_{0-t}$, $AUC_\infty$ and Cmax linearly related to that for the 50 mg dose are achieved. In a modification of this aspect, the mean $AUC_{0-t}$ is in the range from 126 to 4259, preferably 500 to 2500, ng·h/mL, the mean $AUC_\infty$ is in the range from 157 to 4311, preferably 500 to 2500, ng·h/mL, the mean Cmax is in the range from 27 to 776, preferably 100 to 500, ng/mL, and the median Tmax is in the range from 2 to 9 hours, preferably 4 to 8 hours, (optionally, the respective minimum and maximum values of the ranges being ±50%, more preferably ±40% and particularly preferably ±20%).

Another aspect of the invention is a formulation, preferably oral, comprising 3-amino-1-propanesulfonic acid (i.e., 3-APS) or a pharmaceutically acceptable salt thereof in an effective amount to treat amyloidosis, inhibit or prevent amyloid deposition and/or treat or prevent an amyloid-related disease and a pharmaceutically acceptable vehicle, wherein the formulation has a mean plasma concentration (pharmacokinetic (PK)) profile such that, when the formulation is administered in a dose of 100 mg of the active agent, e.g., to patients suffering from mild to moderate Alzheimer's disease, e.g., in a fasted state, said PK profile has at least one of the following parameters: a mean $AUC_{0-t}$ of about 2467 ng·h/mL, a mean $AUC_\infty$ of about 2569 ng·h/mL, a mean Cmax of about 618 ng/mL, and a median Tmax of about 4.7 hours, each parameter being within ±50%, more preferably ±40% and particularly preferably ±20% of said respective value, (see Example 10 below), or, when the formulation is administered in another dose amount, a mean $AUC_{0-t}$, $AUC_\infty$ and Cmax linearly related to that for the 100 mg dose are achieved. In a modification of this aspect, the mean $AUC_{0-t}$ is in the range from 829 to 5123, preferably 1500 to 3500 ng·h/mL, the mean $AUC_\infty$ is in the range from 861 to 5385, preferably 1500 to 3500 ng·h/mL, the mean Cmax is in the range from 220 to 1666, preferably 300 to 1000, ng/mL, and the median Tmax is in the range from 2 to 8 hours, preferably 4 to 7 hours (optionally, the respective minimum and maximum values of the ranges being ±50%, more preferably ±40% and particularly preferably ±20%).

Another aspect of the invention is a formulation, preferably oral, comprising 3-amino-1-propanesulfonic acid (i.e., 3-APS) or a pharmaceutically acceptable salt thereof in an effective amount to treat amyloidosis, inhibit or prevent amyloid deposition and/or treat or prevent an amyloid-related disease and a pharmaceutically acceptable vehicle, wherein the formulation has a mean plasma concentration pharmacokinetic (PK) profile such that, when the formulation is administered in a dose of 150 mg of the active agent, e.g., to patients suffering from mild to moderate Alzheimer's disease, e.g., in a fasted state, said PK profile has at least one of the following parameters: a mean $AUC_{0-t}$ of about 2792 ng·h/mL, a mean $AUC_\infty$ of about 3418 ng·h/mL, a mean Cmax of about 624 ng/mL, a median Tmax of about 6 hours, each parameter being within ±50%, more preferably ±40% and particularly preferably ±20% of said respective value, (see Example 10 below), or, when the formulation is administered in another dose amount, a mean $AUC_{0-t}$, $AUC_\infty$ and Cmax linearly related to that for the 150 mg dose are achieved. In a modification of this aspect, the mean $AUC_{0-t}$ is in the range from 75 to 9042, preferably 1000 to 5000 ng·h/mL, the mean $AUC_\infty$ is in the range from 670 to 9627, preferably 1000 to 5000, ng·h/mL, the mean Cmax is in the range from 14 to 1875, preferably 300 to 1000, ng/mL, and the median Tmax is in the range from 2 to 12 hours, preferably 4 to 9 hours (optionally, the respective minimum and maximum values of the ranges being ±50%, more preferably ±40% and particularly preferably ±20%).

Another aspect of the invention is a formulation, preferably oral, comprising 3-amino-1-propanesulfonic acid (i.e., 3-APS) or a pharmaceutically acceptable salt thereof in an effective amount to treat amyloidosis, inhibit or prevent amyloid deposition and/or treat or prevent an amyloid-related disease and a pharmaceutically acceptable vehicle, wherein the formulation has pharmacokinetic parameters (within ±50%, more preferably ±40% and particularly preferably ±20%) of those shown in each of Examples 7 to 10 below, in the types of patients as shown (e.g., young and healthy, elderly and healthy, fasted or fed, etc.).

Further aspects of the invention include formulations which combine two or more of the pharmacokinetic parameters, or sets of pharmacokinetic parameters (e.g., $AUC_{0-t}$, $AUC_\infty$, Cmax and/or Tmax), described above. For example, such aspects include formulations which provide one or more of the pharmacokinetic parameters, or sets thereof, as shown herein when administered to young healthy patients and one or more of the pharmacokinetic parameters, or sets thereof, as shown herein when administered to elderly healthy patients and/or elderly patients with Alzheimer's Disease (AD) or exhibiting one or more of the indicators for AD as discussed herein. It has been discovered that there is an effect of age on the pharmacokinetic parameters observed for 3-APS. Elderly patients exhibited a higher systemic exposure to the drug than younger patients when subjected to the same dose. For example, at a 200 mg dose, the $AUC_{0-t}$ and $C_{max}$ were approximately 70% greater in elderly subjects compared to those for young subjects. See, e.g., Tables 9 and 10 below.

A further aspect includes formulations as described above wherein the formulation includes an enteric coating and/or a pharmaceutically acceptable vehicle, different from the enteric coating, which modifies immediate release of the active agent. A further aspect includes formulations as described above wherein the formulation is effective for osmotic release, pulsatile release, sustained release, controlled release, delayed release, extended release, or other modified release of the active agent.

In another aspect, the active agent is provided in an oral therapeutic formulation such that little or no dissolution of the active agent occurs in the acidic environment of the stomach but dissolution does occur in the more neutral or alkaline environments of the GI tract. Although there is no limitation, the active agent may, for example, be provided in a formulation which has 20% or less dissolution in the stomach, more preferably 15% or less, particularly 10% or less or 5% or less. In vitro dissolution tests, according to known standards, may be used to give a reasonable indication of what can be expected in vivo. For example, one test for in vitro dissolution of pH dependent enteric materials is USP28-NF23 <711> (paddle speed 75 rpm) and it requires no more than 10% release in 0.1N HCl for 2 hours. The buffer is then switched to a more alkaline buffer based on the type of enteric coating, for example, a pH of 6-8, particularly 6.5 to 7.0, such as 6.8. After the pH change, the dissolution of the active agent increases, for example, at least 75% is dissolved within 60 minutes of buffer change. Enteric formulations which are pH independent can also be used, as is known in the art. These provide for release of the drug after a certain time, independent of the pH. Standards for assessing dissolution of such formulations are also known. Although these tests are conducted in vitro and give a reasonable indication of what can be expected in vivo, it is well understood in the art that in vivo dissolution in the stomach and G.I. tract are affected by many factors. One of the main factors is whether the stomach is in a fed or fasted state. Gastric emptying times in the fasted state range from, for example, 30 minutes to 2 hours, while in the fed state gastric emptying is generally significantly slower, e.g., as slow as 7 hours. Thus, for pH independent enteric formulations, it may be useful to provide formulations which delay significant dissolution, e.g., no more than 20%, 15%, 10% or 5%, for from 30 minutes up to 3 hours, for example, 1-2 hours, or 2 hours, after administration.

Further aspects of the invention include methods for administering the above formulations. Included are:

methods for lessening gastrointestinal side effects in a human patient which occur from orally administering an active agent which is 3-amino-1-propanesulfonic acid or a pharmaceutically acceptable salt thereof, comprising administering said agent in a formulation effective to lessen the increase in pH of the stomach when administered compared to that which occurs when said agent is administered in an immediate release dosage form;

methods of lessening gastrointestinal side effects in a human patient which occur from orally administering an active agent which is 3-amino-1-propanesulfonic acid or a pharmaceutically acceptable salt thereof, comprising administering said agent in a formulation, as disclosed herein, which is effective to treat amyloidosis, inhibit or prevent amyloid deposition and/or treat or prevent an amyloid-related disease with lesser side effects in comparison to those which occur when said active agent is administered in an immediate release dosage form, the immediate release dosage formulation compared being, for example, that described in Table 2 below;

methods of orally administering an active agent which is 3-amino-1-propanesulfonic acid or a pharmaceutically acceptable salt thereof in a formulation which is effective to treat amyloidosis, inhibit or prevent amyloid deposition and/or treat or prevent an amyloid-related disease with a low occurrence of side effects, particularly a low occurrence of nausea and/or vomiting, for example, where the side effects are observed in 35% or less of the patients, particularly 25% or less, 20% or less, 15% or less, 10% or less, or 5% or less of the patients;

methods of treating amyloidosis, inhibiting or preventing amyloid deposition and/or treating or preventing an amyloid-related disease in a patient in need thereof comprising administering a formulation as described herein;

methods for treating an Aβ-related disease in a patient in need thereof comprising administering a formulation as described herein;

methods for lowering levels of Aβ1-39, Aβ1-40, Aβ1-41, Aβ1-42, and/or Aβ1-43, particularly Aβ1-42, in the cerebrospinal fluid and/or plasma of a patient which comprises orally administering to the patient a formulation as described herein;

methods for lowering the ratio of Aβ1-42 to Aβ1-40 levels in the cerebrospinal fluid and/or plasma of a patient which comprises orally administering to the patient a formulation as described herein;

methods for stabilizing cognitive function or decreasing the rate of decline in cognitive function (for example, as assessed by Clinical Dementia Rating (CDR) scale, Mini-mental State Examination (MMSE), or Alzheimer's Disease Assessment Scale-Cognitive Subscale (ADAS-Cog)) in a patient in need thereof comprising administering a formulation as described herein;

methods of lessening gastrointestinal side effects in a human patient which occur from orally administering an active agent which is 3-amino-1-propanesulfonic acid or a pharmaceutically acceptable salt thereof, comprising administering said agent according to a schedule wherein an initial dose is administered and the dose is increased over time to a higher dose which treats amyloidosis, inhibits or prevents amyloid deposition and/or treats or prevents an amyloid-related disease, for example: where the formulation is administered in an initial dose for one month followed by an increased dose the second month, which is optionally maintained throughout the treatment, or is followed by an increased dose for the third month which is maintained throughout the treatment, such as wherein the patient is administered 50 mg doses in the first month and 100 mg doses in the second and following months of treatment or wherein the patient is administered 50 mg doses in the first month, 100 mg doses in the second month and 150 mg doses in the third and following months of treatment; said doses may, for example, be administered once or twice daily;

any of the methods described herein which further comprises administering another therapeutic agent, for example, another agent which is effective for treating amyloidosis, inhibiting or preventing amyloid deposition and/or treating or preventing an amyloid-related disease, examples of which are discussed below;

any of the methods described herein wherein the active agent is administered in doses of about 25 to about 200 mg, preferably about 50 to about 150 mg, more preferably about 50, about 100 or about 150 mg, and, preferably, daily or twice daily, or lower or higher amounts.

In other aspects, these methods involve administration to a patient in need of treatment of amyloidosis, inhibition or prevention of amyloid deposition and/or treatment or prevention of an amyloid-related disease, more preferably wherein said administration is to a patient in need of treatment for an Aβ-related disease, e.g., Alzheimer's disease ("AD") and/or cerebral amyloid angiopathy ("CAA"), particularly AD.

Another aspect is a method for treating a patient having Alzheimer's disease ("AD") or preventing or slowing the development of AD in a patient comprising administering any of the formulations discussed herein.

In other aspects, the invention is directed to formulations and methods for treatment, as described above, wherein the active agent is 3-amino-1-propanesulfonic acid or a pharmaceutically acceptable salt thereof provided in a modified release formulation. The modified release formulation is such that, for example:

the formulation lessens the gastrointestinal side effects in a human patient which occur from administration of the active agent in an immediate release dosage form, the formulation includes an enteric coating, the formulation includes a pharmaceutically acceptable vehicle which modifies the release of the active agent, which is different from an enteric coating and is used with or without an enteric coating, the formulation is in a form for osmotic release, pulsatile release, sustained release, controlled release, delayed release, extended release or other modified release of the active agent, the formulation is effective to lessen the increase in pH of the stomach when administered compared to that which occurs when said agent is administered in an immediate release dosage form, the formulation comprises an effective amount of said agent to inhibit or prevent amyloid deposition and/or treat or prevent an amyloid-related disease and a pharmaceutically acceptable vehicle, the formulation comprises an effective amount of the active agent to treat or prevent an Aβ-related disease, such as AD and/or CAA, the formulation is effective for stabilizing cognitive function or decreasing the rate of decline in cognitive function (for example, as assessed by Clinical Dementia Rating (CDR) scale, Mini-mental State Examination (MMSE), or Alzheimer's Disease Assessment Scale-Cognitive Subscale (ADAS-Cog)) in a patient, the formulation is effective to treat amyloidosis, inhibit or prevent amyloid deposition and/or treat or prevent an amyloid-related disease with lesser side effects in comparison to those which occur when said active agent is administered in an immediate release dosage form, the formulation is effective to lower levels of Aβ1-39, Aβ1-40, Aβ1-41, Aβ1-42, and/or Aβ1-43 in the cerebrospinal fluid and/or the plasma of a patient, particularly to lower Aβ1-40 and/or Aβ1-42, most particularly, Aβ1-42, or the formulation is effective to lower the ratio of the levels Aβ1-42 to Aβ1-40 in the cerebrospinal fluid and/or the plasma of a patient, any combination of the above aspects.

DETAILED DESCRIPTION OF THE INVENTION

This invention pertains to methods, compositions, and formulations useful for treating amyloidosis. The methods of the invention involve administering to a subject a therapeutic formulation comprising a therapeutic compound that inhibits amyloid deposition. In particular, the present invention therefore relates to the use of therapeutic formulations, e.g., comprising alkylsulfonic acids, in the prevention or treatment of amyloid-related diseases, including, inter alia, Alzheimer's disease, cerebral amyloid angiopathy, inclusion body myositis, macular degeneration, Down's syndrome, Mild Cognitive Impairment, and type II diabetes.

I. Amyloid-Related Diseases

The present invention relates to the use of pharmaceutical compositions or formulations comprising therapeutic compounds useful in the treatment of amyloid-related diseases. Many amyloid-related diseases are known, and others doubtless exist.

AA (Reactive) Amyloidosis

Generally, AA amyloidosis is a manifestation of a number of diseases that provoke a sustained acute phase response. Such diseases include chronic inflammatory disorders, chronic local or systemic microbial infections, and malignant neoplasms. The most common form of reactive or secondary (AA) amyloidosis is seen as the result of long-standing inflammatory conditions. For example, patients with Rheumatoid Arthritis or Familial Mediterranean Fever (which is a genetic disease) can develop AA amyloidosis. The terms "AA amyloidosis" and "secondary (AA) amyloidosis" are used interchangeably.

AA fibrils are generally composed of 8,000 Dalton fragments (AA peptide or protein) formed by proteolytic cleavage of serum amyloid A protein (ApoSAA), a circulating apolipoprotein which is mainly synthesized in hepatocytes in response to such cytokines as IL-1, IL-6 and TNF. Once secreted, ApoSAA is complexed with HDL. Deposition of AA fibrils can be widespread in the body, with a preference for parenchymal organs. The kidneys are usually a deposition site, and the liver and the spleen may also be affected. Deposition is also seen in the heart, gastrointestinal tract, and the skin.

Underlying diseases which can lead to the development of AA amyloidosis include, but are not limited to inflammatory diseases, such as rheumatoid arthritis, juvenile chronic arthritis, ankylosing spondylitis, psoriasis, psoriatic arthopathy, Reiter's syndrome, Adult Still's disease, Behcet's syndrome, and Crohn's disease. AA deposits are also produced as a result of chronic microbial infections, such as leprosy, tuberculosis, bronchiectasis, decubitus ulcers, chronic pyelonephritis, osteomyelitis, and Whipple's disease. Certain malignant neoplasms can also result in AA fibril amyloid deposits. These include such conditions as Hodgkin's lymphoma, renal carcinoma, carcinomas of gut, lung and urogenital tract, basal cell carcinoma, and hairy cell leukemia. Other underlying conditions that may be associated with AA amyloidosis are Castleman's disease and Sclmitzler's syndrome.

AL Amyloidoses (Primary Amyloidosis)

AL amyloid deposition is generally associated with almost any dyscrasia of the B lymphocyte lineage, ranging from malignancy of plasma cells (multiple myeloma) to benign monoclonal gammopathy. At times, the presence of amyloid deposits may be a primary indicator of the underlying dyscrasia. AL amyloidosis is also described in detail in *Current Drug Targets,* 2004, 5 159-171.

Fibrils of AL amyloid deposits are composed of monoclonal immunoglobulin light chains or fragments thereof. More specifically, the fragments are derived from the N-terminal region of the light chain (kappa or lambda) and contain all or part of the variable ($V_L$) domain thereof. Deposits generally occur in the mesenchymal tissues, causing peripheral and autonomic neuropathy, carpalumel syndrome, macroglossia, restrictive cardiomyopathy, arthropathy of large joints, immune dyscrasias, myelomas, as well as occult dyscrasias. However, it should be noted that almost any tissue, particularly visceral organs such as the kidney, liver, spleen and heart, may be involved.

Hereditary Systemic Amyloidoses

There are many forms of hereditary systemic amyloidoses. Although they are relatively rare conditions, adult onset of symptoms and their inheritance patterns (usually autosomal dominant) lead to persistence of such disorders in the general population. Generally, the syndromes are attributable to point mutations in the precursor protein leading to production of variant amyloidogenic peptides or proteins. Table 1 summarizes the fibril composition of exemplary forms of these disorders.

TABLE 1

Fibril Composition of Exemplary Amyloid-Related Diseases

| Fibril Peptide/Protein | Genetic Variant | Clinical Syndrome |
|---|---|---|
| ATTR protein from Transthyretin and fragments | Met30, many others | Familial amyloid polyneuropathy (FAP), (Mainly peripheral nerves) |
| ATTR protein from Transthyretin and fragments | Thr45, Ala60, Ser84, Met111, Ile122 | Cardiac involvement predominant without neuropathy, familial amyloid polyneuropathy, senile systemic amyloidosis, Tenosynovium |
| N-terminal fragment of Apolipoprotein A1 (apoAI) | Arg26 | Familial amyloid polyneuropathy (FAP), (mainly peripheral nerves) |
| N-terminal fragment of Apliproprotein A1 (AapoAI) | Arg26, Arg50, Arg 60, others | Ostertag-type, non-neuropathic (predominantly visceral involvement) |
| AapoAII from Apolipoprotein AII | | Familial amyloidosis |
| Lysozyme (Alys) | Thr56, His67 | Ostertag-type, non-neuropathic (predominantly visceral involvement) |

TABLE 1-continued

Fibril Composition of Exemplary Amyloid-Related Diseases

| Fibril Peptide/Protein | Genetic Variant | Clinical Syndrome |
|---|---|---|
| Fibrogen alpha chain fragment | Leu554, Val 526 | Cranial neuropathy with lattic corneal dystrophy |
| Gelsolin fragment (Agel) | Asn187, Tyr187 | Cranial neuropathy with lattice corneal dystrophy |
| Cystatin C fragment (ACys) | Glu68 | Hereditary cerebral hemorrhage (cerebral amyloid angiopathy) - Icelandic type |
| β-amyloid protein (Aβ) derived from Amyloid Precursor Protein (APP) | Gln693 | Hereditary cerebral hemorrhage (cerebral amyloid angiopathy) - Dutch type |
| β-amyloid protein (Aβ) derived from Amyloid Precursor Protein (APP) | Ile717, Phe717, Gly717 | Familial Alzheimer's Disease |
| β-amyloid protein (Aβ) derived from Amyloid Precursor Protein (APP), e.g., bPP 695 | Gln 618 | Alzheimer's disease, Down's syndrome, hereditary cerebral hemorrhage with amyloidosis, Dutch type |
| β-amyloid protein (Aβ) derived from Amyloid Precursor Protein (APP) | Asn670, Leu671 | Familial Dementia - probably Alzheimer's Disease |
| Prion Protein (PrP, APrP$^{SC}$) derived from Prp precursor protein (51-91 insert) | Leu102, Val167, Asn178, Lys200 | Familial Creutzfeldt-Jakob disease; Gerstmann-Sträussler-Scheinker syndrome (hereditary spongiform encephalopathies, prion diseases) |
| AA derived from Serum amyloid A protein (ApoSAA) | | Familial Mediterranean fever, predominant renal involvement (autosomal recessive) |
| AA derived from Serum amyloid A protein (ApoSAA) | | Muckle-Well's syndrome, nephropathy, deafness, urticaria, limb pain |
| Unknown | | Cardiomyopathy with persistent atrial standstill |
| Unknown | | Cutaneous deposits (bullous, papular, pustulodermal) |
| AH amyloid protein, derived from immunoglobulin heavy chain (gamma I) | Aγ I | Myeloma associated amyloidosis |
| ACal amyloid protein from (pro)calcitonin | (Pro) calcitonin | Medullary carcinomas of the thyroid |
| AANF amyloid protein from atrial natriuretic factor | | Isolated atrial amyloid |
| Apro from Prolactin | | Prolactinomas |
| Abri/ADan from ABri peptide | | British and Danish familial Dementia |

Data derived from Tan SY, Pepys MB. Amyloidosis. Histopathology, 25(5), 403-414 (Nov 1994), WHO/IUIS Nomenclature Subcommittee, Nomenclature of Amyloid and Amyloidosis. Bulletin of the World Health Organisation 1993; 71: 10508; and Merlini et al., Clin Chem Lab Med 2001; 39(11): 1065-75.

The data provided in Table 1 are exemplary and are not intended to limit the scope of the invention. For example, more than 40 separate point mutations in the transthyretin gene have been described, all of which give rise to clinically similar forms of familial amyloid polyneuropathy.

In general, any hereditary amyloid disorder can also occur sporadically, and both hereditary and sporadic forms of a disease present with the same characteristics with regard to amyloid. For example, the most prevalent form of secondary AA amyloidosis occurs sporadically, e.g., as a result of ongoing inflammation, and is not associated with Familial Mediterranean Fever. Thus general discussion relating to hereditary amyloid disorders below can also be applied to sporadic amyloidoses.

Transthyretin (TTR) is a 14 kiloDalton protein that is also sometimes referred to as prealbumin. It is produced by the liver and choroid plexus, and it functions in transporting thyroid hormones and vitamin A. At least 50 variant forms of the protein, each characterized by a single amino acid change, are responsible for various forms of familial amyloid polyneuropathy. For example, substitution of proline for leucine at position 55 results in a particularly progressive form of neuropathy; substitution of methionine for leucine at position 111 resulted in a severe cardiopathy in Danish patients.

Amyloid deposits isolated from heart tissue of patients with systemic amyloidosis have revealed that the deposits are composed of a heterogeneous mixture of TTR and fragments thereof, collectively referred to as ATTR, the full length sequences of which have been characterized. ATTR fibril components can be extracted from such plaques and their structure and sequence determined according to the methods known in the art (e.g., Gustavsson, A., et al, Laboratory Invest. 73: 703-708, 1995; Kametani, F., et al., Biochem. Biophys. Res. Commun. 125: 622-628, 1984; Pras, M., et au, PNAS 80: 539-42, 1983).

Persons having point mutations in the molecule apolipoprotein Al (e.g., Gly→Arg26; Trp→Arg50; Leu→Arg60) exhibit a form of amyloidosis ("Östertag type") characterized by deposits of the protein apolipoprotein AI or fragments thereof (AApoAI). These patients have low levels of high density lipoprotein (HDL) and present with a peripheral neuropathy or renal failure.

A mutation in the alpha chain of the enzyme lysozyme (e.g., Ile→Thr56 or Asp→His57) is the basis of another form of Östertag-type non-neuropathic hereditary amyloid reported in English families. Here, fibrils of the mutant lysozyme protein (Alys) are deposited, and patients generally exhibit impaired renal function. This protein, unlike most of the fibril-forming proteins described herein, is usually present in whole (unfragmented) form (Benson, M. D., et al. CIBA Fdn. Symp. 199: 104-131, 1996).

Immunoglobulin light chains tend to form aggregates in various morphologies, including fibrillar (e.g., AL amyloidosis and AH amyloidosis), granular (e.g., light chain deposition disease (LCDD), heavy chain deposition disease (HCDD), and light-heavy chain deposition disease (LH- CDD)), crystalline (e.g., Acquired Farconi's Syndrome), and microtubular (e.g., Cryoglobulinemia). AL and AH amyloidosis is indicated by the formation of insoluble fibrils of immunoglobulin light chains and heavy chain, respectively, and/or their fragments. In AL fibrils, lambda (λ) chains such as λ VI chains (λ6 chains), are found in greater concentrations than kappa (κ) chains. λIII chains are also slightly elevated. Merlini et al, CLIN CHEM LAB MED 39(11):1065-75 (2001). Heavy chain amyloidosis (AH) is generally characterized by aggregates of gamma chain amyloid proteins of the IgG1 subclass. Eulitz et al., PROC NATL ACAD SCI USA 87:6542-46 (1990).

Comparison of amyloidogenic to non-amyloidogenic light chains has revealed that the former can include replacements or substitutions that appear to destabilize the folding of the protein and promote aggregation. AL and LCDD have been distinguished from other amyloid diseases due to their relatively small population monoclonal light chains, or fragments thereof, which are manufactured by neoplastic expansion of an antibody-producing B cell. AL aggregates typically are well-ordered fibrils of lambda chains. LCDD aggregates are relatively amorphous aggregations of both kappa and lambda chains, with a majority being kappa, in some cases κIV. Bellotti et al., JOURNAL OF STRUCTURAL BIOLOGY 13:280-89 (2000). Comparison of amyloidogenic and non-amyloidogenic heavy chains in patients having AH amyloidosis has revealed missing and/or altered components. Eulitz et al., PROC NATL ACAD SCI USA 87:6542-46 (1990) pathogenic heavy chain characterized by significantly lower molecular mass than non-amyloidogenic heavy chains); and Solomon et al. AM J HEMAT 45(2) 171-6 (1994) (amyloidogenic heavy chain characterized as consisting solely of the VH-D portion of the non-amyloidogenic heavy chain).

Accordingly, potential methods of detecting and monitoring treatment of subjects having or at of having AL, LCDD, AH, and the like, include but are not limited to immunoassaying plasma or urine for the presence or depressed deposition of amyloidogenic light or heavy chains, e.g., amyloid λ, amyloid κ, amyloid κIV, amyloid γ, or amyloid γ1.

Brain Amyloidosis

The most frequent type of amyloid in the brain is composed primarily of Aβ peptide fibrils, resulting in dementia associated with sporadic (non-hereditary) Alzheimer's disease. In fact, the incidence of sporadic Alzheimer's disease greatly exceeds forms shown to be hereditary. Nevertheless, fibril peptides forming plaques are very similar in both types. Brain amyloidosis includes those diseases, conditions, pathologies, and other abnormalities of the structure or function of the brain, including components thereof, in which the causative agent is amyloid. The area of the brain affected in an amyloid-related disease may be the stroma including the vasculature or the parenchyma including functional or anatomical regions, or neurons themselves. A subject need not have received a definitive diagnosis of a specifically recognized amyloid-related disease. The term "amyloid-related disease" includes brain amyloidosis.

Amyloid-β peptide ("Aβ") is a 39-43 amino acid peptide derived by proteolysis from a large protein known as Beta Amyloid Precursor Protein ("βAPP"). Mutations in βAPP result in familial forms of Alzheimer's disease, Down's syndrome, cerebral amyloid angiopathy, and senile dementia, characterized by cerebral deposition of plaques composed of Aβ fibrils and other components, which are described in further detail below. Known mutations in APP associated with Alzheimer's disease occur proximate to the cleavage sites of β or γ-secretase, or within Aβ. For example, position 717 is proximate to the site of gamma-secretase cleavage of APP in its processing to Aβ, and positions 670/671 are proximate to the site of β-secretase cleavage. Mutations at any of these residues may result in Alzheimer's disease, presumably by causing an increase in the amount of the 42/43 amino acid form of Aβ generated from APP. The familial form of Alzheimer's disease represents only 10% of the subject population. Most occurrences of Alzheimer's disease are sporadic cases where APP and Aβ do not possess any mutation. The structure and sequence of Aβ peptides of various lengths are well known in the art. Such peptides can be made according to methods known in the art, or extracted from the brain according to known methods (e.g., Glenner and Wong, Biochem. Biophys. Res. Comm. 129, 885-90 (1984); Glenner and Wong, Biochem. Biophys. Res. Comm. 122, 1131-35 (1984)). In addition, various forms of the peptides are commercially available. APP is expressed and constitutively catabolized in most cells. The dominant catabolic pathway appears to be cleavage of APP within the Aβ sequence by an enzyme provisionally termed α-secretase, leading to release of a soluble ectodomain fragment known as APPsα. This cleavage precludes the formation of Aβ peptide. In contrast to this non-amyloidogenic pathway, APP can also be cleaved by enzymes known as β- and γ-secretase at the N- and C-termini of the Aβ, respectively, followed by release of Aβ into the extracellular space. To date, BACE has been identified as β-secretase (Vasser, et al., Science 286:735-741, 1999) and presenilins have been implicated in γ-secretase activity (De Strooper, et al, Nature 391, 387-90 (1998)). The 39-43 amino acid Aβ peptide is produced by sequential proteolytic cleavage of the amyloid precursor protein (APP) by the β and γ secretases enzyme. Although Aβ40 is the predominant form produced, 5-7% of total Aβ exists as Aβ42 (Cappai et al., Int. J. Biochem. Cell Biol. 31. 885-89 (1999)).

The length of the Aβ peptide appears to dramatically alter its biochemical/biophysical properties. Specifically, the additional two amino acids at the C-terminus of Aβ42 are very hydrophobic, presumably increasing the propensity of Aβ42 to aggregate. For example, Jarrett, et al. demonstrated that Aβ42 aggregates very rapidly in vitro compared to Aβ40, suggesting that the longer forms of Aβ may be the important pathological proteins that are involved in the initial seeding of the neuritic plaques in Alzheimer's disease (Jarrett, et al, Biochemistry 32, 4693-97 (1993); Jarrett, et al., Ann. N.Y. Acad. Sci. 695, 144-48 (1993)). This hypothesis has been further substantiated by the recent analysis of the contributions of specific forms of Aβ in cases of genetic familial forms of Alzheimer's disease ("FAD"). For example, the "London" mutant form of APP (APPV717I) linked to FAD selectively increases the production of Aβ 42/43 forms versus Aβ 40 (Suzuki, et al., Science 264, 1336-40 (1994)) while the "Swedish" mutant form of APP (APPK670N/M671L) increases levels of both Aβ40 and Aβ42/43 (Citron, et al. Nature 360, 672-674 (1992); Cai, et al., Science 259, 514-16, (1993)). Also, it has been observed that FAD-linked mutations in the Presenilin-1 ("PS1") or Presenilin-2 ("PS2") genes will lead to a selective increase in Aβ42/43 production but not Aβ40 (Borchelt, et al., Neuron 17, 1005-13 (1996)). This finding was corroborated in transgenic mouse models expressing PS mutants that demonstrate a selective increase in brain Aβ42 (Borchelt, op cit.; Duff et al., Neurodegeneration 5(4), 293-98 (1996)). Thus the leading hypothesis regarding the etiology of Alzheimer's disease is that an increase in Aβ42 brain concentration due to an increased production and release of Aβ42 or a decrease in clearance (degradation or brain clearance) is a causative event in the disease pathology.

Multiple mutation sites in either Aβ or the APP gene have been identified and are clinically associated with either dementia or cerebral hemorrhage. Exemplary CAA disorders include, but are not limited to, hereditary cerebral hemorrhage with amyloidosis of Icelandic type (HCHWA-I); the Dutch variant of HCHWA (HCHWA-D; a mutation in Aβ); the Flemish mutation of Aβ; the Arctic mutation of Aβ); the Italian mutation of Aβ; the Iowa mutation of Aβ; familial British dementia; and familial Danish dementia. CAA may also be sporadic.

As used herein, the terms "β amyloid," "amyloid-β," and the like refer to amyloid β proteins or peptides, amyloid β precursor proteins or peptides, intermediates, and modifications and fragments thereof, unless otherwise specifically indicated. In particular, "Aβ" refers to any peptide produced by proteolytic processing of the APP gene product, especially peptides which are associated with amyloid pathologies, including Aβ1-39, Aβ1-40, Aβ1-41, Aβ1-42, and Aβ1-43. For convenience of nomenclature, "Aβ1-42" may be referred to herein as "Aβ(1-42)" or simply as "Aβ42" or "Aβ$_{42}$" (and likewise for any other amyloid peptides discussed herein). As used herein, the terms "β amyloid," "amyloid-β," and "Aβ" are synonymous.

Unless otherwise specified, the term "amyloid" refers to amyloidogenic proteins, peptides, or fragments thereof which can be soluble (e.g., monomeric or oligomeric) or insoluble (e.g., having fibrillary structure or in amyloid plaque). See, e.g., MP Lambert, et al., *Proc. Nat'l Acad. Sci. USA* 95, 6448-53 (1998). "Amyloidosis" or "amyloid disease" or "amyloid-related disease" refers to a pathological condition characterized by the presence of amyloid fibers. "Amyloid" is a generic term referring to a group of diverse but specific protein deposits (intracellular or extracellular) which are seen in a number of different diseases. Though diverse in their occurrence, all amyloid deposits have common morphologic properties, stain with specific dyes (e.g., Congo red), and have a characteristic red-green birefringent appearance in polarized light after staining. They also share common ultrastructural features and common X-ray diffraction and infrared spectra.

Gelsolin is a calcium binding protein that binds to fragments and actin filaments. Mutations at position 187 (e.g., Asp→Asn; Asp→Tyr) of the protein result in a form of hereditary systemic amyloidosis, usually found in patients from Finland, as well as persons of Dutch or Japanese origin. In afflicted individuals, fibrils formed from gelsolin fragments (Agel), usually consist of amino acids 173-243 (68 kDa carboxyterminal fragment) and are deposited in blood vessels and basement membranes, resulting in corneal dystrophy and cranial neuropathy which progresses to peripheral neuropathy, dystrophic skin changes and deposition in other organs. (Kangas, H., et al Human Mol. Genet. 5(9): 1237-1243, 1996).

Other mutated proteins, such as mutant alpha chain of fibrinogen (AfibA) and mutant cystatin C (Acys) also form fibrils and produce characteristic hereditary disorders. AfibA fibrils form deposits characteristic of a nonneuropathic hereditary amyloid with renal disease; Acys deposits are characteristic of a hereditary cerebral amyloid angiopathy reported in Iceland (Isselbacher, Harrison's Principles of Internal Medicine, McGraw-Hill, San Francisco, 1995; Benson, et al). In at least some cases, patients with cerebral amyloid angiopathy (CAA) have been shown to have amyloid fibrils containing a non-mutant form of cystatin C in conjunction with amyloid beta protein (Nagai, A., et al. Molec. Chem. Neuropathol. 33: 63-78, 1998).

Certain forms of prion disease are now considered to be heritable, accounting for up to 15% of cases, which were previously thought to be predominantly infectious in nature. (Baldwin, et al., in Research Advances in *Alzheimer's Disease and Related Disorders*, John Wiley and Sons, New York, 1995). In hereditary and sporadic prion disorders, patients develop plaques composed of abnormal isoforms of the normal prion protein (PrP$^{Sc}$).

A predominant mutant isoform, PrP$^{Sc}$, also referred to as AScr, differs from the normal cellular protein in its resistance to protease degradation, insolubility after detergent extraction, deposition in secondary lysosomes, post-translational synthesis, and high β-pleated sheet content. Genetic linkage has been established for at least five mutations resulting in Creutzfeldt-Jakob disease (CJD), Gerstmann-Sträussler-Scheinker syndrome (GSS), and fatal familial insomnia (FFI). (Baldwin, supra) Methods for extracting fibril peptides from scrapie fibrils, determining sequences and making such peptides are known in the art (e.g., Beekes, M., et al. J. Gen. Virol. 76: 2567-76, 1995).

For example, one form of GSS has been linked to a PrP mutation at codon 102, while telencephalic GSS segregates with a mutation at codon 117. Mutations at codons 198 and 217 result in a form of GSS in which neuritic plaques characteristic of Alzheimer's disease contain PrP instead of Aβ peptide. Certain forms of familial CJD have been associated with mutations at codons 200 and 210; mutations at codons 129 and 178 have been found in both familial CJD and FFI. (Baldwin, supra).

Cerebral Amyloidosis

Local deposition of amyloid is common in the brain, particularly in elderly individuals. The most frequent type of amyloid in the brain is composed primarily of Aβ peptide fibrils, resulting in dementia or sporadic (non-hereditary) Alzheimer's disease. The most common occurrences of cerebral amyloidosis are sporadic and not familial. For example, the incidence of sporadic Alzheimer's disease and sporadic CAA greatly exceeds the incidence of familial AD and CAA. Moreover, sporadic and familial forms of the disease cannot be distinguished from each other (they differ only in the presence or absence of an inherited genetic mutation); for example, the clinical symptoms and the amyloid plaques formed in both sporadic and familial AD are very similar, if not identical.

Cerebral amyloid angiopathy (CAA) refers to the specific deposition of amyloid fibrils in the walls of leptomingeal and cortical arteries, arterioles and veins. It is commonly associated with Alzheimer's disease, Down's syndrome and normal aging, as well as with a variety of familial conditions related to stroke or dementia (see Frangione et al., Amyloid; J. Protein Folding Disord. 8, Suppl. 1, 36-42 (2001)). CAA can occur sporadically or be hereditary.

Senile Systemic Amyloidosis

Amyloid deposition, either systemic or focal, increases with age. For example, fibrils of wild type transthyretin (TTR) are commonly found in the heart tissue of elderly individuals. These may be asymptomatic, clinically silent, or may result in heart failure. Asymptomatic fibrillar focal deposits may also occur in the brain (Aβ), corpora amylacea of the prostate (β$_2$ microglobulin), joints and seminal vesicles.

Dialysis-related Amyloidosis (DRA)

Plaques composed of β$_2$ microglobulin (β$_2$M) fibrils commonly develop in patients receiving long term hemodialysis or peritoneal dialysis. β$_2$ microglobulin is a 11.8 kiloDalton polypeptide and is the light chain of Class I MHC antigens, which are present on all nucleated cells. Under normal circumstances, $\beta_2M$ is usually distributed in the extracellular space unless there is an impaired renal function, in which case $\beta_2M$ is transported into tissues where it polymerizes to form amyloid fibrils. Failure of clearance such as in the case of impaired renal function, leads to deposition in the carpal tunnel and other sites primarily in collagen-rich tissues of the joints). Unlike other fibril proteins, $\beta_2M$ molecules are not produced by cleavage of a longer precursor protein and are generally present in unfragmented form in the fibrils. (Benson, supra). Retention and accumulation of this amyloid precursor has been shown to be the main pathogenic process underlying DRA. DRA is characterized by peripheral joint osteoarthropathy (e.g., joint stiffness, pain, swelling, etc.). Isoforms of $\beta_2M$, glycated $\beta_2M$, or polymers of $\beta_2M$ in tissue are the most amyloidogenic form (as opposed to native $\beta_2M$). Unlike other types of amyloidosis, $\beta_2M$ is confined largely to osteoarticular sites. Visceral depositions are rare. Occasionally, these deposits may involve blood vessels and other important anatomic sites.

Despite improved dialysis methods for removal of $\beta_2M$, the majority of patients have plasmatic $\beta_2M$ concentrations that remain dramatically higher than normal. These elevated $\beta_2M$ concentrations generally lead to Diabetes-Related Amyloidosis (DRA) and cormorbidities that contribute to mortality.

Islet Amyloid Polypeptide and Diabetes

Islet hyalinosis (amyloid deposition) was first described over a century ago as the presence of fibrous protein aggregates in the pancreas of patients with severe hyperglycemia (Opie, E L., *J Exp. Med.* 5:397-428, 1901). Today, islet amyloid, composed predominantly of islet amyloid polypeptide (IAPP), or amylin, is a characteristic histopathological marker in over 90% of all cases of Type II diabetes (also known as Non-Insulin Dependent Diabetes, or NIDDM). These fibrillar accumulations result from the aggregation of the islet amyloid polypeptide (IAPP) or amylin, which is a 37 amino acid peptide, derived from a larger precursor peptide, called pro-IAPP.

IAPP is co-secreted with insulin in response to β-cell secretagogues. This pathological feature is not associated with insulin-dependent (Type I) diabetes and is a unifying characteristic for the heterogeneous clinical phenotypes diagnosed as NIDDM (Type II diabetes).

Longitudinal studies in cats and immunocytochemical investigations in monkeys have shown that a progressive increase in islet amyloid is associated with a dramatic decrease in the population of insulin-secreting O-cells and increased severity of the disease. More recently, transgenic studies have strengthened the relationship between IAPP plaque formation and β-cell apoptosis and dysfunction, indicating that amyloid deposition is a principal factor in increasing severity of Type II diabetes.

IAPP has also been shown to induce β-islet cell toxicity in vitro, indicating that appearance of IAPP fibrils in the pancreas of Type II or Type I diabetic patients (post-islet transplantation) could contribute to the loss of the β-cell islets (Langerhans) and organ dysfunction. In patients with Type II diabetes, the accumulation of pancreatic IAPP leads to formation of oligomeric IAPP, leading to a buildup of IAPP-amyloid as insoluble fibrous deposits which eventually destroys the insulin-producing β cells of the islet, resulting in β cell depletion and failure (Westermark, P., Grimelius, L., *Acta Path. Microbiol. Scand, sect A.* 81: 291-300, 1973; de Koning, E J P., et al, *Diabetologia* 36: 378-384, 1993; and Lorenzo, A., et al., *Nature* 368: 756-760, 1994). Accumulation of IAPP as fibrous deposits can also have an impact on the ratio of pro-IAPP to IAPP normally found in plasma by increasing this ratio due to the trapping of IAPP in deposits. Reduction of β cell mass can be manifested by hyperglycemia and insulinemia. This β-cell mass loss can lead to a need for insulin therapy.

Diseases caused by the death or malfunctioning of a particular type or types of cells can be treated by transplanting into the patient healthy cells of the relevant type of cell. This approach has been used for Type I diabetes patients. Often pancreatic islet cells from a donor are cultured in vitro prior to transplantation, to allow them to recover after the isolation procedure or to reduce their immunogenicity. However, in many instances islet cell transplantation is unsuccessful, due to death of the transplanted cells. One reason for this poor success rate is IAPP, which organizes into toxic oligomers. Toxic effects may result from intracellular and extracellular accumulation of fibril oligomers. The IAPP oligomers can form fibrils and become toxic to the cells in vitro. In addition, IAPP fibrils are likely to continue to grow after the cells are transplanted and cause death or dysfunction of the cells. This may occur even when the cells are from a healthy donor and the patient receiving the transplant does not have a disease that is characterized by the presence of fibrils. For example, compounds of the present invention may also be used in preparing tissues or cells for transplantation according to the methods described in International Patent Application (PCT) number WO 01/003680.

The compounds of the invention may also stabilize the ratio of the concentrations of Pro-IAPP/IAPP, pro-Insulin/Insulin and C-peptide levels. In addition, as biological markers of efficacy, the results of the different tests, such as the arginine-insulin secretion test, the glucose tolerance test, insulin tolerance and sensitivity tests, could all be used as markers of reduced β-cell mass and/or accumulation of amyloid deposits. Such class of drugs could be used together with other drugs targeting insulin resistance, hepatic glucose production, and insulin secretion. Such compounds might prevent insulin therapy by preserving β-cell function and be applicable to preserving islet transplants.

Hormone-derived Amyloidoses

Endocrine organs may harbor amyloid deposits, particularly in aged individuals. Hormone-secreting tumors may also contain hormone-derived amyloid plaques, the fibrils of which are made up of polypeptide hormones such as calcitonin (medullary carcinoma of the thyroid), and atrial natriuretic peptide (isolated atrial amyloidosis). Sequences and structures of these proteins are well known in the art.

Miscellaneous Amyloidoses

There are a variety of other forms of amyloid disease that are normally manifest as localized deposits of amyloid. In general, these diseases are probably the result of the localized production or lack of catabolism of specific fibril precursors or a predisposition of a particular tissue (such as the joint) for fibril deposition. Examples of such idiopathic deposition include nodular AL amyloid, cutaneous amyloid, endocrine amyloid, and tumor-related amyloid. Other amyloid-related diseases include those described in Table 1, such as familial amyloid polyneuropathy (FAP), senile systemic amyloidosis, Tenosynovium, familial amyloidosis, Ostertag-type, non-neuropathic amyloidosis, cranial neuropathy, hereditary cerebral hemorrhage, familial dementia, chronic dialysis, familial Creutzfeldt-Jakob disease; Gerstmann-Sträussler-Scheinker syndrome, hereditary spongiform encephalopathies, prion diseases, familial Mediterranean fever, Muckle-Well's syndrome, nephropathy, deafness, urticaria, limb pain, cardiomyopathy, cutaneous deposits, multiple myeloma, benign monoclonal gammopathy, maccoglobulinaemia, myeloma associated amyloidosis, medullary carcinomas of the thyroid, isolated atrial amyloid, and diabetes.

The compounds of the invention may be administered therapeutically or prophylactically to treat diseases associated with amyloid fibril formation, aggregation or deposition, regardless of the clinical setting. The compounds of the invention may act to ameliorate the course of an amyloid-related disease using any of the following mechanisms, such as, for example but not limited to: slowing the rate of amyloid fibril formation or deposition; lessening the degree of amyloid deposition; inhibiting, reducing, or preventing amyloid fibril formation; inhibiting amyloid induced inflammation; enhancing the clearance of amyloid from, for example, the brain; or protecting cells from amyloid induced (oligomers or fibrillar) toxicity.

In an embodiment, the compounds/formulations of the invention may be administered therapeutically or prophylactically to treat diseases associated with amyloid-β fibril formation, aggregation or deposition. The compounds of the invention may act to ameliorate the course of an amyloid-β related disease using any of the following mechanisms (this list is meant to be illustrative and not limiting): slowing the rate of amyloid-β fibril formation or deposition; lessening the degree of amyloid-β deposition; inhibiting, reducing, or preventing amyloid-β fibril formation; inhibiting neurodegeneration or cellular toxicity induced by amyloid-β; inhibiting amyloid-β induced inflammation; enhancing the clearance of amyloid-β from the brain; or favoring greater catabolism of Aβ.

Compounds of the invention may be effective in controlling amyloid-β deposition either following their entry into the brain (following penetration of the blood brain barrier) or from the periphery. When acting from the periphery, a compound may alter the equilibrium of Aβ between the brain and the plasma so as to favor the exit of Aβ from the brain. An increase in the exit of Aβ from the brain would result in a decrease in Aβ brain concentration and therefore favor a decrease in Aβ deposition. In addition, compounds that penetrate the brain may control deposition by acting directly on brain Aβ, e.g., by maintaining it in a non-fibrillar form or favoring its clearance from the brain. The compounds may slow down APP processing; may increase degradation of Aβ fibrils by macrophages or by neuronal cells; or may decrease Aβ production by activated microglia. These compounds could also prevent Aβ in the brain from interacting with the cell surface and therefore prevent neurotoxicity, neurodegeneration, or inflammation.

In a preferred embodiment, the method is used to treat Alzheimer's disease (e.g., sporadic or familial AD). The method can also be used prophylactically or therapeutically to treat other clinical occurrences of amyloid-β deposition, such as in Down's syndrome individuals and in patients with cerebral amyloid angiopathy ("CAA"), hereditary cerebral hemorrhage, or early Alzheimer's disease.

In another embodiment, the method is used to treat mild cognitive impairment. Mild Cognitive Impairment ("MCI") is a condition characterized by a state of mild but measurable impairment in thinking skills, which is not necessarily associated with the presence of dementia. MCI frequently, but not necessarily, precedes Alzheimer's disease.

Additionally, abnormal accumulation of APP and of amyloid-β protein in muscle fibers has been implicated in the pathology of sporadic inclusion body myositis (IBM) (Askanas, V., et al. (1996) *Proc. Natl. Acad. Sci. USA* 93; 1314-1319; Askanas, V. et al. (1995) *Current Opinion in Rheumatology* 7: 486-496). Accordingly, the compounds of the invention can be used prophylactically or therapeutically in the treatment of disorders in which amyloid-beta protein is abnormally deposited at non-neurological locations, such as treatment of IBM by delivery of the compounds to muscle fibers.

Additionally, it has been shown that Aβ is associated with abnormal extracellular deposits, known as drusen, that accumulate along the basal surface of the retinal pigmented epithelium in individuals with age-related macular degeneration (ARMD). ARMD is a cause of irreversible vision loss in older individuals. It is believed that Aβ deposition could be an important component of the local inflammatory events that contribute to atrophy of the retinal pigmented epithelium, drusen biogenesis, and the pathogenesis of ARMD (Johnson, et al, Proc. Natl. Acad. Sci. USA 99(18), 11830-5 (2002)).

In another embodiment, the invention also relates to a method of treating or preventing an amyloid-related disease in a subject (preferably a human) comprising administering to the subject a therapeutic amount of a compound according to the following Formulae or otherwise described herein, such that amyloid fibril formation or deposition, neurodegeneration, or cellular toxicity is reduced or inhibited. In another embodiment, the invention relates to a method of treating or preventing an amyloid-related disease in a subject (preferably a human) comprising administering to the subject a therapeutic amount of a compound according to the following Formulae or otherwise described herein, such that cognitive function is improved or stabilized or further deterioration in cognitive function is prevented, slowed, or stopped in patients with brain amyloidosis, e.g., Alzheimer's disease, Down's syndrome or cerebral amyloid angiopathy. These compounds can also improve quality of daily living in these subjects.

The therapeutic compounds of the invention may treat amyloidosis related to type II diabetes by, for example, stabilizing glycemia, preventing or reducing the loss of β cell mass, reducing or preventing hyperglycemia due to loss of β cell mass, and modulating (e.g., increasing or stabilizing) insulin production. The compounds of the invention may also stabilize the ratio of the concentrations of pro-IAPP/IAPP.

The therapeutic compounds of the invention may treat AA (secondary) amyloidosis and/or AL (primary) amyloidosis, by stabilizing renal function, decreasing proteinuria, increasing creatinine clearance (e.g., by at least 50% or greater or by at least 100% or greater), or by leading to remission of chronic diarrhea, or weight gain (e.g., 10% or greater).

II. Methods of the Invention

In one embodiment, the invention includes a method for inhibiting amyloid deposition in a subject comprising administering to the subject an effective amount of a therapeutic formulation comprising a therapeutic compound as described herein, such that amyloid deposition is inhibited. Accordingly, in another embodiment, the invention pertains to a method of treating or preventing an amyloid-related disease, e.g., Aβ-related disease, in a subject comprising administering to a subject a therapeutic amount of a therapeutic formulation comprising a therapeutic compound of the invention.

The formulations of the invention may be administered therapeutically or prophylactically to treat diseases associated with amyloid-β fibril formation, aggregation or deposition. The formulations of the invention may act to ameliorate the course of an amyloid-β related disease using any of the following mechanisms (this list is meant to be illustrative and not limiting): slowing the rate of amyloid-β fibril formation or deposition; lessening the degree of amyloid-β deposition; inhibiting, reducing, or preventing amyloid-β fibril formation; inhibiting neurodegeneration or cellular toxicity induced by amyloid-β; inhibiting amyloid-β induced inflammation; or enhancing the clearance of amyloid-β from the brain.

The formulations of the invention may be effective in controlling amyloid-β deposition either following their entry into the brain (following penetration of the blood brain barrier) or from the periphery. Without wishing to be bound by theory, when acting from the periphery, the compound of a formulation of the invention may alter the equilibrium of Aβ between the brain and the plasma so as to favor the exit of Aβ from the brain. An increase in the exit of Aβ from the brain would result in a decrease in Aβ brain concentration and therefore favor a decrease in Aβ deposition. Alternatively, the compounds of a formulation of the invention that penetrate the brain could control deposition by acting directly on brain Aβ, e.g., by maintaining it in a non-fibrillar form or favoring its clearance from the brain, or protecting brain cells from the detrimental effect of Aβ. In another embodiment, the compound may also prevent the amyloid protein, in its soluble, oligomeric form or in its fibrillar form, from binding or adhering to a cell surface and causing cell damage or toxicity.

In a particular embodiment, the method is used to treat Alzheimer's disease (e.g., sporadic or familial AD). The method can also be used prophylactically or therapeutically to treat other clinical occurrences of amyloid-β deposition, such as in Down's syndrome individuals and in patients with cerebral amyloid angiopathy ("CAA") or hereditary cerebral hemorrhage.

In certain embodiments, the therapeutic formulation of the invention is capable of inhibiting an interaction between an amyloidogenic protein and a constituent of a basement membrane, e.g., a glycoprotein or a proteoglycan, to thus inhibit amyloid deposition. The ability of a therapeutic compound of the invention to inhibit an interaction between an amyloidogenic protein and a glycoprotein or proteoglycan constituent of a basement membrane can be assessed by an in vitro binding assay, such as the mass spectroscopy assay described herein (Example 5) or in U.S. Pat. No. 5,164,295, which is hereby expressly incorporated herein by reference in its entirety.

The present invention relates to a method for inhibiting amyloid deposition in a subject comprising administering to the subject an effective amount of a therapeutic formulation as described herein, the therapeutic formulation comprising a therapeutic compound that comprises at least one sulfonate group covalently attached to a substituted or unsubstituted aromatic or aliphatic molecule.

In another embodiment, the invention includes a method for inhibiting the binding of a chemokine to a glycosaminoglycan comprising administering a therapeutic formulation comprising a therapeutic compound as described herein.

In yet another embodiment, the invention relates to a method for modulating interaction between a bacterium and a glycosaminoglycan in a human comprising administering to the human a therapeutic formulation comprising a therapeutic compound as described herein. Accordingly, the present invention also pertains to a method for treating a bacterial infection in a human, the method comprising administering to the human a therapeutic formulation comprising a therapeutic compound of the invention. In a specific embodiment, the invention is a method for treating a subject afflicted with *Chlamydia* comprising administering to the subject a therapeutic formulation comprising a therapeutic compound as described herein In an additional embodiment, the invention includes a method for modulating interaction between a virus and a glycosaminoglycan in a subject comprising administering to the subject a therapeutic formulation comprising a therapeutic compound as described herein. More generally, another embodiment of the invention is a method for treating a viral infection in a subject comprising administering to the subject a therapeutic formulation comprising a therapeutic compound of the invention. In a specific embodiment, the invention is a method for treating a subject afflicted with HSV comprising administering to the subject a therapeutic formulation comprising a therapeutic compound as described herein.

Additionally, one embodiment of the invention is a method for reducing amyloid deposits in a subject having amyloid deposits, the method comprising administering to the subject an effective amount of a therapeutic formulation comprising a therapeutic compound as described herein, such that amyloid deposits are reduced in the subject.

Another embodiment of the invention pertains to a method of preventing, treating or inhibiting cerebral amyloid angiopathy in a subject, comprising administering a therapeutic formulation comprising a therapeutic compound of the invention to the subject. Furthermore, the invention includes a method of preventing, treating, or inhibiting cerebral amyloid angiopathy, comprising contacting a blood vessel wall cell with a therapeutic formulation comprising a therapeutic compound of the invention, such that cerebral amyloid angiopathy is prevented, treated, or inhibited. In addition, the invention includes a method of preventing, treating, or inhibiting cerebral amyloid angiopathy, comprising contacting a blood vessel wall cell with a therapeutic compound of a therapeutic formulation of the invention, such that cerebral amyloid angiopathy is prevented, treated, or inhibited.

The language "inhibition of amyloid deposition" includes reducing, preventing or stopping of amyloid formation, e.g., fibrillogenesis, inhibiting or slowing down of further amyloid deposition in a subject with amyloidosis, e.g., already having amyloid deposits, and reducing or reversing amyloid fibrillogenesis or deposits in a subject with ongoing amyloidosis. For example, the extent of the inhibition of amyloid deposition is contemplated by the instant application as a range, which can include, for example, substantially complete elimination of amyloid deposition or reduction of amyloid deposition. Inhibition of amyloid deposition is determined relative to an untreated subject, or relative to the treated subject prior to treatment, or, e.g., determined by clinically measurable improvement in pancreatic function in a diabetic patient, or in the case of a patient with brain amyloidosis, e.g., an Alzheimer's or cerebral amyloid angiopathy patient, stabilization of cognitive function or prevention of a further decrease in cognitive function (i.e., preventing, slowing, or stopping disease progression), or improvement of parameters such as the concentration of Aβ or tau in the CSF. In certain embodiments, amyloid deposition may be inhibited by, for example, inhibiting an interaction between an amyloidogenic protein and a constituent of basement membrane, enhancing clearance of amyloid β from the brain, or inhibiting neurodegeneration or cellular toxicity induced by amyloid (e.g., by soluble or insoluble amyloid, e.g., fibrils, by amyloid deposition and/or by amyloid-β, as described herein), or protecting brain cells from the detrimental effect of Aβ.

The language "basement membrane" refers to an extracellular matrix comprising glycoproteins and proteoglycans, including laminin, collagen type IV, fibronectin, agrin, perlecan, and heparan sulfate proteoglycan (HSPG). In one embodiment, amyloid deposition is inhibited by interfering with an interaction between an amyloidogenic protein and a sulfated glycosaminoglycan such as HSPG. Sulfated glycosaminoglycans are known to be present in all types of amyloids (see Snow, A. D., et al. Lab. Invest. 56, 120-123 (1987)) and amyloid deposition and HSPG deposition occur coincidentally in animal models of amyloidosis (see Snow, A. D., et al., Lab. Invest. 56, 665-675 (1987)).

As used herein, "treatment" of a subject includes the application or administration of a composition of the invention to a subject, or application or administration of a composition of the invention to a cell or tissue from a subject, who has a amyloid-related disease or condition, has a symptom of such a disease or condition, or is at risk of (or susceptible to) such a disease or condition, with the purpose of curing, healing, alleviating, relieving, altering, remedying, ameliorating, improving, or affecting the disease or condition, the symptom of the disease or condition, or the risk of (or susceptibility to) the disease or condition. The term "treating" refers to any indicia of success in the treatment or amelioration of an injury, pathology or condition, including any objective or subjective parameter such as abatement; remission; diminishing of symptoms or making the injury, pathology or condition more tolerable to the subject; slowing in the rate of degeneration or decline; making the final point of degeneration less debilitating; improving a subject's physical or mental well-being; or, in some situations, preventing the onset of dementia. The treatment or amelioration of symptoms can be based on objective or subjective parameters; including the results of a physical examination, a psychiatric evaluation, or a cognition test such as Clinical Dementia Rating (CDR) scale, Mini-mental State Examination (MMSE), Alzheimer's Disease Assessment Scale-Cognitive Subscale (ADAS-Cog), or another test known in the art. For example, the methods of the invention successfully treat a subject's dementia by slowing the rate of or lessening the extent of cognitive decline.

In one embodiment, the term "treating" includes maintaining a subject's CDR rating at its base line rating or at 0. In another embodiment, the term treating includes decreasing a subject's CDR rating by about 0.25 or more, about 0.5 or more, about 1.0 or more, about 1.5 or more, about 2.0 or more, about 2.5 or more, or about 3.0 or more. In another embodiment, the term "treating" also includes reducing the rate of the increase of a subject's CDR rating as compared to historical controls. In another embodiment, the term includes reducing the rate of increase of a subject's CDR rating by about 5% or more, about 10% or more, about 20% or more, about 25% or more, about 30% or more, about 40% or more, about 50% or more, about 60% or more, about 70% or more, about 80% or more, about 90% or more, or about 100%, of the increase of the historical or untreated controls.

In another embodiment, the term "treating" also includes maintaining a subject's score on the MMSE. The term "treating" includes increasing a subject's MMSE score by about 1, about 2, about 3, about 4, about 5, about 7.5, about 10, about 12.5, about 15, about 17.5, about 20, or about 25 points. The term also includes reducing the rate of the decrease of a subject's MMSE score as compared to historical controls. In another embodiment, the term includes reducing the rate of decrease of a subject's MMSE score may be about 5% or less, about 10% or less, about 20% or less, about 25% or less, about 30% or less, about 40% or less, about 50% or less, about 60% or less, about 70% or less, about 80% or less, about 90% or less or about 100% or less, of the decrease of the historical or untreated controls.

In yet another embodiment, the term "treating" includes maintaining a subject's score on the ADAS-Cog. The term "treating" includes decreasing a subject's ADAS-Cog score by about 1 point or greater, by about 2 points or greater, by about 3 points or greater, by about 4 points or greater, by about 5 points or greater, by about 7.5 points or greater, by about 10 points or greater, by about 12.5 points or greater, by about 15 points or greater, by about 17.5 points or greater, by about 20 points or greater, or by about 25 points or greater. The term also includes reducing the rate of the increase of a subject's ADAS-Cog score as compared to historical controls. In another embodiment, the term includes reducing the rate of increase of a subject's ADAS-Cog score by about 5% or more, about 10% or more, about 20% or more, about 25% or more, about 30% or more, about 40% or more, about 50% or more, about 60% or more, about 70% or more, about 80% or more, about 90% or more or about 100% of the increase of the historical or untreated controls.

In another embodiment, the term "treating," for example, for AA or AL amyloidosis, includes an increase in serum creatinine clearance, e.g., an increase of creatinine clearance of 10% or greater, 20% or greater, 50% or greater, 80% or greater, 90% or greater, 100% or greater, 150% or greater, 200% or greater. The term "treating" also may include remission of nephrotic syndrome (NS). It may also include remission of chronic diarrhea and/or a gain in body weight, e.g., by 10% or greater, 15% or greater, or 20% or greater.

The term "prevention" or "preventing" is also used to describe the application or administration of a composition of the invention to a subject who is at risk of (or susceptible to) such a disease or condition. Patients amenable to treatment for prevention of the disease or condition include individuals at risk of the disease or condition but not showing symptoms, as well as patients presently showing symptoms. In the case of Alzheimers disease, virtually anyone is at risk of suffering from Alzheimer's disease if he or she lives long enough. Therefore, the present methods can be administered prophylactically to the general population without any assessment of the risk of the subject patient. But the present methods are especially useful for individuals who do have a known risk of Alzheimer's disease. Such individuals include those having relatives who have experienced this disease, and those whose risk is determined by analysis of genetic or biochemical markers, including brain plaques diagnosed by imaging methods, e.g., MRI, PET, SPECT etc. Examples of such imaging methods are discussed in Burggren et al., *Current Topics in Medicinal Chemistry*, vol. 2002, no. 2, pp. 385-393, and Sair et al., *Neuroradiology*, vol. 46, pp. 93-104 (2002). Genetic markers of risk toward Alzheimer's disease include mutations in the APP gene, particularly mutations at position 717 and positions 670 and 671 referred to as the Hardy and Swedish mutations respectively (see Hardy et al., TINS 20, 154-158 (1997)). Other markers of risk are mutations in the presenilin genes, PS1 and PS2, and ApoE4, family history of AD, hypercholesterolemia or atherosclerosis. Individuals presently suffering from Alzheimer's disease can be recognized from characteristic dementia, as well as the presence of risk factors described above. In addition, a number of diagnostic tests based on cognitive and neurological testing are available for identifying individuals who have AD. For example, individuals suffering from Alzheimer's disease can be diagnosed by the Clinical Dementia Rating (CDR) scale, Mini-mental State Examination (MMSE), Alzheimer's Disease Assessment Scale-Cognitive Subscale (ADAS-Cog), or another test known in the alt, as discussed herein. Baseline scores on suitable metrics including the MMSE and the ADAS together with other metrics designed to evaluate a more normal population can be used to find an at risk population. Another method for identifying an at risk group utilizes an assay for neural thread protein in the urine; see, e.g., Munzar et al., *Neurology and Clinical Neurophysiology*, Vol. 2002, No. 1. Patients with high risk for Alzheimer's Disease can also be selected from a population by screening for early signs of memory loss or other difficulties associated with pre-Alzheimer's symptomatology, a family history of Alzheimer's Disease, patients with MCI, genetic risk factors, age, sex, and other features found to predict high-risk for Alzheimer's Disease.

Without wishing to be bound by theory, in some aspects the pharmaceutical compositions of the invention contain a compound that prevents or inhibits amyloid fibril formations either in the brain or other organ of interest (acting locally) or throughout the entire body (acting systemically). Pharmaceutical compositions of the invention may be effective in controlling amyloid deposition either following their entry into the brain (following penetration of the blood brain barrier) or from the periphery. When acting from the periphery, a compound of a pharmaceutical composition may alter the equilibrium of amyloidogenic peptide between the brain and the plasma to favor the exit of amyloidogenic peptide from the brain. It may also favor clearance (or catabolism) of the amyloid protein (soluble), and then prevent amyloid fibril formation and deposition due to a reduction of the amyloid protein pool in a specific organ, e.g., liver, spleen, pancreas, kidney, joints, brain, etc. An increase in the exit of amyloidogenic peptide from the brain would result in a decrease in amyloidogenic peptide brain concentration, and therefore, favor a decrease in amyloidogenic peptide deposition. In particular, an agent may lower the levels of amyloid β peptides, e.g., both Aβ40 and Aβ42 in the CSF and the plasma, or the agent may lower the levels of amyloid β peptides, e.g., Aβ40 and Aβ42 in the CSF and increase it in the plasma. Alternatively, compounds that penetrate the brain could control deposition by acting directly on brain amyloidogenic peptide e.g., by maintaining it in a non-fibrillar form or favoring its clearance from the brain, by increasing its degradation in the brain, or protecting brain cells from the detrimental effect of amyloidogenic peptide. An agent can also cause a decrease of the concentration of the amyloid protein (i.e., in a specific organ so that the critical concentration needed to trigger amyloid fibril formation or deposition is not reached). Furthermore, the compounds described herein may inhibit or reduce an interaction between amyloid and a cell surface constituent, for example, a glycosaminoglycan- or proteoglycan constituent of a basement membrane. The compounds may also prevent an amyloid peptide from binding or adhering to a cell surface, a process that is known to cause cell damage or toxicity. Similarly, the compounds may block amyloid-induced cellular toxicity or microglial activation or amyloid-induced neurotoxicity, or inhibit amyloid induced inflammation. The compounds may also reduce the rate or amount of amyloid aggregation, fibril formation, or deposition, or the compounds may lessen the degree of amyloid deposition. The foregoing mechanisms of action should not be construed as limiting the scope of the invention inasmuch as the invention may be practiced without such information.

The term "significantly," or "significant," is descriptive of the changes in an identified property that occur in noticeable or measurable amounts or increments, or where such changes would have a noticeable, measurable, or unacceptable impact, e.g., a detrimental impact. As such, the language "significantly reduce or prevent gastrointestinal intolerance" includes a noticeable or measurable reduction or prevention of gastrointestinal intolerance, i.e., as opposed to the situation where the reduction or prevention is not noticeable or measurable. For example, the number of incidents of nausea, vomiting, and gastrointestinal-associated pain or irritation tracked over time may be used as a measure of the impact of the therapeutic formulations of the present invention on the reduction or prevention of gastrointestinal intolerance. Additionally, the language "do not significantly affect the ability of the therapeutic formulation" is descriptive of items that affect the ability of the therapeutic formulation, but do not affect the ability in an unacceptable manner to the extent that the cost outweighs the benefit, and therefore do not "significantly affect" the ability of the therapeutic formulation.

"Modulation of amyloid deposition" includes both inhibition, as defined above, and enhancement of amyloid deposition or fibril formation. The term "modulating" is intended, therefore, to encompass 1) prevention or stopping of amyloid formation or accumulation, inhibition or slowing down of further amyloid aggregation in a subject with ongoing amyloidosis, e.g., already having amyloid aggregates, and reducing or reversing of amyloid aggregates in a subject with ongoing amyloidosis, and 2) enhancing amyloid deposition, e.g., increasing the rate or amount of amyloid deposition in vivo or in vitro. Amyloid-enhancing compounds may be useful in animal models of amyloidosis, for example, to make possible the development of amyloid deposits in animals in a shorter period of time or to increase amyloid deposits over a selected period of time. Amyloid-enhancing compounds may be useful in screening assays for compounds which inhibit amyloidosis in vivo, for example, in animal models, cellular assays and in vitro assays for amyloidosis. Such compounds may be used, for example, to provide faster or more sensitive assays for compounds. Modulation of amyloid aggregation is determined relative to an untreated subject or relative to the treated subject prior to treatment.

The term "therapeutic formulation" includes formulations that perform their intended therapeutic function, e.g., prevent, treat or inhibit amyloidosis, and are used to reduce or prevent gastrointestinal intolerance (i.e. nausea and vomiting). The reduction or prevention of gastrointestinal intolerance may, for example, depend on direct physical interaction in the stomach or indirect central action on the Central Nervous System.

In certain embodiments, the reduction or prevention of the gastrointestinal intolerance is at least dependent upon the therapeutic compound administered to the subject. In one embodiment, the therapeutic compound having a desirable therapeutic function is selected for inclusion in the therapeutic formulation based on its ability to reduce or prevent gastrointestinal intolerance. In certain embodiments, the compound is modified in order to produce a therapeutic compound having a desirable therapeutic function and an ability to reduce or prevent gastrointestinal intolerance. For example, the compound may be structurally modified (e.g., adding appropriate substituents or altering the pharmaceutically acceptable counter ion) or reformulated such that the compound has a desirable therapeutic function and an ability to reduce or prevent gastrointestinal intolerance.

In certain other embodiments, the reduction or prevention of the gastrointestinal intolerance is not dependent upon the therapeutic compound administered to the subject alone. For example, in one embodiment, the reduction or prevention of the gastrointestinal intolerance is not dependent upon the therapeutic compound having the formula 3-amino-1-propanesulfonate/X, where X is a counter cation or forms an ester with the sulfonate, e.g. 3-amino-1-propanesulfonic acid, or the sodium salt thereof. In a particular embodiment of the invention, the reduction or prevention of the gastrointestinal intolerance is dependent on an additional agent, such as enteric-coating or a modified-release agent.

In another embodiment, at least one additional agent is included in the therapeutic formulation, where the additional agent differs from the therapeutic compound. In a specific embodiment, the additional agent imparts at least one desirable property to the therapeutic formulation. In a particular embodiment, the desirable property, at least in part, reduces or prevents gastrointestinal intolerance. Accordingly, in an additional embodiment, an additional agent may be used in the therapeutic formulation to reduce or prevent gastrointestinal intolerance independently or in conjunction with other methods of reducing or preventing intolerance. For example, to protect against any possible gastrointestinal intolerance that could result from the therapeutic formulation, the tablets may be enteric-coated or a modified-release agent may be added to control any rapid release of the therapeutic compound in the stomach or intestine.

In one embodiment of the invention, the reduction or prevention of gastrointestinal intolerance is accomplished by the reduction or prevention of a local irritation as a result of high pH generated during the dissolution of therapeutic compound in the stomach subsequent to the administration of the therapeutic compound. As an additional advantage of the therapeutic formulations of the present invention, the reduction in gastrointestinal intolerance also leads to improved compliance by subjects of administration, e.g., patients.

In another particular embodiment, the therapeutic compound of the invention is an alkylsulfonic acid. The term "alkylsulfonic acid" includes substituted or unsubstituted alkylsulfonic acids, and substituted or unsubstituted lower alkylsulfonic acids. Amino-substituted compounds are especially noteworthy and the invention pertains to substituted- or unsubstituted-amino-substituted alkylsulfonic acids, and substituted- or unsubstituted-amino-substituted lower alkylsulfonic acids, an example of which is 3-amino-1-propanesulfonic acid. Also, it should be noted that the term "alkylsulfonic acid" as used herein is to be interpreted as being synonymous with the term "alkanesulfonic acid."

In certain embodiments, the invention pertains to a substituted or unsubstituted alkylsulfonic acid, substituted or unsubstituted alkylsulfuric acid, substituted or unsubstituted alkylthiosulfonic acid, substituted or unsubstituted alkylthiosulfuric acid, or an ester or amide thereof, including pharmaceutically acceptable salts thereof. For example, the invention relates to a compound that is a substituted or unsubstituted alkylsulfonic acid, or an ester or amide thereof, including pharmaceutically acceptable salts thereof. In another embodiment, the invention pertains to a compound that is a substituted or unsubstituted lower alkylsulfonic acid, or an ester or amide thereof, including pharmaceutically acceptable salts thereof. Similarly, the invention includes a compound that is a (substituted- or unsubstituted-amino)-substituted alkylsulfonic acid, or an ester or amide thereof, including pharmaceutically acceptable salts thereof. In yet another embodiment, the compound is a (substituted- or unsubstituted-amino)-substituted lower alkylsulfonic acid, or an ester or amide thereof, including pharmaceutically acceptable salts thereof.

Compositions of alkylsulfonic acids, including, for example, 3-amino-1-propanesulfonic acid and certain salts thereof have been shown to be useful in the treatment of amyloid-β related diseases, including Alzheimer's disease and cerebral amyloid angiopathy. See WO 96/28187, WO 01/85093, and U.S. Pat. No. 5,840,294.

One group of example alkylsulfonic acids have the following structure

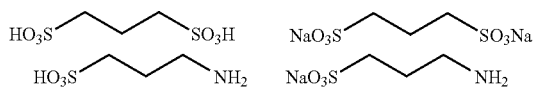

where Y is either an amino group (having the formula —$NR^aR^b$ wherein $R^a$ and $R^b$ are each independently hydrogen, alkyl, aryl, or heterocyclyl, or $R^a$ and $R^b$, taken together with the nitrogen atom to which they are attached, form a cyclic moiety having from 3 to 8 atoms in the ring) or a sulfonic acid group (having the formula —$SO_3^-X^+$), n is an integer from 1 to 5, and X is hydrogen or a cationic group (e.g., sodium). Some exemplary alkylsulfonic acids include the following $$HO_3S\frown\frown SO_3H \qquad NaO_3S\frown\frown SO_3Na$$
$$HO_3S\frown\frown NH_2 \qquad NaO_3S\frown\frown NH_2$$

Alkylsulfonic acids may be prepared by the methods illustrated in the general reaction schemes as, for example, described in U.S. Pat. Nos. 5,643,562; 5,972,328; 5,728,375; 5,840,294; 4,657,704; and the U.S. provisional patent application No. 60/482,058, filed Jun. 23, 2003, U.S. provisional patent application No. 60/512,135, filed Oct. 17, 2003, both entitled Synthetic Process for Preparing Compounds for Treating Amyloidosis, and U.S. application Ser. No. 10/871,543, filed Jun. 18, 2004, identified by published as WO 2004/11391 and entitled Improved Pharmaceutical Drug Candidates and Method for Preparation Thereof, the contents of which are hereby expressly incorporated by reference in their entireties, or by modifications thereof; using readily available starting materials, reagents and conventional synthesis procedures. In these reactions, it is also possible to make use of variants which are in themselves known, but are not mentioned. For example, functional and structural equivalents of the compounds described herein and which have the same general properties, (wherein one or more simple variations of substituents are made that do not adversely affect the essential nature or the utility of the compound) may be prepared according to a variety of methods known in the art.

In general, the compounds of the present invention may be prepared by the methods illustrated in the general reaction schemes as, for example, described below, or by modifications thereof, e.g., using readily available starting materials, reagents and conventional synthesis procedures. In these reactions, it is also possible to make use of variants which are in themselves known, but are not mentioned here. Functional and structural equivalents of the agents described herein and that have the same general properties, wherein one or more simple variations of substituents are made which do not adversely affect the essential nature or the utility of the compound. The agents of the present invention may be readily prepared in accordance with the synthesis schemes and protocols described herein, as illustrated in the specific procedures provided. However, those skilled in the art will recognize that other synthetic pathways for forming the agents of this invention may be used, and that the following is provided merely by way of example, and is not limiting to the present invention. See, e.g., "Comprehensive Organic Transformations" by R. Larock, VCH Publishers (1989). It will be further recognized that various protecting and deprotecting strategies will be employed that are standard in the art (See, e.g., "Protective Groups in Organic Synthesis" by Greene and Wuts). Those skilled in the relevant arts will recognize that the selection of any particular protecting group (e.g., amine and carboxyl protecting groups) will depend on the stability of the protected moiety with regards to the subsequent reaction conditions and will understand the appropriate selections. Further illustrating the knowledge of those skilled in the art is the following sampling of the extensive chemical literature: "Chemistry of the Amino Acids" by J. P. Greenstein and M. Winitz, John Wiley & Sons, Inc., New York (1961); "Comprehensive Organic Transformations" by R. Larock, VCH Publishers (1989); T. D. Ocain, et al., J. Med. Chem. 31, 2193-99 (1988); E. M. Gordon, et al, J. Med. Chem. 31, 2199-10 (1988); "Practice of Peptide Synthesis" by M. Bodansky and A. Bodanszky, Springer-Verlag, New York (1984); "Protective Groups in Organic Synthesis" by T. Greene and P. Wuts (1991); "Asymmetric Synthesis: Construction of Chiral Molecules Using Amino Acids" by G. M. Coppola and H. F. Schuster, John Wiley & Sons, Inc., New York (1987); "The Chemical Synthesis of Peptides" by J. Jones, Oxford University Press, New York (1991); and "Introduction of Peptide Chemistry" by P. D. Bailey, John Wiley & Sons, Inc., New York (1992).

The chemical structures herein are drawn according to the conventional standards known in the art. Thus, where an atom, such as a carbon atom, as drawn appears to have an unsatisfied valency, then that valency is assumed to be satisfied by a hydrogen atom even though that hydrogen atom is not necessarily explicitly drawn. The structures of some of the compounds of this invention include stereogenic carbon atoms. It is to be understood that isomers arising from such asymmetry (e.g., all enantiomers and diastereomers) are included within the scope of this invention unless indicated otherwise. That is, unless otherwise stipulated, any chiral carbon center may be of either (R)- or (S)-stereochemistry. Such isomers can be obtained in substantially pure form by classical separation techniques and by stereochemically-controlled synthesis. Furthermore, alkenes can include either the E- or Z-geometry, where appropriate. In addition, the compounds of the present invention may exist in unsolvated as well as solvated forms with acceptable solvents such as water, THF, ethanol, and the like, as well as polymorphic forms, e.g., including pseudopolymorphic forms. The term "solvate" represents an aggregate that comprises one or more molecules of a compound, with one or more molecules of a pharmaceutical solvent, such as water, ethanol, and the like.

Further examples of compounds that may be used as a compound according to the present invention include those described in the U.S. provisional patent application No. 60/480,906, filed Jun. 23, 2003, and U.S. provisional patent application no, 60/512,047, filed Oct. 17, 2003, U.S. application Ser. No. 10/871,514 (WO2004/113275), filed Jun. 18, 2004, and U.S. application Ser. No. 10/871,365 (WO 2005/0038117), filed Jun. 18, 2004, all entitled Methods and Compositions for Treating Amyloid-Related Diseases; and U.S. provisional patent application No. 60/480,928, also filed 23 Jun. 2003, U.S. provisional patent application No. 60/512,018, filed Oct. 17, 2003, and U.S. application Ser. No. 10/871,512 (WO 2005/0038000), filed Jun. 18, 2004, all entitled Methods and Compositions for the Treatment of Amyloid- and Epileptogenesis-Associated Diseases.

In an embodiment, the invention pertains, at least in part to a composition having a therapeutic compound that is a compound of Formula I-A:

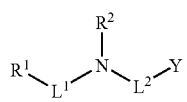

(I-A)

wherein:
R$^1$ is a substituted or unsubstituted cycloalkyl, aryl, arylcycloalkyl, bicyclic or tricyclic ring, a bicyclic or tricyclic fused ring group, or a substituted or unsubstituted C$_2$-C$_{10}$ alkyl group;
R$^2$ is selected from the group consisting of hydrogen, alkyl, mercaptoalkyl, alkenyl, alkynyl, cycloalkyl, aryl, arylalkyl, thiazolyl, triazolyl, imidazolyl, benzothiazolyl, and benzoimidazolyl;
Y is SO$_3^-$X$^+$, OSO$_3^-$X$^+$, or SSO$_3^-$X$^+$;
X$^+$ is hydrogen, a cationic group, or an ester forming group (i.e., as in a prodrug,); and
each of L$^1$ and L$^2$ is independently a substituted or unsubstituted C$_1$-C$_5$ alkyl group or absent, or a pharmaceutically acceptable salt thereof, provided that when R$^1$ is alkyl, L$^1$ is absent.

In another embodiment, the invention pertains, at least in part to a composition having a therapeutic compound that is a compound of Formula II-A:

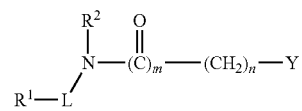

(II-A)

wherein:
R$^1$ is a substituted or unsubstituted cyclic, bicyclic, tricyclic, or benzoheterocyclic group or a substituted or unsubstituted C$_2$-C$_{10}$ alkyl group;
R$^2$ is hydrogen, alkyl, mercaptoalkyl, alkenyl, alkynyl, cycloalkyl, aryl, arylalkyl, thiazolyl, triazolyl, imidazolyl, benzothiazolyl, benzoimidazolyl, or linked to R$^1$ to form a heterocycle;
Y is SO$_3^-$X$^+$, OSO$_3^-$X$^+$, or SSO$_3^-$X$^+$;
X$^+$ is hydrogen, a cationic group, or an ester forming moiety;
m is 0 or 1;
n is 1, 2, 3, or 4;
L is substituted or unsubstituted C$_1$-C$_3$ alkyl group or absent, or a pharmaceutically acceptable salt thereof, provided that when R$^1$ is alkyl, L is absent. In a particular embodiment, n is 3 or 4.

In yet another embodiment, the invention pertains, at least in part to a composition having a therapeutic compound that is a compound of Formula III-A:

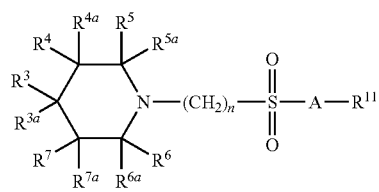

(III-A)

wherein:
A is nitrogen or oxygen;
R$^{11}$ is hydrogen, salt-forming cation, ester forming group, —(CH$_2$)$_x$-Q, or when A is nitrogen, A and R$^{11}$ taken together may be a natural or unnatural amino acid residue or a salt or ester thereof;
Q is hydrogen, thiazolyl, triazolyl, imidazolyl, benzothiazolyl, or benzoimidazolyl;
x is 0, 1, 2, 3, or 4;
n is 0, 1, 2, 3, 4, 5, 6, 7, 8, 9, or 10;

$R^3$, $R^{3a}$, $R^4$, $R^{4a}$, $R^5$, $R^{5a}$, $R^6$, $R^{6a}$, $R^7$ and $R^{7a}$ are each independently hydrogen, alkyl, mercaptoalkyl, alkenyl, alkynyl, cycloalkyl, aryl, alkylcarbonyl, arylcarbonyl, alkoxycarbonyl, cyano, halogen, amino, tetrazolyl, or two R groups on adjacent ring atoms taken together with the ring atoms form a double bond. In a particular embodiment, n is 3 or 4. In certain embodiments, one of $R^3$, $R^{3a}$, $R^4$, $R^{4a}$, $R^5$, $R^{5a}$, $R^6$, $R^{6a}$, $R^7$ and $R^{7a}$ is a moiety of Formula IIIa-A:

$$\text{(IIIa-A)}$$

wherein:

m is 0, 1, 2, 3, or 4;

$R^A$, $R^B$, $R^C$, $R^D$, and $R^E$ are independently selected from a group of hydrogen, halogen, hydroxyl, alkyl, alkoxyl, halogenated alkyl, mercaptoalkyl, alkenyl, alkynyl, cycloalkyl, aryl, cyano, thiazolyl, triazolyl, imidazolyl, tetrazolyl, benzothiazolyl, and benzoimidazolyl; and pharmaceutically acceptable salts and esters thereof. In certain embodiments, said compound is not 3-(4-phenyl-1,2,3,6-tetrahydro-1-pyridyl)-1-propanesulfonic acid.

An ester forming group or moiety includes groups, which when bound, form an ester. Examples of such groups include substituted or unsubstituted alkyl, aryl, alkenyl, alkynyl, or cycloalkyl. Particular examples of possible esters include methyl, ethyl, and t-butyl. Additionally, examples of salt forming cations include pharmaceutically acceptable salts described herein as well as lithium, sodium, potassium, magnesium, calcium, barium, zinc, iron, and ammonium. In a further embodiment, the salt forming cation is a sodium salt.

In yet another embodiment the invention pertains at least in part to a composition having a therapeutic compound that is a compound of Formula IV:

$$\text{(IV-A)}$$

wherein;

A is nitrogen or oxygen;

$R^{11}$ is hydrogen, salt-forming cation, ester forming group, —$(CH_2)_x$-Q, or when A is nitrogen, A and $R^{11}$ taken together may be a natural or unnatural amino acid residue or a salt or ester thereof;

Q is hydrogen, thiazolyl, triazolyl, imidazolyl, benzothiazolyl, or benzoimidazolyl;

x is 0, 1, 2, 3, or 4;

n is 0, 1, 2, 3, 4, 5, 6, 7, 8, 9, or 10;

$R^4$, $R^{4a}$, $R^5$, $R^{5a}$, $R^6$, $R^{6a}$, $R^7$, and $R^{7a}$ are each independently hydrogen, alkyl, mercaptoalkyl, alkenyl, alkynyl, cycloalkyl, aryl, alkylcarbonyl, arylcarbonyl, alkoxycarbonyl, cyano, halogen, amino, tetrazolyl, $R^4$ and $R^5$ taken together, with the ring atoms they are attached to, form a double bond, or $R^6$ and $R^7$ taken together, with the ring atoms they are attached to, form a double bond;

m is 0, 1, 2, 3, or 4;

$R^8$, $R^9$, $R^{10}$, $R^{11}$, and $R^{12}$ are independently selected from a group of hydrogen, halogen, hydroxyl, alkyl, alkoxyl, halogenated alkyl, mercaptoalkyl, alkenyl, alkynyl, cycloalkyl, aryl, cyano, thiazolyl, triazolyl, imidazolyl, tetrazolyl, benzothiazolyl, and benzoimidazolyl, and pharmaceutically acceptable salts and esters thereof. In a particular embodiment, n is 3 or 4.

In another embodiment, the invention includes a composition having a therapeutic compound that is a compound of Formula V-A:

$$\text{(V-A)}$$

wherein:

A is nitrogen or oxygen;

$R^{11}$ is hydrogen, salt-forming cation, ester forming group, —$(CH_2)_x$-Q, or when A is nitrogen, A and $R^{11}$ taken together may be a natural or unnatural amino acid residue or a salt or ester thereof;

Q is hydrogen, thiazolyl, triazolyl, imidazolyl, benzothiazolyl, or benzoimidazolyl;

x is 0, 1, 2, 3, or 4;

n is 0, 1, 2, 3, 4, 5, 6, 7, 8, 9, or 10;

aa is a natural or unnatural amino acid residue;

m is 0, 1, 2, or 3;

$R^{14}$ is hydrogen or protecting group;

$R^{15}$ is hydrogen, alkyl or aryl, and pharmaceutically acceptable salts and prodrugs thereof. In a particular embodiment, n is 3 or 4.

In another embodiment, the invention includes a composition having a therapeutic compound that is a compound of the Formula VI-A:

$$\text{(VI-A)}$$

wherein;

n is 1, 2, 3, 4, 5, 6, 7, 8, 9, or 10;

A is oxygen or nitrogen;

$R^{11}$ is hydrogen, salt-forming cation, ester forming group, —$(CH_2)_x$-Q, or when A is nitrogen, A mid $R^{11}$ taken together may be a natural or unnatural amino acid residue or a salt or ester thereof;

Q is hydrogen, thiazolyl, triazolyl, imidazolyl, benzothiazolyl, or benzoimidazolyl;

x is 0, 1, 2, 3, or 4;

$R^{19}$ is hydrogen, alkyl or aryl;

$Y^1$ is oxygen, sulfur, or nitrogen;

$Y^2$ is carbon, nitrogen, or oxygen;

$R^{20}$ is hydrogen, alkyl, amino, mercaptoalkyl, alkenyl, alkynyl, cycloalkyl, aryl, arylalkyl, thiazolyl, triazolyl, tetrazolyl, imidazolyl, benzothiazolyl, or benzoimidazolyl;

$R^{21}$ is hydrogen, alkyl, mercaptoalkyl, alkenyl, alkynyl, cycloalkyl, aryl, arylalkyl, thiazolyl, triazolyl, tetrazolyl, imidazolyl, benzothiazolyl, benzoimidazolyl, or absent if $Y^2$ is oxygen;

$R^{22}$ is hydrogen, alkyl, mercaptoalkyl, alkenyl, alkynyl, cycloalkyl, aryl, arylalkyl, thiazolyl, triazolyl, tetrazolyl, imidazolyl, benzothiazolyl, benzoimidazolyl; or $R^{22}$ is hydrogen, hydroxyl, alkoxy or aryloxy if $Y^1$ is nitrogen; or $R^{22}$ is absent if $Y^1$ is oxygen or sulfur; or $R^{22}$ and $R^{21}$ may be linked to form a cyclic moiety if $Y^1$ is nitrogen;

or pharmaceutically acceptable salts thereof. In a particular embodiment, n is 3 or 4.

In another embodiment, the invention includes a composition having a therapeutic compound that is a compound of Formula VII-A:

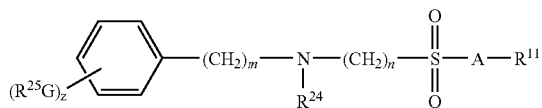

(VII-A)

wherein:
n is 2, 3, or 4;
A is oxygen or nitrogen;
$R^{11}$ is hydrogen, salt-forming cation, ester forming group, —(CH$_2$)$_x$-Q, or when A is nitrogen, A and $R^{11}$ taken together may be a natural or unnatural amino acid residue or a salt or ester thereof;
Q is hydrogen, thiazolyl, triazolyl, imidazolyl, benzothiazolyl, or benzoimidazolyl;
x is 0, 1, 2, 3, or 4;
G is a direct bond or oxygen, nitrogen, or sulfur;
z is 0, 1, 2, 3, 4, or 5;
m is 0 or 1;
$R^{24}$ is selected from the group consisting of hydrogen, alkyl, mercaptoalkyl, alkenyl, alkynyl, aroyl, alkylcarbonyl, aminoalkylcarbonyl, cycloalkyl, aryl, arylalkyl, thiazolyl, triazolyl, imidazolyl, benzothiazolyl, and benzoimidazolyl;
each $R^{25}$ is independently selected from hydrogen, halogen, cyano, hydroxyl, alkoxy, thiol, amino, nitro, alkyl, aryl, carbocyclic, or heterocyclic, and pharmaceutically acceptable salts thereof. In a particular embodiment, n is 3 or 4.

Additional compounds include, for example, therapeutic compounds of Formula (I-B):

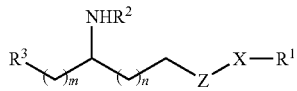

(I-B)

wherein:
X is oxygen or nitrogen;
Z is C=O, S(O)$_2$, or P(O)OR$^7$;
m and n are each independently 0, 1, 2, 3, 4, 5, 6, 7, 8, 9 or 10;
$R^1$ and $R^7$ are each independently hydrogen, metal ion, alkyl, mercaptoalkyl, alkenyl, alkynyl, cycloalkyl, aryl, a moiety together with X to form a natural or unnatural amino acid residue, or —(CH$_2$)$_p$—Y;

Y is hydrogen or a heterocyclic moiety selected from the group consisting of thiazolyl, triazolyl, tetrazolyl, imidazolyl, benzothiazolyl, and benzoimidazolyl;
p is 0, 1, 2, 3, or 4;
$R^2$ is hydrogen, alkyl, mercaptoalkyl, alkenyl, alkynyl, cycloalkyl, aryl, alkylcarbonyl, arylcarbonyl, or alkoxycarbonyl;
$R^3$ is hydrogen, amino, cyano, alkyl, mercaptoalkyl, alkenyl, alkynyl, cycloalkyl, heterocyclic, substituted or unsubstituted aryl, heteroaryl, thiazolyl, triazolyl, tetrazolyl, imidazolyl, benzothiazolyl, or benzoimidazolyl, and pharmaceutically acceptable salts, esters, and prodrugs thereof.

In a further embodiment, m is 0, 1, or 2. In another further embodiment, n is 0, 1, or 2, e.g., 1 or 2. In another further embodiment, $R^3$ is aryl, e.g., heteroaryl or phenyl. In yet another embodiment, Z is S(O)$_2$.

In another embodiment, the therapeutic compound of the invention is of the Formula (II-B)

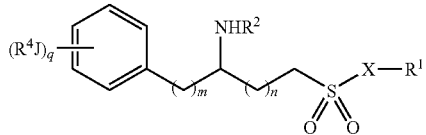

(II-B)

wherein:
X is oxygen or nitrogen;
m and n are each independently 0, 1, 2, 3, 4, 5, 6, 7, 8, 9 or 10;
$R^1$ is hydrogen, metal ion, alkyl, mercaptoalkyl, alkenyl, alkynyl, cycloalkyl, aryl, or a moiety together with X to form a natural or unnatural amino acid residue, or —(CH$_2$)$_p$—Y;
Y is hydrogen or a heterocyclic moiety selected from the group consisting of thiazolyl, triazolyl, tetrazolyl, imidazolyl, benzothiazolyl, and benzoimidazolyl;
each $R^4$ is independently selected from the group consisting of hydrogen, halogen, hydroxyl, thiol, amino, cyano, nitro, alkyl, aryl, carbocyclic or heterocyclic;
$R^2$ is hydrogen, alkyl, mercaptoalkyl, alkenyl, alkynyl, cycloalkyl, aryl, alkylcarbonyl, arylcarbonyl, or alkoxycarbonyl;
J is absent, oxygen, nitrogen, sulfur, or a divalent linkmoiety consisting of, without limitation to, lower alkylene, alkylenyloxy, alkylenylamino, alkylenylthio, alkylenyloxyalkyl, alkylenylamonialkyl, alkylenylthioalkyl, alkenyl, alkenyloxy, alkenylamino, or alkenylthio; and
q is 1, 2, 3, 4, or 5, and pharmaceutically acceptable salts, esters and prodrugs thereof. In a particular embodiment, n is 1 or 2.

In a yet further embodiment, the therapeutic compound of the invention is of the Formula (III-B):

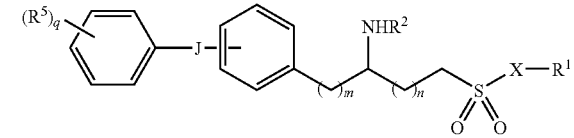

(III-B)

wherein:

X is oxygen or nitrogen;

m and n are each independently 0, 1, 2, 3, 4, 5, 6, 7, 8, 9 or 10;

q is 1, 2, 3, 4, or 5;

$R^1$ is hydrogen, metal ion, alkyl, mercaptoalkyl, alkenyl, alkynyl, cycloalkyl, aryl, or a moiety together with X to form a natural or unnatural amino acid residue, or —$(CH_2)_p$—Y;

Y is hydrogen or a heterocyclic moiety selected from the group consisting of thiazolyl, triazolyl, tetrazolyl, imidazolyl, benzothiazolyl, and benzoimidazolyl;

p is 0, 1, 2, 3, or 4;

$R^2$ is hydrogen, alkyl, mercaptoalkyl, alkenyl, alkynyl, cycloalkyl, aryl, alkylcarbonyl, arylcarbonyl, or alkoxycarbonyl;

$R^5$ is selected from the group consisting of hydrogen, halogen, amino, nitro, hydroxy, carbonyl, thiol, carboxy, alkyl, alkoxy, alkoxycarbonyl, acyl, alkylamino, and acylamino;

J is absent, oxygen, nitrogen, sulfur, or a divalent link-moiety consisting of, without limitation to, lower alkylene, alkylenyloxy, alkylenylamino, alkylenylthio, alkylenyloxyalkyl, alkylenylamonialkyl, alkylenylthioalkyl, alkenyl, alkenyloxy, alkenylamino, or alkenylthio; and pharmaceutically acceptable salts, esters, and prodrugs thereof. In a particular embodiment, n is 1 or 2.

In yet another embodiment, the therapeutic compound of the invention is:

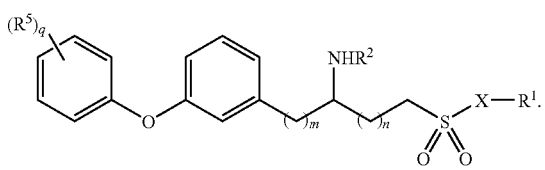

(IV-B)

wherein:

X is oxygen or nitrogen;

m and n are each independently 0, 1, 2, 3, 4, 5, 6, 7, 8, 9 or 10;

q is 1, 2, 3, 4, or 5;

$R^1$ is hydrogen, metal ion, alkyl, mercaptoalkyl, alkenyl, alkynyl, cycloalkyl, aryl, or a moiety together with X to form a natural or unnatural amino acid residue, or —$(CH_2)_p$—Y;

Y is hydrogen or a heterocyclic moiety selected from the group consisting of thiazolyl, triazolyl, tetrazolyl, imidazolyl, benzothiazolyl, and benzoimidazolyl;

p is 0, 1, 2, 3, or 4;

$R^2$ is hydrogen, alkyl, mercaptoalkyl, alkenyl, alkynyl, cycloalkyl, aryl, alkylcarbonyl, arylcarbonyl, or alkoxycarbonyl;

$R^5$ is selected from the group consisting of hydrogen, halogen, amino, nitro, hydroxy, carbonyl, thiol, carboxy, alkyl, alkoxy, alkoxycarbonyl, acyl, alkylamino, acylamino; and pharmaceutically acceptable salts, esters, and prodrugs thereof. In a further embodiment, m is 0. In a particular embodiment, n is 1 or 2.

In another embodiment, the invention pertains to therapeutic compounds of Formula (V-B):

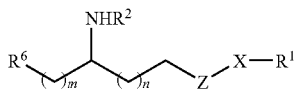

(V-B)

wherein:

X is oxygen or nitrogen,

Z is C=O, $S(O)_2$, or $P(O)OR^7$;

$R^1$ is hydrogen, metal ion, alkyl, mercaptoalkyl, alkenyl, alkynyl, cycloalkyl, aryl, or a moiety together with X to form a natural or unnatural amino acid residue, or —$(CH_2)_p$—Y;

Y is hydrogen or a heterocyclic moiety selected from the group consisting of thiazolyl, triazolyl, tetrazolyl, imidazolyl, benzothiazolyl, and benzoimidazolyl;

m and n are each independently 0, 1, 2, 3, 4, 5, 6, 7, 8, 9 or 10;

$R^2$ is hydrogen, alkyl, mercaptoalkyl, alkenyl, alkynyl, cycloalkyl, aryl, alkylcarbonyl, arylcarbonyl, or alkoxycarbonyl; and $R^6$ is a substituted or unsubstituted heterocyclic moiety. In a further embodiment, m is 0 or 1. In another embodiment, n is 0 or 1. In another further embodiment, $R^6$ is thiazolyl, oxazoylyl, pyrazolyl, indolyl, pyridinyl, thiazinyl, thiophenyl, benzothiophenyl, dihydroimidazolyl, dihydrothiazolyl, oxazolidinyl, thiazolidinyl, tetrahydropyrimidinyl, or oxazinyl. In yet another embodiment, Z is $S(O)_2$. In a particular embodiment, n is 1 or 2.

In certain embodiments of the invention, the therapeutic formulations of the invention may contain pharmaceutically acceptable inactive ingredients and a therapeutic compound having the formula 3-amino-1-propanesulfonate/X, where X is a counter cation or forms an ester with the sulfonate, wherein the ester or counter cation includes alcohol radicals or positively charged atoms and moieties, respectively, that do not significantly affect the ability of the therapeutic formulation to reduce or prevent gastrointestinal intolerance. In a preferred embodiment, the cationic group is hydrogen ($H^+$) and the compound is 3-amino-1-propanesulfonic acid. In certain other embodiments, the hydrogen is replaced by a pharmaceutically acceptable cation or an alcohol radical or its equivalent, and the compound is a salt or ester of the acid. Pharmaceutically acceptable salts or esters of the therapeutic compound that do not significantly affect the ability of the therapeutic formulation to reduce or prevent gastrointestinal intolerance are within the scope of the invention. For example, the cation can be a pharmaceutically acceptable alkali metal, alkaline earth, higher valency cation (e.g., aluminum salt), polycationic counter ion or ammonium, and the alcohol radical can be a pharmaceutically acceptable alcohol radical. In a particular embodiment, the pharmaceutically acceptable salt is a sodium salt, however, other salts are also contemplated within their pharmaceutically acceptable range.

In general, the therapeutic compounds appropriate for use in the therapeutic formulations of the invention comprise at least one sulfonate group covalently bonded to a substituted or unsubstituted aromatic or aliphatic group.

In another embodiment, the therapeutic compound has at least one sulfonate group covalently bonded to a substituted or unsubstituted aliphatic group. In a similar embodiment the therapeutic compound has at least two sulfonate groups covalently bonded to a substituted or unsubstituted aliphatic group. In another embodiment, the therapeutic compound has at least one sulfonate group covalently bonded to a substituted or unsubstituted lower alkyl group. In a similar embodiment the therapeutic compound has at least two sulfonate groups covalently bonded to a substituted or unsubstituted lower alkyl group.

In yet another embodiment, the therapeutic compound has at least one sulfonate group covalently bonded to an amino-substituted aliphatic group. In a similar embodiment the therapeutic compound has at least two sulfonate groups covalently bonded to an amino-substituted aliphatic group. In still yet another embodiment, the therapeutic compound has at least one sulfonate group covalently bonded to an amino-substituted lower alkyl group. In a similar embodiment the therapeutic compound has at least two sulfonate groups covalently bonded to an amino-substituted lower alkyl group.

A "sulfonate group" as used herein is an $-SO_3^-H$ or $-SO_3X$ group bonded to a carbon atom, where X is a cationic group or an ester group. Similarly, a "sulfonic acid" compound has a $-SO_3H$ group bonded to a carbon atom. A "sulfate" as used herein is an $-OSO_3^-H$ or $-OSO_3X$ group bonded to a carbon atom, where X is a cationic group or an ester group; and a "sulfuric acid" compound has a $-OSO_3H$ group bonded to a carbon atom. According to the invention, a suitable cationic group may be a hydrogen atom. In certain cases, the cationic group may actually be another group on the therapeutic compound that is positively charged at physiological pH, for example an amino group. Such compounds containing such a cationic group covalently bonded to the therapeutic compound itself may be referred to as an "inner salt" or "zwitterion." For example, the compound 3-amino-1-propanesulfonic acid may form an inner salt or zwitterion under appropriate conditions.

Unless otherwise stipulated, the chemical moieties herein may be substituted or unsubstituted. In some embodiments, the term. "substituted" means that the moiety has substituents placed on the moiety other than hydrogen which allow the molecule to perform its intended function. Examples of substituents, which are not intended to be limiting, include moieties selected from straight or branched alkyl (preferably $C_1$-$C_5$), cycloalkyl (preferably $C_3$-$C_8$), alkoxy (preferably $C_1$-$C_6$), thioalkyl (preferably $C_1$-$C_6$), alkenyl (preferably $C_2$-$C_6$), alkynyl (preferably $C_2$-$C_6$), heterocyclic, carbocyclic, aryl (e.g., phenyl), aryloxy (e.g., phenoxy), aralkyl (e.g., benzyl), aryloxyalkyl (e.g., phenyloxyalkyl), arylacetamidoyl, alkylaryl, heteroaralkyl, alkylcarbonyl and arylcarbonyl or other such acyl group, heteroarylcarbonyl, or heteroaryl group, $(CR'R'')_{0-3}NR'R''$ (e.g., $-NH_2$), $(CR'R'')_{0-3}CN$ (e.g., $-CN$), $-NO_2$, halogen (e.g., $-F$, $-Cl$, $-Br$, or $-I$), $(CR'R'')_{0-3}C(halogen)_3$ (e.g., $-CF_3$), $(CR'R'')_{0-3}CH(halogen)_2$, $(CR'R'')_{0-3}CH_2(halogen)$, $(CR'R'')_{0-3}CONR'R''$, $(CR'R'')_{0-3}(CNH)NR'R''$, $(CR'R'')_{0-3}S(O)_{1-2}NR'R''$, $(CR'R'')_{0-3}CHO$, $(CR'R'')_{0-3}O(CR'R'')_{0-3}H$, $(CR'R'')_{0-3}S(O)_{0-3}R'$ (e.g., $-SO_3H$, $-OSO_3H$), $(CR'R'')_{0-3}O(CR'R'')_{0-3}H$ (e.g., $-CH_2OCH_3$ and $-OCH_3$), $(CR'R'')_{0-3}S(CR'R'')_{0-3}H$ (e.g., $-SH$ and $-SCH_3$), $(CR'R'')_{0-3}OH$ (e.g., $-OH$), $(CR'R'')_{0-3}COR'$, $(CR'R'')_{0-3}$ (substituted or unsubstituted phenyl), $(CR'R'')_{0-3}(C_3$-$C_8$ cycloalkyl), $(CR'R'')_{0-3}CO_2R'$ (e.g., $-CO_2H$), or $(CR'R'')_{0-3}OR'$ group, or the side chain of any naturally occurring amino acid; wherein R' and R" are each independently hydrogen, a $C_1$-$C_5$ alkyl, $C_2$-$C_5$ alkenyl, $C_2$-$C_5$ alkynyl, or aryl group. "Substituents" may also include, for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), imino, sulfihydryl, alkylthio, arylthio, thiocarboxylate, sulfate, sulfonato, sulfamoyl, sulfonamido, nitro, trifluoromethyl, azido, heterocyclyl, aralkyl, or an aromatic or heteroaromatic moiety.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" includes all permissible substituents of organic compounds. In a broad aspect, the permissible substituents include acyclic and cyclic, branched and unbranched, carbocyclic and heterocyclic, aromatic and nonaromatic substituents of organic compounds. The permissible substituents can be one or more and the same or different for appropriate organic compounds.

In certain embodiments, a "substituent" may be selected from the group consisting of, for example, halogeno, trifluoromethyl, nitro, cyano, $C_1$-$C_6$ alkyl, $C_2$-$C_6$ alkenyl, $C_2$-$C_6$ alkynyl, $C_1$-$C_6$ alkylcarbonyloxy, arylcarbonyloxy, $C_1$-$C_6$ alkoxycarbonyloxy, aryloxycarbonyloxy, $C_1$-$C_6$ alkylcarbonyl, $C_1$-$C_6$ alkoxycarbonyl, $C_1$-$C_6$ alkoxy, $C_1$-$C_6$ alkylthio, arylthio, heterocyclyl, aralkyl, and aryl (including heteroaryl) groups.

In general, the therapeutic compounds of the invention are small molecules. A "small molecule" refers to a compound that is not itself the product of gene transcription or translation (e.g., protein, RNA, or DNA). Preferably a "small molecule" is a low molecular weight compound, e.g., less than 7500 amu, more preferably less 5000 amu, e.g., less than about 2500 amu, and even more preferably less than 1000 amu. In other cases, the compound may be a biological product, such as an antibody or an immunogenic peptide.

The term "amine" or "amino," as used herein, refers to an unsubstituted or substituted moiety of the formula $-NR^aR^b$, in which $R^a$ and $R^b$ are each independently hydrogen, alkyl, aryl, or heterocyclyl, or $R^a$ and $R^b$, taken together with the nitrogen atom to which they are attached, form a cyclic moiety having from 3 to 8 atoms in the ring. Thus, the term amino includes cyclic amino moieties such as piperidinyl or pyrrolidinyl groups, unless otherwise stated. Thus, the term "alkylamino" as used herein means an alkyl group having an amino group attached thereto. Suitable alkylamino groups include groups having 1 to about 12 carbon atoms, for example, 1 to about 6 carbon atoms. The term amino includes compounds or moieties in which a nitrogen atom is covalently bonded to at least one carbon or heteroatom. The term "dialkylamino" includes groups wherein the nitrogen atom is bound to at least two alkyl groups. The term "arylamino" and "diarylamino" include groups wherein the nitrogen is bound to at least one or two aryl groups, respectively. The term "alkylarylamino" refers to an amino group which is bound to at least one alkyl group and at least one aryl group. The term "alkaminoalkyl" refers to an alkyl, alkenyl, or alkynyl group substituted with an alkylamino group. The term "amide" or "aminocarbonyl" includes compounds or moieties which contain a nitrogen atom which is bound to the carbon of a carbonyl or a thiocarbonyl group.

The term "aliphatic group" includes organic compounds characterized by straight or branched chains, typically having between 1 and 22 carbon atoms. Aliphatic groups include alkyl groups, alkenyl groups and alkynyl groups. The chains may be branched or cross-linked. Alkyl groups include saturated hydrocarbons having one or more carbon atoms, including straight-chain alkyl groups and branched-chain alkyl groups. The term "alicyclic group" includes closed ring structures of three or more carbon atoms. Alicyclic groups include cycloparaffins or naphthenes that are saturated cyclic hydrocarbons, cycloolefins which are unsaturated with two or more double bonds, and cycloacetylenes which have a triple bond. They do not include aromatic groups. Examples of cycloparaffins include cyclopropane, cyclohexane, and cyclopentane. Examples of cycloolefins include cyclopentadiene and cyclooctatetraene. Alicyclic groups also include polycyclic rings, e.g., fused ring structures, and substituted alicyclic groups such as alkyl substituted alicyclic groups. "Polycyclyl" or "polycyclic group" includes two or more cyclic rings (e.g., cycloalkyls, cycloalkenyls, cycloalkynyls, aryls or heterocyclyls) in which one or more carbons are common to two adjoining rings, e.g., the rings are "fused rings" or spiro-rings. Rings that are joined through non-adjacent atoms are termed "bridged" rings.

As used herein, "alkyl" groups include saturated hydrocarbons having one or more carbon atoms, including straight-chain alkyl groups, e.g., methyl, ethyl, propyl, butyl, pentyl, hexyl, heptyl, octyl, nonyl, decyl, etc.; cyclic alkyl groups (or "cycloalkyl" or "alicyclic" or "carbocyclic" groups), e.g., cyclopropyl, cyclopentyl, cyclohexyl, cycloheptyl, cyclooctyl, etc.; branched-chain alkyl groups, e.g., isopropyl, tert-butyl, sec-butyl, isobutyl, etc.; and alkyl-substituted alkyl groups, e.g., alkyl-substituted cycloalkyl groups and cycloalkyl-substituted alkyl groups.

Accordingly, the invention relates to, for example, substituted or unsubstituted alkylsulfonic acids that are substituted or unsubstituted straight-chain alkylsulfonic acids, substituted or unsubstituted cycloalkylsulfonic acids, and substituted or unsubstituted branched-chain alkylsulfonic acids.

In certain embodiments, a straight-chain or branched-chain alkyl group may have 30 or fewer carbon atoms in its backbone, e.g., $C_1$-$C_{30}$ for straight-chain or $C_3$-$C_{30}$ for branched-chain. In certain embodiments, a straight-chain or branched-chain alkyl group may have 20 or fewer carbon atoms in its backbone, e.g., $C_1$-$C_{20}$ for straight-chain or $C_3$-$C_{20}$ for branched-chain, and more particularly, for example, 18 or fewer. Additionally, example cycloalkyl groups have from 4-10 carbon atoms in their ring structure, e.g., 4-7 carbon atoms in the ring structure.

The term "lower alkyl" refers to alkyl groups having from 1 to 8 carbons in the chain, and to cycloalkyl groups having from 3 to 8 carbons in the ring structure. Unless the number of carbons is otherwise specified, "lower" as in "lower alkyl," means that the moiety has at least one and less than about 8 carbon atoms. In certain embodiments, a straight-chain or branched-chain lower alkyl group has 6 or fewer carbon atoms in its backbone (e.g., $C_1$-$C_6$ for straight-chain, $C_3$-$C_6$ for branched-chain), for example, methyl, ethyl, propyl, isopropyl, butyl, isobutyl, sec-butyl, and tert-butyl. Likewise, cycloalkyl groups may have from 3-8 carbon atoms in their ring structure, for example, 5 or 6 carbons in the ring structure. The term "C1-C6" as in "C1-C6 alkyl" means alkyl groups containing 1 to 6 carbon atoms.

Moreover, unless otherwise specified the term alkyl includes both "unsubstituted alkyls" and "substituted alkyls," the latter of which refers to alkyl groups having substituents replacing one or more hydrogens on one or more carbons of the hydrocarbon backbone. Such substituents may include, for example, alkenyl, alkynyl, halogeno, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or aromatic (including heteroaromatic) groups.

The terms "alkenyl" and "alkynyl" refer to unsaturated aliphatic groups analogous to alkyls, including straight and branched chains, and cyclical structures, but which contain at least one double or triple bond respectively. Suitable alkenyl and alkynyl groups include groups having 2 to about 12 carbon atoms, preferably from 2 to about 6 carbon atoms.

The term "aromatic group" includes unsaturated cyclic hydrocarbons containing one or more rings. In general, the term "aryl" includes groups, including 5- and 6-membered single-ring aromatic groups that may include from zero to four heteroatoms, for example, groups derived from benzene, pyrrole, furan, thiophene, thiazole, isothiaozole, imidazole, triazole, tetrazole, pyrazole, oxazole, isooxazole, pyridine, pyrazine, pyridazine, and pyrimidine, and the like. Furthermore, the term aryl includes multicyclic aryl groups, e.g., groups derived from tricyclic, bicyclic, e.g., naphthalene, benzoxazole, benzodioxazole, benzothiazole, benzoimidazole, benzothiophene, methylenedioxyphenyl, quinoline, isoquinoline, napthyridine, indole, benzofuran, purine, benzofuran, deazapurine, or indolizine. Those aryl groups having heteroatoms in the ring structure may also be referred to as "aryl heterocycles," "heteroaryls," or "heteroaromatics".

Aryl groups may also be fused or bridged with alicyclic or heterocyclic rings which are not aromatic so as to form a polycycle (e.g., tetralin). Those aryl groups having heteroatoms in the ring structure may also be referred to as aryl heterocycles, heterocycles, heteroaryls, or heteroaromatics, which, for example, include any ring formed that incorporates a heteroatom or an atom that is not carbon. The ring may be saturated or unsaturated and may contain one or more double bonds. Examples of some heterocyclic groups include pyridyl, furanyl, thiophenyl, morpholinyl, and indolyl groups.

The term "heteroatom" includes atoms of any element other than carbon or hydrogen. Preferred heteroatoms are nitrogen, oxygen, sulfur and phosphorus. Heterocyclic groups also include closed ring structures in which one or more of the atoms in the ring is an element other than carbon, for example, nitrogen, sulfur, or oxygen. Heterocyclic groups may be saturated or unsaturated and heterocyclic groups such as pyrrole and furan may have aromatic character. They include fused ring structures such as quinoline and isoquinoline. Other examples of heterocyclic groups include pyridine and purine. Examples of heteroaromatic and heteroalicyclic groups may have 1 to 3 separate or fused rings with 3 to about 8 members per ring and one or more N, O, or S atoms, e.g., coumarinyl, quinolinyl, pyridyl, pyrazinyl, pyrimidyl, furyl, pyrrolyl, thienyl, thiazolyl, oxazolyl, imidazolyl, indolyl, benzofuranyl, benzothiazolyl, tetrahydrofuranyl, tetrahydropyranyl, piperidinyl, morpholino, and pyrrolidinyl.

III. Therapeutic Formulation of the Invention

The invention also relates to a pharmaceutical composition for inhibiting amyloid deposition in a subject comprising a therapeutic formulation as defined herein, in an amount sufficient to inhibit amyloid deposition in a subject, and a pharmaceutically acceptable vehicle.

In another embodiment, the invention is a pharmaceutical composition for treating amyloidosis in a subject comprising a therapeutic formulation as described herein, in an amount sufficient to inhibit amyloid deposition in a subject, and a pharmaceutically acceptable vehicle.

In another embodiment, the present invention pertains to a pharmaceutical composition for treating or preventing an amyloid-related disease, e.g., type II diabetes or an Aβ-related disease, e.g., Alzheimer's disease, cerebral amyloid angiopathy, inclusion body myositis, macular degeneration, Down's syndrome, and hereditary cerebral hemorrhage, comprising a therapeutic formulation comprising a therapeutic compound formulated to significantly reduce or prevent gastrointestinal intolerance, in an amount sufficient to prevent or treat an amyloid-related disease in a subject, and a pharmaceutically acceptable vehicle.

In certain embodiments, the therapeutic compound of the therapeutic formulations of the invention interacts with a binding site for a basement membrane glycoprotein or proteoglycan in an amyloidogenic protein and thereby inhibits the binding of the amyloidogenic protein to the basement membrane constituent. Basement membrane glycoproteins and proteoglycans include laminin, collagen type IV, fibronectin, agrin, perlecan, and heparan sulfate proteoglycan (HSPG). In a particular embodiment, the therapeutic compound inhibits an interaction between an amyloidogenic protein and agrin, perlecan, or HSPG. Furthermore, consensus binding site motifs for HSPG in amyloidogenic proteins have been described (see e.g. Cardin and Weintraub (1989) Arteriosclerosis 9:21-32).

Accordingly, the invention includes a packaged pharmaceutical composition for inhibiting amyloid deposition in a subject, comprising a container holding a therapeutically effective amount of a therapeutic formulation as described herein; and instructions for using the compound for inhibiting amyloid deposition in a subject. In certain embodiments, the disease related to such amyloid deposition is selected from the group consisting of Alzheimer's disease, cerebral amyloid angiopathy, inclusion body myositis, macular degeneration, Down's syndrome, Mild Cognitive Impairment, type II diabetes, and hereditary cerebral hemorrhage.

The term "container" includes any receptacle for holding the therapeutic formulation. For example, in one embodiment, the container is the packaging that contains the formulation. In other embodiments, the container is not the packaging that contains the formulation, i.e., the container is a receptacle, such as a box or vial that contains the packaged formulation or unpackaged formulation and the instructions for use of the formulation. Moreover, packaging techniques are well known in the art. It should be understood that the instructions for use of the therapeutic formulation may be contained on the packaging containing the therapeutic formulation, and as such the instructions form an increased functional relationship to the packaged product. However, it should be understood that the instructions can contain information pertaining to the compound's ability to perform its intended function, erg., reduce or prevent gastrointestinal intolerance.

In another embodiment, the invention includes a packaged pharmaceutical composition for treating amyloidosis in a subject, comprising a container holding a therapeutically effective amount of a therapeutic formulation as described herein; and instructions for using the compound for treating amyloidosis in a subject.

In yet another embodiment, the invention includes a packaged pharmaceutical composition for treating a viral infection, comprising a container holding a therapeutically effective amount of a therapeutic formulation as described herein; and instructions for using the compound for treating the viral infection.

Another embodiment of the invention pertains to a packaged pharmaceutical composition for treating a bacterial infection, comprising a container holding a therapeutically effective amount of a therapeutic formulation of the invention; and instructions for using the therapeutic compound for treating the bacterial infection.

Another embodiment of the invention pertains to a packaged pharmaceutical composition for inhibiting the binding of a chemokine to a glycosaminoglycan, comprising a container holding a therapeutically effective amount of a therapeutic formulation of the invention; and instructions for using the therapeutic compound for inhibiting the binding of a chemokine to a glycosaminoglycan.

The therapeutic formulations of the invention may also include combinations of two or more therapeutic compounds. Accordingly, the invention relates to a therapeutic formulation for the treatment of Alzheimer's disease comprising 3-amino-1-propanesulfonic acid and a second drug that targets additional symptoms, e.g., secondary symptoms of Alzheimer's disease. In certain embodiments, the "second drug" may be a cholinesterase inhibitor, such as an acetylcholinesterase or butyryl-cholinesterase inhibitor, e.g., tacrine, donepezil, rivastigmine, or galantamine. In another embodiment, the second drug may be an NMDA receptor antagonist, such as memantine. In yet another embodiment, the second drug may be an antioxidant, vitamin E, estrogen, a nonsteroidal anti-inflammatory agent (e.g., aspirin or naproxen), a cholesterol modifying agent such as statin, or *ginkgo biloba*. The methods for administering the active agent as discussed herein can—when used in conjunction with another therapeutic agent—be used as a first line therapy or otherwise, e.g., as a second line therapy to other therapeutics, including known effective treatment methods.

The therapeutic formulation of the invention may further include a pharmaceutically acceptable vehicle. As used herein "pharmaceutically acceptable vehicle" includes any and all coatings, antibacterial and antifungal agents, and absorption delaying agents, and the like that are compatible with the activity of the compound, are physiologically acceptable to the subject, and that do not significantly affect the ability of the therapeutic formulation to perform its intended function or do not significantly affect the ability of the therapeutic formulation to reduce or prevent gastrointestinal intolerance. Supplementary active compounds can also be incorporated into the compositions as long as they do not significantly affect the ability of the therapeutic formulation to reduce or prevent nausea.

Active compounds are administered at a therapeutically effective dosage sufficient to inhibit amyloid deposition in a subject. A "therapeutically effective dosage" preferably inhibits amyloid deposition by at least about 20%, more preferably by at least about 40%, even more preferably by at least about 60%, and still more preferably by at least about 80% relative to untreated subjects. The ability of a compound to inhibit amyloid deposition can be evaluated in an animal model system that may be predictive of efficacy in inhibiting amyloid deposition in human diseases. Alternatively, the ability of a compound to inhibit amyloid deposition can be evaluated by examining the ability of the compound to inhibit an interaction between an amyloidogenic protein and a basement membrane constituent, e.g., as described in U.S. Pat. No. 5,164,295, which is hereby expressly incorporated herein by reference, or by the mass spectroscopy assay described in Example 5.

The term "subject" includes living organisms in which amyloidosis can occur, or which are susceptible to amyloid diseases, e.g., Alzheimer's disease, Down's syndrome, Mild Cognitive Impairment, CAA, dialysis-related ($\beta_2$M) amyloidosis, secondary (AA) amyloidosis, primary (AL) amyloidosis, hereditary amyloidosis, diabetes, etc. Examples of subjects include humans, monkeys, cows, sheep, goats, dogs, and cats. The language "subject" includes animals (e.g., mammals, e.g., cats, dogs, horses, pigs, cows, goats, sheep, rodents, e.g., mice or rats, rabbits, squirrels, bears, primates (e.g., chimpanzees, monkeys, gorillas, and humans)), as well as chickens, ducks, peking ducks, geese, and transgenic species thereof.

In certain embodiments of the invention, the subject is in need of treatment by the methods of the invention, and is selected for treatment based on this Deed. A subject in need of treatment is art-recognized, and includes subjects that have been identified as having a disease or disorder related to amyloids or amyloid-deposition or amyloidosis, having a symptom of such a disease or disorder, or at risk of such a disease or disorder, and would be expected, based on diagnosis, e.g., medical diagnosis, to benefit from treatment (e.g., curing, healing, preventing, alleviating, relieving, altering, remedying, ameliorating, improving, or affecting the disease or disorder, the symptom of the disease or disorder, or the risk of the disease or disorder).

Administration of the compositions of the present invention to a subject to be treated can be carried out using known procedures, at dosages and for periods of time effective to inhibit amyloid deposition in the subject. An effective amount of the therapeutic compound necessary to achieve a therapeutic effect may vary according to factors such as the amount of amyloid already deposited at the clinical site in the subject, the age, sex, and weight of the subject, and the ability of the therapeutic compound to inhibit amyloid deposition in the subject. Dosage regimens can be adjusted to provide the optimum therapeutic response. For example, several divided doses may be administered daily or the dose may be proportionally reduced as indicated by the exigencies of the therapeutic situation. A non-limiting example of an effective dose range for a therapeutic compound of the invention (e.g., 3-amino-1-propanesulfonic acid) is between 1 and 500 mg/kg of body weight/per day. In another non-limiting example, the active agent of 3-amino-1-propanesulfonic acid or pharmaceutically acceptable salt thereof is provided in a formulation in an amount of about 200 mg or less, preferably from about 50 to about 150 mg and particularly about 50, about 100 or about 150 mg. In a further aspect, the invention is directed to methods for daily or twice daily administering of such formulations to a patient in need thereof. One of ordinary skill in the art would be able to study the relevant factors and make the determination regarding the effective amount of the therapeutic compound without undue experimentation.

Actual dosage levels of the active ingredients in the pharmaceutical compositions of this invention may be varied so as to obtain an amount of the active ingredient that is effective to achieve the desired therapeutic response for a particular patient, composition, and mode of administration, without being toxic to the patient.

In particular, the selected dosage level will depend upon a variety of factors including the activity of the particular compound of the present invention employed, the time of administration, the rate of excretion of the particular compound being employed, the duration of the treatment, other drugs, compounds or materials used in combination with the particular compound employed, the age, sex, weight, condition, general health and prior medical history of the patient being treated, and like factors well known in the medical arts.

A medical doctor, e.g., physician or veterinarian, having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

The regimen of administration can affect what constitutes an effective amount. The therapeutic formulations can be administered to the subject either prior to or after the onset of amyloidosis. Further, several divided dosages, as well as staggered dosages, can be administered daily or sequentially, or the dose can be continuously infused, or can be a bolus injection. Further, the dosages of the therapeutic formulations can be proportionally increased or decreased as indicated by the exigencies of the therapeutic or prophylactic situation.

In particular embodiments, it is especially advantageous to formulate compositions in dosage unit form for ease of administration and uniformity of dosage. Dosage unit form as used herein refers to physically discrete units suited as unitary dosages for the subjects to be treated; each unit containing a predetermined quantity of therapeutic compound calculated to produce the desired therapeutic effect in association with the required pharmaceutical vehicle. The specification for the dosage unit forms of the invention are dictated by and directly dependent on (a) the unique characteristics of the therapeutic compound and the particular therapeutic effect to be achieved, and (b) the limitations inherent in the art of compounding/formulating such a therapeutic compound for the treatment of amyloid deposition in subjects.

A further aspect of the invention includes pharmaceutical compositions for treating amyloidosis; inhibiting amyloid deposition; or preventing or treating amyloid-related disease, e.g., Aβ-related disease, e.g., Alzheimer's disease, cerebral amyloid angiopathy, inclusion body myositis, macular degeneration, Down's syndrome, Mild Cognitive Impairment, and hereditary cerebral hemorrhage. The therapeutic formulations described hereinbefore, can be incorporated into a pharmaceutical composition containing a pharmaceutically acceptable vehicle and an amount of a therapeutic compound formulated to significantly reduce or prevent gastrointestinal intolerance, in an amount sufficient to treat or inhibit amyloidosis; inhibit amyloid deposition; or prevent or treat amyloid-related disease.

In one embodiment, the pharmaceutical compositions of the invention include a therapeutic compound having the formula 3-amino-1-propanesulfonate/X, where X is an ester or a counter cation, wherein the ester or counter cation includes alcohol radicals or positively charged atoms and moieties, respectively, that do not significantly affect the ability of the therapeutic formulation to reduce or prevent gastrointestinal intolerance. In a preferred embodiment, the cationic group is hydrogen, $H^+$, and the compound is 3-amino-1-propanesulfonic acid. For example, the non-hygroscopic nature of the acid form makes it more stable and desirable as active pharmaceutical ingredient.

In yet another embodiment, the invention is a method of formulating a gastrointestinal intolerance enhanced pharmaceutical composition comprising: combining a pre-selected therapeutic compound with a pharmaceutically acceptable carrier, wherein the therapeutic compound is pre-selected for its ability to significantly reduce or prevent gastrointestinal intolerance, forming a gastrointestinal intolerance enhanced pharmaceutical composition.

The language "gastrointestinal intolerance enhanced pharmaceutical composition" includes pharmaceutical compositions containing therapeutic compounds of the invention that have been chosen by pre-selecting the compound based on its ability to significantly reduce or prevent gastrointestinal intolerance.

IV. Administration

Formulations of the present invention include those suitable for oral administration. The formulations may conveniently be presented in unit dosage form and may be prepared by any methods well known in the art of pharmacy. The amount of active ingredient which can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessarily, shaping the product.

Formulations of the invention suitable for oral administration may be in the form of capsules, cachets, pills, tablets, lozenges (using a flavored basis, usually sucrose and acacia or tragacanth), powders, granules, pellets, e.g., coated (e.g., enteric coated) or uncoated, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules, pellets, and the like), the active ingredient is mixed with one or more pharmaceutically acceptable carriers, such as sodium citrate or dicalcium phosphate, or any of the following: fillers or extenders, such as starches, lactose, sucrose, glucose, mannitol, or silicic acid; binders, such as, for example, carboxymethylcellulose, alginates, gelatin, polyvinyl pyrrolidone, sucrose or acacia; humectants; such as glycerol; disintegrating agents, such as agar-agar, calcium carbonate, potato or tapioca starch, alginic acid, certain silicates, and sodium carbonate; solution retarding agents, such as paraffin; absorption accelerators, such as quaternary ammonium compounds; wetting agents, such as, for example, cetyl alcohol and glycerol monostearate; absorbents, such as kaolin and bentonite clay; lubricants, such as talc, calcium stearate, magnesium stearate, solid polyethylene glycols, sodium lauryl sulfate, and mixtures thereof; and coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols aid the like. The therapeutic compounds of the invention are effective when administered orally. Accordingly, a preferred route of administration is oral administration. The therapeutically active compound may be coated in a material to protect the compound from the action of acids and other natural conditions which may inactivate the compound. The compounds of the invention can be formulated to ensure proper distribution in vivo. For example, the blood-brain barrier (BBB) excludes many highly hydrophilic compounds; and to ensure that the therapeutic compounds of the invention cross the BBB, they can be formulated, for example, in liposomes. For methods of manufacturing liposomes, see, e.g., U.S. Pat. Nos. 4,522,811; 5,374,548; and 5,399,331. The liposomes may comprise one or more moieties which are selectively transported into specific cells or organs ("targeting moieties"), thus providing targeted drug delivery (see, erg., V. V. Ranade (1989) J. Clin. Pharmacol. 29-685). Exemplary targeting moieties include folate or biotin (see, e.g., U.S. Pat. No. 5,416,016 to Low et al.); mannaosides (Umezawa et al., (1988) Biochem. Biophys. Res. Commun. 153:1038); antibodies (P. G. Bloeman et al. (1995) FEBS Lett. 357:140; M. Owais et al. (1995) Antimicrob. Agents Chemother. 39:180); surfactant protein A receptor (Briscoe et al. (1995) Am. J. Physiol. 1233:134); gp120 (Schreier et al. (1994) J. Biol. Chem. 269:9090); see also K. Keinanen; M. L. Laukkanen (1994) FEBS Lett. 346:123; J. J. Killion; I. J. Fidler (1994) Immunomethods 4:273.

To administer the therapeutic compound it may be necessary to coat the compound with, or co-administer the compound with, a material to prevent its inactivation. For example, the therapeutic compound may be administered to a subject in an appropriate carrier, for example, liposomes, or a diluent. Liposomes include water-in-oil-in-water CGF emulsions as well as conventional liposomes (Strejan, et al., J Neuroimmunol. 7, 27 (1984)).

The therapeutic compound can be orally administered, for example, with an inert diluent or an assimilable edible carrier. The therapeutic compound and other ingredients may also be enclosed in a hard or soft shell gelatin capsule, compressed into tablets, or incorporated directly into the subjects diet. For example, therapeutic formulations, such as enteric coated pellets, could be compacted into tablets or encapsulated into hard gelatin capsule. In particular embodiments of the invention, the pellets useful in the present invention may be, for example, 0.05 mm-3 mm, e.g., about 0.8-1.8 mm. Moreover, in certain embodiments these pellets can be formulated to (a) provide for instant or rapid drug release (i.e., have no coating on them); (b) be coated, e.g., to provide for sustained drug release over time; or (C) be coated with an enteric coating for better gastrointestinal tolerability.

The pharmaceutical formulations according to the invention can be provided in any dosage unit (e.g., tablets, capsules, caplets, transdermal patch, etc.); or in two or more of the same or different such units; and/or as individual components of a given dosage unit (e.g., layers, beads, compartments, matrices, coatings, shapes, etc.) which cooperate on administration to achieve the release and/or concentration profile properties desired for any of the embodiments of this invention. Thus, included are single dosage units, such as multi-layer, multi-bead, multi-matrix, multi-compartment forms which achieve, in general, a controlled (e.g., pulsed, sustained, extended, delayed, slow, first order, second order, etc.) release over an entire day, or achieve preferred profiles in accordance with the invention; and multiple dosage units (to be simultaneously or sequentially administered), typically associated together, e.g., in the form of a kit containing the multiple units, identified in a manner which indicates the time of day or relative time order in which the units are to be administered. One of many such kits is a conventional blister pack (or other pouch or container system) containing the multiple units and instructions or notices or indicia regarding the timing and order of administration. Other manners of identifying the time of day and/or order of administration can include unit shape, color, size, etc and combinations thereof.

Formulations for achieving the foregoing dosing regimens are conventional. These can use immediate, controlled, sustained, extended, delayed, pulsatile, osmotic etc. technologies, alone or in combination to achieve the desired regimens. Examples of potential formulations and preparations are contained, for example, in the Handbook of Pharmaceutical Excipients, American Pharmaceutical Association 4$^{th}$ edition, 2003 (Rowe, Sheskey and Weller); Pharmaceutical Dosage Forms: Tablets (Lieberman, Lachman and Schwarts, editors) current edition, published by Marcel Dekker, Inc., as well as Remington's Pharmaceutical Sciences (A. Gennaro, editor, 20th edition, 2000). Where pulses in an extended release capsule or tablet are to be employed, the methods and formulations described in U.S. Pat. No. 5,837,284 can be used, for example, including conventional pulsing techniques, such as enteric or other coatings, osmotic systems, and many others. Where smoother release profiles are to be achieved, conventional sustained or controlled release methods can be used; see, e.g., in R. K. Chang and J. R. Robinson, chapter 4: "Sustained Drug Release from Tablets and Particles Through Coating," in *Pharmaceutical Dosage Forms: Tablets*, volume 3, edited by H. A. Lieberman, L. Lachman, and J. B. Schwartz, Marcel Dekker, Inc., 1991; R. J. Campbell and G. L. Sackett, chapter 3: "Film coating," in *Pharmaceutical Unit Operations: Coating*, edited by K. E. Avis, A. J. Shukla, and R. K. Chang, Interpharm Press, Inc., 1999. All of these disclosures are entirely incorporated by reference herein.

For example, the active agents can be provided in the form of beads, e.g., having a core which is optionally coated with a coating which allows the release of the agent immediately or over time, such as a pharmaceutically acceptable water-insoluble or water soluble film former alone or with a dissolution regulating agent etc. See, e.g., U.S. Pat. No. 4,728,512. A biphasic or multiphasic release profile can be achieved by combining the immediate-release beads with delayed, sustained or other controlled release beads or by providing various extended release beads with differing release profiles.

Beads can be prepared by coating conventional drug-containing cores with a water-insoluble polymer, or a combination of water-insoluble polymers, or a combination of water-insoluble and water-soluble polymers. This may be a combination of layers, or a combination of polymers in a single coating. The resultant beads (or tiny tablets) can then be placed in a capsule. Other than beads in a capsule shell, tablets in a capsule shell (e.g., one or more immediate-release tablet and one or more delayed, sustained release tablet in a capsule shell) also can be used to attain the desired release profile.

Various polymeric materials can be used to achieve the desired type of pattern of release, e.g., immediate, sustained, delayed etc. release. For example, a multiple dosage form (e.g., as discussed below) can deliver rapid and complete dosages of active agent to a recipient multiple times over a period of hours with a single oral administration, if it is desired to combine dosages in a single unit; additionally, doses with sustained or delayed release function can be combined with each other or with doses having immediate release functionality.

Examples of possible bead constructions are plentiful and include the following:

Sugar core bead, coated with active agent and then coated with polymer and/or with mix of active agent and polymer or any different order of such layers on the core, within each case, selected active agent concentrations of components in the layers.

Bead containing active agent core, coated with polymer, and/or with mix of active agent and polymer or any different order of such layers on the core, within each case, selected active agent concentrations of components in the layer.

Tablet or capsule containing multiple types of beads as described above having differing timing of release or different rates of release of active agent.

Matrix beads can also be used, i.e., not having any layers to achieve sustained or delayed release. The components used in such matrices are chosen from conventional sustained release or delayed release polymers.

Details of using the foregoing constructs and others to achieve a desired release profile as discussed above are fully conventional and can be determined by those of skill in the art with at most a few routine parametric experiments, and conventional adjustments, e.g., involving identities of polymers and mixtures thereof, relative amounts of components, coating thicknesses, bead diameters, number of layers and compositions thereof, etc. Thus, for example, for a given construct, in vitro dissolution profiles as described herein can be determined. Fully conventional formulation and dissolution profile adjustments can be made routinely. Formulations having the desired in vitro release profiles produce the desired plasma concentration levels. These plasma profiles will be correlated with the release profiles in view of the usual factors, e.g., in vivo dissolution and absorption properties, active agent half-lives, etc., which correlation is well understood in the art.

Suitable materials which can be used to achieve formulations having such release profiles are well known and include but are not limited to polyvinyl acetate, cellulose acetate, cellulose acetate lattices, cellulose acetate butyrate, cellulose acetate propionate, ethyl cellulose, fatty acids and their esters, alkyl alcohols, waxes, zein (prolamine from corn), and aqueous polymeric dispersions such as the commercially available Eudragit®, Aquacoat®, Surelease®, Kollicoat®, etc., products.

The agent-containing particles may also be incorporated into a tablet, in particular by incorporation into a tablet matrix, which rapidly disperses the particles after ingestion. In order to incorporate these particles into such a tablet, a filler/binder must be added to a tablet that can accept the particles, but will not allow their destruction during the tableting process. Materials that are suitable for this purpose include, but are not limited to, microcrystalline cellulose (e.g., AVICEL®), soy polysaccharide (e.g., EMCOSOY®), pre-gelatinized starches (e.g., STARCH® 1500, NATIONAL® 1551), and polyethylene glycols (e.g., CARBOWAX®). The materials are typically present in the range of 5-75% (w/w), with a preferred range generally of 25-50% (w/w).

In addition, disintegrants can optionally be added in order to disperse the beads once the tablet is ingested. Suitable disintegrants include, but are not limited to: cross-linked sodium carboxylmethyl cellulose (e.g., AC-DI-SOL®), sodium starch glycolate (e.g., EXPLOTAB®, PRIMOJEL®), and cross-linked polyvinylpolypyrrolidone (e.g., Plasone-XL). These materials are typically present in the rate of 3-15% (w/w), with a preferred range generally of 5-10% (w/w).

Lubricants can also optionally be added to assure proper tableting, and these can include, but are not limited to: magnesium stearate, calcium stearate, stearic acid, polyethylene glycol, leucine, glyceryl behanate, and hydrogenated vegetable oil. These lubricants are typically present in amounts from 0.1-10% (w/w), with a preferred range generally of 0.3-3.0% (w/w).

Where immediate release is not desired, for example, various enteric materials, e.g., cellulose acetate phthalate, hydroxypropyl methylcellulose phthalate, polyvinyl acetate phthalate, and the EUDRAGIT® and ACRYLEZE® acrylic polymers, can be used as gastroresistant, enterosoluble coatings for drug release in the intestine when desired. The enteric materials, which are soluble at higher pH values, are frequently used for colon-specific delivery systems and are entirely conventionally employable in the systems of this invention. The enteric polymers used in this invention can also be modified conventionally by mixing with other known coating products that are not pH sensitive. Examples of such coating products include the neutral methacrylic acid esters with a small portion of trimethylammonioethyl methacrylate chloride, which are commercially available, e.g., EUDRAGIT® RS and EUDRAGIT® RL; neutral ester dispersions without any functional groups, e.g., EUDRAGIT® NE30D and EUDRAGIT® NE30; and other pH independent coating products.

A conventional protective coating layer may also be applied immediately outside the core, either a drug-containing matrix core or a drug-layered core, by conventional coating techniques such as pan coating or fluid bed coating using solutions of polymers in water or suitable organic solvents or by using aqueous polymer dispersions. Suitable materials for the protective layer include cellulose derivatives such as hydroxyethyl cellulose, hydroxypropyl cellulose, hydroxypropyl methylcellulose, polyvinylpyrrolidone, polyvinylpyrrolidone/vinyl acetate copolymer, ethyl cellulose aqueous dispersions, polyvinyl acetate (e.g., AQUACOAT®, SURELEASE®g), EUDRAGIT®'s, OPADRY® and the like. Typical coating levels are from 1 to 6%, in general, preferably 2-4% (w/w).

An overcoating layer can further optionally be applied to the compositions of the present invention. OPADRY®, OPADRY II® (Colorcon) and corresponding color and colorless grades from Colorcon can be used to protect the pellets from being tacky and provide colors to the product. Typical levels of protective or color coating are from 1 to 6%, in general preferably 2-3% (w/w). Many ingredients can be incorporated into the overcoating formula, for example to provide a quicker (immediate) release, such as plasticizers: acetyltriethyl citrate, triethyl citrate, acetyltributyl citrate, dibutylsebacate, triacetin, polyethylene glycols, propylene glycol and the others; lubricants: talc, colloidal silica dioxide, magnesium stearate, calcium stearate, titanium dioxide, magnesium silicate, and the like.

Optional modifying components of a protective layer which can be used over the enteric or other coatings include a water penetration barrier layer (semi-permeable polymer) which can be successively coated after the enteric or other coating to reduce the water penetration rate through the enteric coating layer and thus increase the lag time of the drug release. Sustained-release coatings commonly known to one skilled in the art can be used for this purpose by conventional coating techniques such as pan coating or fluid bed coating using solutions of polymers in water or suitable organic solvents or by using aqueous polymer dispersions. For example, the following materials can be used, but not limited to: cellulose acetate, cellulose acetate butyrate, cellulose acetate propionate, ethyl cellulose, fatty acids and their esters, waxes, zein, and aqueous polymer dispersions such as EUDRAGIT®'s, e.g., RS, RL 30D, NE 30D, AQUACOAT®, SURELEASE®, cellulose acetate latex, etc. Combinations of the above polymers and hydrophilic polymers such as hydroxyethyl cellulose, hydroxypropyl cellulose (KLUCEL®, Hercules Corp.), hydroxypropyl methylcellulose (METHOCEL®, Dow Chemical Corp.), and polyvinylpyrrolidone can also be used.

For oral therapeutic administration, the therapeutic compound may be incorporated with excipients and used in the form of ingestible tablets, buccal tablets, troches, capsules, elixirs, suspensions, syrups, wafers, and the like. The percentage of the therapeutic compound in the compositions and preparations may, of course, be varied. The amount of the therapeutic compound in such therapeutically useful compositions is such that a suitable dosage will be obtained.

The term "pharmaceutically acceptable carrier" includes a pharmaceutically acceptable material, composition or vehicle, such as a liquid or solid filler, diluent, excipient, solvent or encapsulating material, involved in carrying or transporting a compound(s) of the present invention within or to the subject such that it can perform its intended function. Typically, such compounds are carried or transported from one organ, or portion of the body, to another organ, or portion of the body. Each carrier must be "acceptable" in the sense of being compatible with the other ingredients of the formulation, not injurious to the patient, and in the sense that it does not affect the ability of the therapeutic formulation to reduce or prevent gastrointestinal intolerance. Some examples of materials which can serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations known in the art.

The term "vehicle" is intended to encompass any substance which is pharmaceutically or pharmacologically acceptable.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: water soluble antioxidants, such as ascorbic acid, cysteine hydrochloride, sodium bisulfate, sodium metabisulfite, sodium sulfite and the like; oil-soluble antioxidants, such as ascorbyl palmitate, butylated hydroxyanisole (BHA), butylated hydroxytoluene (BHT), lecithin, propyl gallate, alpha-tocopherol, and the like; and metal chelating agents, such as citric acid, ethylenediamine tetraacetic acid (EDTA), sorbitol, tartaric acid, phosphoric acid, and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills, pellets, and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes or microspheres. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents, and/or may contain agents that release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Powders can contain, in addition to a compound of this invention, excipients such as lactose, talc, silicic acid, aluminum hydroxide, calcium silicates and polyamide powder, or mixtures of these substances.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents that delay absorption such as aluminum monostearate and gelatin.

The compositions of this invention can also be administered topically to a subject, e.g., by the direct laying on or spreading of the composition on the epidermal or epithelial tissue of the subject, or transdermally via a "patch". Such compositions include, for example, lotions, creams, solutions, gels and solids. These topical compositions preferably comprise an effective amount, usually at least about 0.1%, and preferably from about 1% to about 5%, of a compound of the invention. Suitable carriers for topical administration preferably remain in place on the skin as a continuous film, and resist being removed by perspiration or immersion in water. Generally, the carrier is organic in nature and capable of having the therapeutic compound dispersed or dissolved therein. The carrier may include pharmaceutically acceptable emollients, emulsifiers, thickening agents, solvents and the like.

In one embodiment, the pharmaceutical formulation comprises greater than about 0.1%, e.g., greater than about 1%, e.g., greater than about 2%, e.g., greater than about 3%, e.g., greater than about 4%, e.g., greater than about 5%, e.g., greater than about 10%, e.g., greater than about 20%, e.g., greater than about 30%, e.g., greater than about 40%, e.g., greater than about 50%, e.g., greater than about 60%, e.g., greater than about 70%, e.g., greater than about 80%, e.g., greater than about 90%, e.g., greater than about 95%, e.g., greater than about 99%, of a therapeutic compound, e.g., an alkylsulfonic acid, e.g., a 3-amino-1-propanesulfonic acid compound, by weight of the formulation. In a specific embodiment, the pharmaceutical formulation comprises about 12.6%±0.5% of the therapeutic compound by weight of the formulation. In another specific embodiment, the pharmaceutical formulation comprises about 95.2%±0.5% of the therapeutic compound by weight of the formulation. The remainder of the pharmaceutical formulation may be comprised of additional agents as described herein.

In another embodiment, the pharmaceutical formulation comprises greater than about 1%, e.g., greater than about 2%, e.g., greater than about 3%, e.g., greater than about 4%, e.g., greater than about 5%, e.g., greater than about 6%, e.g., greater than about 7%, e.g., greater than about 8%, e.g., greater than about 9%, e.g., greater than about 10%, e.g., greater than about 20%, e.g., greater than about 30%, e.g., greater than about 40%, e.g., greater than about 50%, e.g., greater than about 60%, e.g., greater than about 70%, e.g., greater than about 80%, e.g., greater than about 90%, e.g., greater than about 95%, e.g., greater than about 99%, of an additional agent, e.g., an agent that modifies the release of the therapeutic compound or an enteric coating, by weight of the formulation. It should be understood that these percentages are ranges that apply to the one or more additional agents of the formulation, independently or in combination. In certain embodiments the additional agent may be used in the therapeutic formulation to impart favorable properties, e.g., to reduce or prevent gastrointestinal intolerance independently or in conjunction with other methods of reducing or preventing intolerance. Exemplary additional agents are described herein. For example, to protect against any possible gastrointestinal intolerance that could result from the therapeutic formulation, the tablets may be enteric-coated or a modified-release agent may be added to control any rapid release of the therapeutic compound in the stomach or intestine. In a specific embodiment, the pharmaceutical formulation comprises about 9.3%±0.5% of the additional agent by weight of the formulation. In another specific embodiment, the pharmaceutical formulation comprises about 8.8%±0.5% of the additional agent by weight of the formulation. In another specific embodiment, the pharmaceutical formulation comprises about 5.6%±0.5% of the additional agent by weight of the formulation.

In specific embodiments of the invention, the therapeutic compound is administered with an agent selected from the group consisting of an agent that modifies the release of the therapeutic compound, e.g., hydroxypropylmethylcellulose (HPMC), a glidant/diluent, e.g., silicated mycrocrystalline, a filler, e.g., dibasic calcium phosphate, a binder/desintegrant, e.g., Starch® 1500, a lubricant, e.g., stearic acid powder or magnesium stearate, a subcoat, e.g., Opadry® II White, a topcoat, e.g., Opadry® II White or Opadry® Clear, an enteric coat, e.g., Acryleze®, and any combination thereof. The following materials are available from Colorcon (West Point, Pa.): Starchy 1500, Opadry® II White, Opadry® Clear, Acryleze®. Several embodiments of the invention are discussed below in the Examples section.

Equivalents

Those skilled in the art will recognize, or be able to ascertain using no more than routine experimentation and the content of the instant specification, numerous equivalents to the specific procedures, embodiments, claims, and examples described herein. Such equivalents are considered to be within the scope of this invention and covered by the claims appended hereto.

It is to be understood that wherever values and ranges are provided herein, e.g., in ages of subject populations, dosages, and blood levels, all values and ranges encompassed by these values and ranges, are meant to be encompassed within the scope of the present invention. Moreover, all values that fall within these ranges, as well as the upper or lower limits of a range of values are also contemplated by the present application.

INCORPORATION BY REFERENCE

Figure 1:
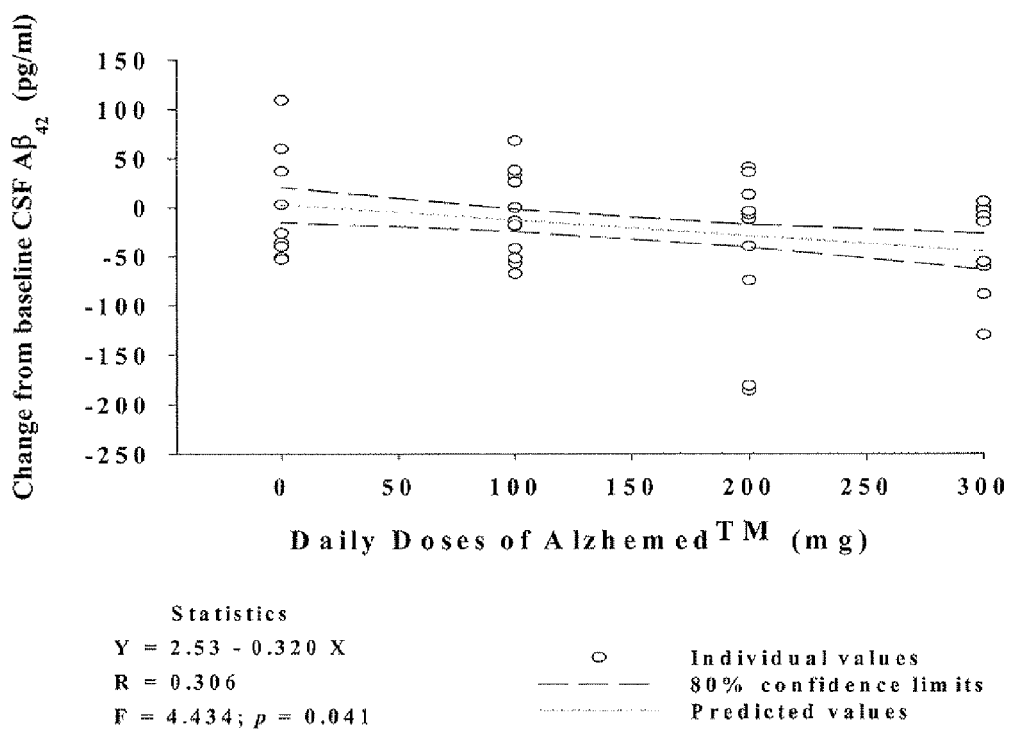
FIG. 1 Change from Baseline CSF A$\beta_{42}$ versus 3-APS doses

The contents of all references, issued patents, and published patent applications cited throughout this application are hereby incorporated by reference. It should be understood that the use of any of the compounds described herein or in the applications identified in "The Related Applications" Section are within the scope of the present invention and are intended to be encompassed by the present invention and are expressly incorporated herein at least for these purposes, and are furthermore expressly incorporated for all other purposes

EXAMPLES

The invention is further illustrated by the following examples which should not be construed as further limiting the subject invention.

Example 1

Gelatin Capsules for Oral Administration

The unit formula of 100 and 400 mg white gelatin capsules is presented in Table 2.

TABLE 2

Unit Formula for 100 and 400 mg Gelatin Capsules

| Ingredient | Grade | Function | Capsules (mg/capsule) 100 mg | 400 mg |
|---|---|---|---|---|
| 3-amino-1-propanesulfonic acid, sodium salt | MS* | Active Ingredient | 100 mg | 400 mg |
| Calcium carbonate | NF | Filler | 4.45 | 17.8 |
| Magnesium stearate | NF | Lubricant | 0.55 | 2.2 |

*MS: Manufacturer's Standard,
NF: National Formulary;
USP: United States Pharmacopoeia.

Results from certain studies have shown that the administration of 3-amino-1-propanesulfonic acid sodium salt in solid dosage form (capsules) was associated with gastrointestinal symptoms (i.e. nausea and vomiting). Further investigations revealed that the gastrointestinal symptoms were produced, at least in part, by a local irritation due to the high pH generated during the dissolution of amino-1-propanesulfonic acid sodium salt into the stomach. Additional experiments in dogs (in solid dosage form) have shown that the free acid was better tolerated than the sodium salt form. Furthermore, the non-hygroscopic nature of the acid form makes it desirable as active pharmaceutical ingredient. To further protect against any possible gastrointestinal intolerance that could result from the acid form, the tablets were enteric-coated and a modified-release agent was added to control any rapid release of the drug in the stomach and the intestine, respectively.

Example 2

Enteric-Coated Tablets

The 100 and 400 mg white enteric-coated tablets were prepared according to a formulation in which the drug substance produced by a process utilizing ion-exchange to remove sodium was densified by granulation with water because of its low density and fluffiness. The unit formula of the 100 and 400 mg Enteric-Coated tablets is presented in Table 3.

TABLE 3

Unit Formula of 100 and 400 Enteric-Coated Tablets

| Ingredient | Grade | Function | Enteric-Coated Tablet (mg/tablet) 100 mg | 400 mg |
|---|---|---|---|---|
| Core: | | | | |
| 3-amino-1-propanesulfonic acid | MS* | Active Ingredient | 100.00 | 400.00 |
| Silicated mycrocrystalline cellulose | NF | Glidant/Diluent | 350.00 | 70.00 |
| Dibasic calcium phosphate | USP | Filler | 158.40 | 112.00 |
| Hydroxypropylmethylcellulose (HPMC) | USP | Drug Release Modifier | 70.00 | 70.00 |
| Starch ® 1500 | NF | Binder/Desintegrant | 11.10 | 37.50 |
| Stearic acid powder | NF | Lubricant | 7.00 | 7.00 |
| Magnesium stearate | NF | Lubricant | 1.80 | 0.018 |

TABLE 3-continued

Unit Formula of 100 and 400 Enteric-Coated Tablets

| Ingredient | Grade | Function | Enteric-Coated Tablet (mg/tablet) | |
|---|---|---|---|---|
| | | | 100 mg | 400 mg |
| Coating: | | | | |
| Opadry ® II White | MS* | Subcoat | 14.00 | 14.00 |
| Acryleze ® | MS* | Enteric Coat | 42.00 | 42.00 |
| Total Weight: | | | 756.00 | 756.00 |

*MS: Manufacturer's Standard,
NF: National Formulary;
USP: United States Pharmacopoeia.

In vitro (dissolution rate) and PK data from 100 mg enteric-coated tablets indicated that these tablets would result in acceptable PK and good tolerability.

Example 3

Modified-Release Coated Tablets

Clinical studies indicated that the role of the enteric-coating and drug release modifier would be significant in the pharmacokinetic (PK) profile of the drug product as well as its tolerability. Accordingly, in order to give particular pharmaceutical performance in terms of PK, tolerability and product stability, drug release modifier was formulated into the tablet.

To improve physical stability of the product in terms of film coating acceptability and moisture protection capability, under accelerated conditions, the enteric-coating system was modified by the increase in the amount of enteric-coating and the addition of a topcoat.

A 50 mg strength modified-release coated tablet consisting of bulk substance (3-amino-1-propanesulfonic acid) and inactive ingredients (silicated mycrocrystalline cellulose, dibasic calcium phosphate, hydroxypropylmethylcellulose, starch, stearic acid, magnesium stearate, as well as Opadry® II white (subcoat and topcoat) and Acryleze®) was prepared. The unit formula of the 50 mg modified-release coated tablet is provided in Table 4.

TABLE 4

Unit Formula of 50 mg Modified-Release Coated Tablets

| Ingredient | Grade | Function | Quantity per tablet (mg) | Quantity per batch (kg) |
|---|---|---|---|---|
| Core: | | | | |
| 3-amino-1-propanesulfonic acid | MS* | Active Ingredient | 50.00 | 0.500 |
| Silicated mycrocrystalline cellulose | NF | Glidant/Diluent | 174.73 | 1.746 |
| Dibasic calcium phosphate | USP | Filler | 79.42 | 0.794 |
| Hydroxypropylmethylcellulose (HPMC) | USP | Drug Release Modifier | 35.00 | 0.350 |
| Starch ® 1500 | NF | Binder/Desintegrant | 5.55 | 0.056 |
| Stearic acid powder | NF | Lubricant | 3.50 | 0.036 |
| Magnesium stearate | NF | Lubricant | 1.80 | 0.018 |
| Weight: | | | 350.00 | 3.500 |
| Coating: | | — | | |
| Opadry ® II White | MS* | Subcoat | 7.00 | 0.072 |
| Acryleze ® | MS* | Enteric Coat | 35.00 | 0.360 |
| Opadry ® Clear | MS* | Topcoat | 3.50 | 0.036 |
| Total Weight: | | | 395.50 | 3.974 |

*MS: Manufacturer's Standard,
NF: National Formulary;
USP: United States Pharmacopoeia.

Example 4

Modified-Release Coated Tables

A slight modification to the coating in the formulation of Example 3 was made: the Opadry® Clear used as the topcoat in Example 3 was replaced by Opadry® II White, which is also used for the subcoat. Like Opadry® Clear, Opadry® II White is an HPMC-based preparation which functions in a sealing capacity and therefore equally functions to enhance the moisture protection capability of the enteric coat (Acryleze®). The coating system, change of the topcoat was a process change that may be convenient for the scale-up of the product formulation size, i.e., to facilitate the transition from applying one coat to the other during the coating process by preventing clogging of spray guns during the transition from the enteric coating step to the topcoat application step during the coating process. The unit formula for the 50 mg modified-release coated tablets are represented in Table 5.

TABLE 5

Unit Formula of 50 mg Modified-Release Coated Tablets

| Ingredient | Grade | Function | Quantity per tablet (mg) | Quantity per batch (kg) |
|---|---|---|---|---|
| Core: | | | | |
| 3-amino-1-propanesulfonic acid | MS* | Active ingredient | 50.00 | 0.500 |
| Silicated mycrocrystalline cellulose | NF | Glidant/Diluent | 174.73 | 1.746 |
| Dibasic calcium phosphate | USP | Filler | 79.42 | 0.794 |
| Hydroxypropylmethylcellulose (HPMC) | USP | Drug Release Modifier | 35.00 | 0.350 |
| Starch ® 1500 | NF | Binder/Desintegrant | 5.55 | 0.056 |
| Stearic acid powder | NF | Lubricant | 3.50 | 0.036 |
| Magnesium stearate | NF | Lubricant | 1.80 | 0.018 |
| Weight: | | | 350.00 | 3.500 |
| Coating: | | — | | |
| Opadry ® II White | MS* | Subcoat | 7.00 | 0.072 |
| Acryleze ® | MS* | Enteric Coat | 35.00 | 0.360 |
| Opadry ® II White | MS* | Topcoat | 3.50 | 0.036 |
| Total Weight: | | | 395.50 | 3.974 |

*MS: Manufacturer's Standard,
NF: National Formulary;
USP: United States Pharmacopoeia.

The dissolution profile, carried out according to the USP method (USP 25, Method B, p. 2017), indicates that the dissolution rate for both of the 50 mg modified release coated tablets (Examples 3 and 4) is comparable.

In addition, in order to improve the stability of appearance i.e., whiteness, the following modified release coated tablet formulation was prepared, i.e., with increased Opadry® II White:

TABLE 6

Unit Formula of 50 mg Modified-Release Coated Tablets

| Ingredient | Grade | Function | Quantity per tablet (mg) | Quantity per batch (kg) |
|---|---|---|---|---|
| Core: | | | | |
| 3-amino-1-propanesulfonic acid | MS* | Active ingredient | 50.00 | 0.500 |
| Silicated mycrocrystalline cellulose | NF | Glidant/Diluent | 174.73 | 1.746 |
| Dibasic calcium phosphate | USP | Filler | 79.42 | 0.794 |
| Hydroxypropylmethylcellulose (HPMC) | USP | Drug Release Modifier | 35.00 | 0.350 |
| Starch ® 1500 | NF | Binder/Desintegrant | 5.55 | 0.056 |
| Stearic acid powder | NF | Lubricant | 3.50 | 0.036 |
| Magnesium stearate | NF | Lubricant | 1.80 | 0.018 |
| Weight: | | | 350.00 | 3.500 |
| Coating: | | — | | |
| Opadry ® II White | MS* | Subcoat | 7.00 | 0.072 |
| Acryleze ® | MS* | Enteric Coat | 35.00 | 0.360 |
| Opadry ® II White | MS* | Topcoat | 7.00 | 0.072 |
| Total Weight: | | | 399.00 | 4.004 |

*MS: Manufacturer's Standard,
NF: National Formulary;
USP: United States Pharmacopoeia.

Example 5

Mass Spectroscopy Assay

The binding of a compound to amyloid fibrils may be measured using a mass spectroscopy ("MS") assay as described herein below.

Samples are prepared as aqueous solutions containing 20% ethanol, 200 µM of a test compound and 20 µM of solubilized Aβ40. The pH value of each sample is adjusted to 7.4 (±0.2) by addition of 0.1% aqueous sodium hydroxide. The solutions are then analyzed by electrospray ionization mass spectroscopy using a Waters ZQ 4000 mass spectrometer. Samples are introduced by direct infusion at a flow-rate of 25 µL/min within 2 hours after sample preparation. The source temperature is kept at 70° C. and the cone voltage is 20 V for all the analysis. Data is processed using Masslynx 3.5 software.

The resulting MS assay data provides insight into the ability of compounds to bind to Aβ.

Example 6

Modified-Release Coated Tablets-Selected Dose Strengths

Two additional dose strengths were prepared for the modified release coated tablet formulation of Example 4 (Table 6), i.e., 100 mg and 150 mg tablets. The larger dose strengths of the modified release coated tablets were selected and were particularly useful for the administration of therapeutically effective doses larger than 50 mg. In a specific embodiment, subjects that require a larger dose would require a smaller number of pills to attain a prescribed dose, which would in turn lead to improved patient compliance. Accordingly, in certain embodiments of the invention, the dose is selected to enhance patient compliance.

For that reason, the 100 mg and 150 mg strength modified-release coated tablets consisting of bulk substance (3-amino-1-propanesulfonic acid) and inactive ingredients (silicated mycrocrystalline cellulose, dibasic calcium phosphate, hydroxypropylmethylcellulose, starch, stearic acid, magnesium stearate, as well as Opadry® II white (subcoat and topcoat) and Acryleze®) were prepared. The unit formula of the 100 mg modified-release coated tablet is provided in Table 7.

TABLE 7

Unit Formula of 100 mg Modified-Release Coated Tablets

| Ingredient | Grade | Function | Quantity per tablet (mg) | Proportion (%) |
|---|---|---|---|---|
| Core: | | | | |
| 3-amino-1-propanesulfonic acid | MS* | Active ingredient | 100.00 | 28.6 |
| Silicated mycrocrystalline cellulose | NF | Glidant/Diluent | 140.35 | 40.1 |
| Dibasic calcium phosphate | USP | Filler | 63.80 | 18.2 |
| Hydroxypropylmethylcellulose (HPMC) | USP | Drug Release Modifier | 35.00 | 10.0 |
| Starch® 1500 | NF | Binder/Desintegrant | 5.55 | 1.6 |
| Stearic acid powder | NF | Lubricant | 3.50 | 1.0 |
| Magnesium stearate | NF | Lubricant | 1.80 | 0.5 |
| Weight: | | | 350.00 | 100.0 |
| Coating**: | | — | | |
| Opadry® II White | MS* | Subcoat | 7.00 | 2.0 |
| Acryleze® | MS* | Enteric Coat | 35.00 | 10.0 |
| Opadry® II White | MS* | Topcoat | 7.00 | 2.0 |
| Total Weight: | | | 399.00 | 114.0 |

*MS: Manufacturer's Standard,
NF: National Formulary;
USP: United States Pharmacopoeia.
**Several processing steps involved the evaporation of purified water The unit formula of the 150 mg modified-release coated tablet is provided in Table 8.

TABLE 8

Unit Formula of 150 mg Modified-Release Coated Tablets

| Ingredient | Grade | Function | Quantity per tablet (mg) | Proportion (%) |
|---|---|---|---|---|
| Core: | | | | |
| 3-amino-1-propanesulfonic acid | MS* | Active ingredient | 150.00 | 28.6 |
| Silicated mycrocrystalline cellulose | NF | Glidant/Diluent | 210.53 | 40.1 |
| Dibasic calcium phosphate | USP | Filler | 95.69 | 18.2 |
| Hydroxypropylmethylcellulose (HPMC) | USP | Drug Release Modifier | 52.50 | 10.0 |

TABLE 8-continued

Unit Formula of 150 mg Modified-Release Coated Tablets

| Ingredient | Grade | Function | Quantity per tablet (mg) | Proportion (%) |
|---|---|---|---|---|
| Starch ® 1500 | NF | Binder/Desintegrant | 8.33 | 1.6 |
| Stearic acid powder | NF | Lubricant | 5.25 | 1.0 |
| Magnesium stearate | NF | Lubricant | 2.70 | 0.5 |
| Weight: | | | 525.00 | 100.0 |
| Coating**: | | | — | |
| Opadry ® II White | MS* | Subcoat | 10.50 | 2.0 |
| Acryleze ® | MS* | Enteric Coat | 52.50 | 10.0 |
| Opadry ® II White | MS* | Topcoat | 10.50 | 2.0 |
| Total Weight: | | | 598.50 | 114.0 |

*MS: Manufacturer's Standard,
NF: National Formulary;
USP: United States Pharmacopoeia.
**Several processing steps involved the evaporation of purified water Pharmacokinetics Analysis In the following examples and elsewhere herein, terms are as defined below. The pharmacokinetic parameters were derived by non-compartmental analysis using WinNonlin Version 2.1.

$C_{max}$—the maximum observed plasma concentration.

$T_{max}$—the time of occurrence of $C_{max}$.

$AUC_{0-t}$—the area under the plasma concentration versus time curve from time zero to the last sampling time at which concentrations were at or above the limit of quantification, calculated by the linear trapezoidal rule.

$AUC_\infty$—the area under the plasma concentrations versus time curve from time zero to infinity, calculated from $AUC_{0-t}+(C_{last}/\lambda_z)$, where $C_{last}$ is the last observed quantifiable concentration and $\lambda z$ is the apparent terminal rate constant.

$t_{1/2}$—the apparent terminal half-life, calculated from $\ln 2\lambda_z$.

Example 7

The pharmacokinetic profile and the effect of food on single rising oral doses of 3-APS free acid (modified-release enteric-coated tablet, as described in Table 3 above, hereinafter "NC-758") in healthy male young (18-45 years) volunteers was determined. The pharmacokinetics of a single oral dose of NC-758 was also determined in a group of healthy male elderly (≥55 years old) volunteers. The test was a randomized, double-blind, placebo-controlled study to assess the pharmacokinetic profile of 4 single rising oral doses of NC-758 in healthy young (18-45 years) male subjects. Blood samples were collected during 24 h following dosing. Plasma concentrations of 3-APS were determined using a validated LC-MS/MS method. Results are shown in Table 9.

TABLE 9

Pharmacokinetic Parameters of 3-APS following Single Oral Administration of 100, 200, 300 and 400 mg to Young Male Subjects and 200 mg to Elderly Male Subjects (Fasted state)

| Dose | $C_{max}$ (ng/mL) | $C_{max}$ Ranges (ng/mL) | $T_{max}$ (h) | $AUC_{0-Tlast}$ (ng · h/mL) | $AUC_\infty$* (ng · h/mL) |
|---|---|---|---|---|---|
| Young (18-45 years) | | | | | |
| 100 mg (n = 5)[a] | 410 | Min 276 Max 629 | 5 (5-5) | 1392 (567-2293) | 1421 (584-2314) |
| 200 mg (n = 6) | 661 | Min 289 Max 979 | 5 (3-5) | 2898 (1342-4214) | 2492 (1375-3677) |
| 300 mg (n = 5) | 904 | Min 666 Max 1220 | 5 (5-6) | 3999 (2621-5130) | 4464 (3826-5331) |
| 400 mg (n = 4) | 5367 | Min 3630 Max 7300 | 2 (1.5-5) | 15966 (14153-18264) | NC |
| Elderly (>55 years) | | | | | |
| 200 mg (n = 6) | 1094 | Min 871 Max 1250 | 5 (5-6) | 4882 (3370-6573) | 5757[a] |

Values are the mean except for $T_{max}$ which is the median; Min/Max values for Cmax are those observed for individuals; and for AUC and Tmax, where available, minimum and maximum for individuals are in parentheses
*Parameters derived only for subjects for whom the elimination rate constant could be estimated;
NC: Not calculated
[a]Calculated for one individual only.

Example 8

The pharmacokinetic profile of multiple rising oral doses of 3-APS free acid (NC-758 of Table 3 above) in healthy male young subjects (18-45 years) and healthy male and female elderly (≥55 years) subjects was assessed. The pharmacokinetic profile of a titrated multiple oral rising dose regimen of NC-758 was also assessed in one group of healthy male young (18-45 years) subjects. Finally, the pharmacokinetics of a single dose of NC-758 administered in two different oral formulations (modified-release enteric-coated vs. immediate-release uncoated tablet) was compared in one group of healthy male and female elderly (≥55 years) subjects. Part I was a randomized, double-blind, placebo-controlled study to assess the pharmacokinetic profile of 2 multiple rising oral doses of NC-758 in healthy young (18-45 years) male subjects. Part II was a randomized, single-blind, two-period crossover study to compare the pharmacokinetic profile of a single dose of 3-APS administered in two different oral formulations, one being the enteric-coated NC-758 of Table 3 above and the other being an uncoated formulation, in healthy male and female elderly (≥55 years) subjects. In Part I, blood samples were collected through 24 h after the first dose on Day 1, before each morning dose on Days 2 to 11, and through 48 h after the final dose on Day 12. The results are shown in Table 10. For Part II, blood samples were collected through 36 and 48 h, respectively. Plasma concentrations of 3-APS were determined using a validated LC-MS/MS method. The results are shown in Table 11.

years) volunteers. The test was an open label, three-period crossover study to assess the pharmacokinetic profile of 3 single oral doses of NC-758-1 in healthy elderly (≥55 years) male and female subjects. The blood samples were collected during 24 h following dosing. Plasma concentrations of 3-APS were determined using a validated LC-MS/MS method. The results are shown in Table 12.

TABLE 10

Part I (Escalating Dose) - Pharmacokinetic Parameters of 3-APS following Single and Repeated Oral Administration of 100 and 200 mg to Young Male Subjects and 200 mg to Elderly Male and Female Subjects (Fasted state)

| Dose | $C_{max}$ (ng/mL) | $C_{max}$ Ranges (ng/mL) | $T_{max}$ (h) | $AUC_{0-12\,h}$ (ng · h/mL) | $AUC_\infty$* (ng · h/mL) |
|---|---|---|---|---|---|
| Young (18-45 years) | | | | | |
| Day 1 | | | | | |
| 100 mg BID (n = 6) | 282 | Min 148 Max 419 | 6 (3-8) | 1326 (793-1964) | 1017 (828-1207) |
| 200 mg BID (n = 6) | 517 | Min 355 Max 733 | 4 (2.5-8) | 2865 (1306-4644) | 3206 (2136-4275) |
| Day 12 | | | | | |
| 100 mg BID (n = 6) | 256 | Min 141 Max 445 | 2.5 (0-6) | 1434 (865-1967) | NC |
| 200 mg BID (n = 5) | 581 | Min 284 Max 974 | 4 (2.5-6) | 4152 (1801-7980) | NC |
| Elderly (≥55 years) | | | | | |
| Day 1 | | | | | |
| 200 mg BID (n = 6) | 897 | Min 393 Max 1976 | 6 (2-6) | 5020 (2250-9282) | 5503 (2509-9731) |
| Day 12 | | | | | |
| 200 mg BID (n = 6) | 880 | Min 561 Max 1193 | 5 (0.5-6) | 6287 (3630-10505) | NC |

Values are the mean except for $T_{max}$ which is the median; Min/Max values for Cmax are those observed for individuals; and for AUC and Tmax, where available, minimum and maximum for individuals are in parentheses
*Parameters derived only in subjects for whom the elimination rate constant could be estimated
(—): No range since n = 1;
NC: Not calculated

TABLE 11

Part II (Crossover Formulation Effect) - Pharmacokinetic Parameters of 3-APS following Single Oral Administration of 100 mg as Enteric-Coated or Uncoated Formulation to Elderly Male Subjects (Fasted state)

| Formulation | $C_{max}$ (ng/mL) | $C_{max}$ Ranges (ng/mL) | $T_{max}$ (h) | $AUC_{0-Tlast}$ (ng · h/mL) | $AUC_\infty$* (ng · h/mL) |
|---|---|---|---|---|---|
| Enteric-Coated (n = 4) | 516 | Min 166 Max 806 | 5 (4-5) | 2197 (709-3434) | 2114 (747-3482) |
| Uncoated (n = 2) | 770 | Min 546 Max 994 | 2 (2-2) | 2770 (2254-3286) | 2819 (2284-3354) |

Values are the mean except for $T_{max}$ which is the median; Min/Max values for Cmax are those observed for individuals; and for AUC and Tmax, where available, minimum and maximum for individuals are in parentheses
*Parameters derived only for subjects for whom the elimination rate constant could be estimated Example 9

The pharmacokinetic profile and the effect of food on single oral doses of 3-APS free acid (modified-release enteric-coated tablet as described in Table 5 above, hereinafter "NC-758-1") in healthy male and female elderly (≥55

TABLE 12

Pharmacokinetic Parameters of 3-APS following Single Oral Administration of 50, 100 and 150 mg to Elderly Male and Female Subjects (Fasted state)

| Dose | $C_{max}$ (ng/mL) | $C_{max}$ Ranges (ng/mL) | $T_{max}$ (h) | $AUC_{0-t}$ (ng · h/mL) | $AUC_\infty$* (ng · h/mL) |
|---|---|---|---|---|---|
| 50 mg (n = 9) | 469 | Min 222 Max 842 | 5 (5-6) | 1537 (659-2445) | 1566 (694-2473) |
| 100 mg (n = 9) | 745 | Min 442 Max 1182 | 5 (3-5) | 3128 (1338-5493) | 2871 (1362-4289) |
| 150 mg (n = 8) | 1029 | Min 477 Max 1434 | 5 (4-10) | 5303 (2450-8525) | 4497 (2477-5530) |

Values are the mean except for $T_{max}$ which is the median; Min/Max values for Cmax are those observed for individuals; and for AUC and Tmax, where available, minimum and maximum for individuals are in parentheses
*Parameters derived only for subjects for whom the elimination rate constant could be estimated Example 10

A multicenter, randomized, double-blind, placebo-controlled and parallel designed study has been completed with NC-758-1 from Table 5 above in patients suffering from mild to moderate Alzheimer's Disease (AD). This study included assessing the pharmacokinetic/pharmacodynamic profile in AD patients.

A total of fifty-eight (58) mild to moderate AD patients (MMSE scores=13 to 26) were enrolled from 6 centers in the United States. Patients were randomized to receive in 1:1:1:1 ratio of NC-758-1 at 50, 10, 150 mg BID or placebo BID for 12 weeks. Study medication was administered orally (tablet). Each patient was evaluated on 6 occasions at screening, baseline [Week 0], weeks 2, 4, 8 and 12. Blood samples were collected from each patient prior to dosing and at specified time points through 12 h post-dose after the first dose (Week 0) and the last dose (Week 12). Blood samples were also collected prior to the first dose of the day during Week 2, 4 and 8 visits. See Table 13.

TABLE 13

Pharmacokinetic Parameters of 3-APS after Single (Week 0) or Repeated (Week 12) Oral Administration of Alzhemed ™ to AD Patients during 12 Weeks

| Dose | $C_{max}$ (ng/mL) | $T_{max}$ (h) | $AUC_{0-t}$* (ng · h/mL) | $AUC_\infty$** (ng · h/mL) |
|---|---|---|---|---|
| Week 0 | | | | |
| 50 mg BID | 310 | 6 | 1321 | 1396 |
| (n = 15) | (27-776) | (2-9) | (126-4259) | (157-4311) |
| 100 mg BID | 618 | 4.7 | 2467 | 2569 |
| (n = 16) | (220-1666) | (2-8) | (829-5123) | (861-5385) |
| 150 mg BID | 624 | 6 | 2792 | 3418 |
| (n = 14) | (14-1875) | (2-12) | (75-9042) | (670-9627) |
| Week 12 | | | | |
| 50 mg BID | 451 | 3 | 1975 | NC |
| (n = 15) | (77-1150) | (0-9) | (311-5421) | |
| 100 mg BID | 538 | 3.5 | 2590 | NC |
| (n = 14) | (83-901) | (0-8) | (638-4711) | |
| 150 mg BID | 639 | 3 | 3570 | NC |
| (n = 11) | (413-1130) | (0-9) | (1586-7432) | |

Values are the mean except for $T_{max}$ which is the median; Minimum and Maximum values for Cmax, AUCs and Tmax are provided in the parentheses and are those observed for individuals, where available;
*or $AUC_{ss}$ for Week 12
**Parameters derived only in patients for whom the elimination rate constant could be estimated
NC: Not calculated Example 11

The patients from the clinical studies in Example 10 were offered NC-758-1 at 150 mg BID for an additional 17 months (thus, 20 months total) in an open-label study. Nineteen mild to moderate AD patients completed the study. Psychometric tests (ADAS-cog) were performed at each visit, that is every 3 months for the first 9 months and every 4 months for the last 12 months. Overall, approximately 70% of the mild AD patients had stabilized or improved cognitive function tests after 20 months. The mild to moderate patients (n=19) showed an average ADAS-cog score of +6.2 points, as opposed to +11.9 points on average in comparable historical controls with AD. A subset of mild AD patients (n=10) responded best and showed a change from baseline in their average ADAS-cog score of +2.4 points, which compares favorably with a score of +8.6 points on average in comparable historical controls. In addition, the average CDR-BS score in the mild-to-moderate AD patients after 20 months total on the study medication showed +2.7 points on average. This compared favorably with the reported 12-month mean change of +2.2 in comparable patients.

Figure 2:
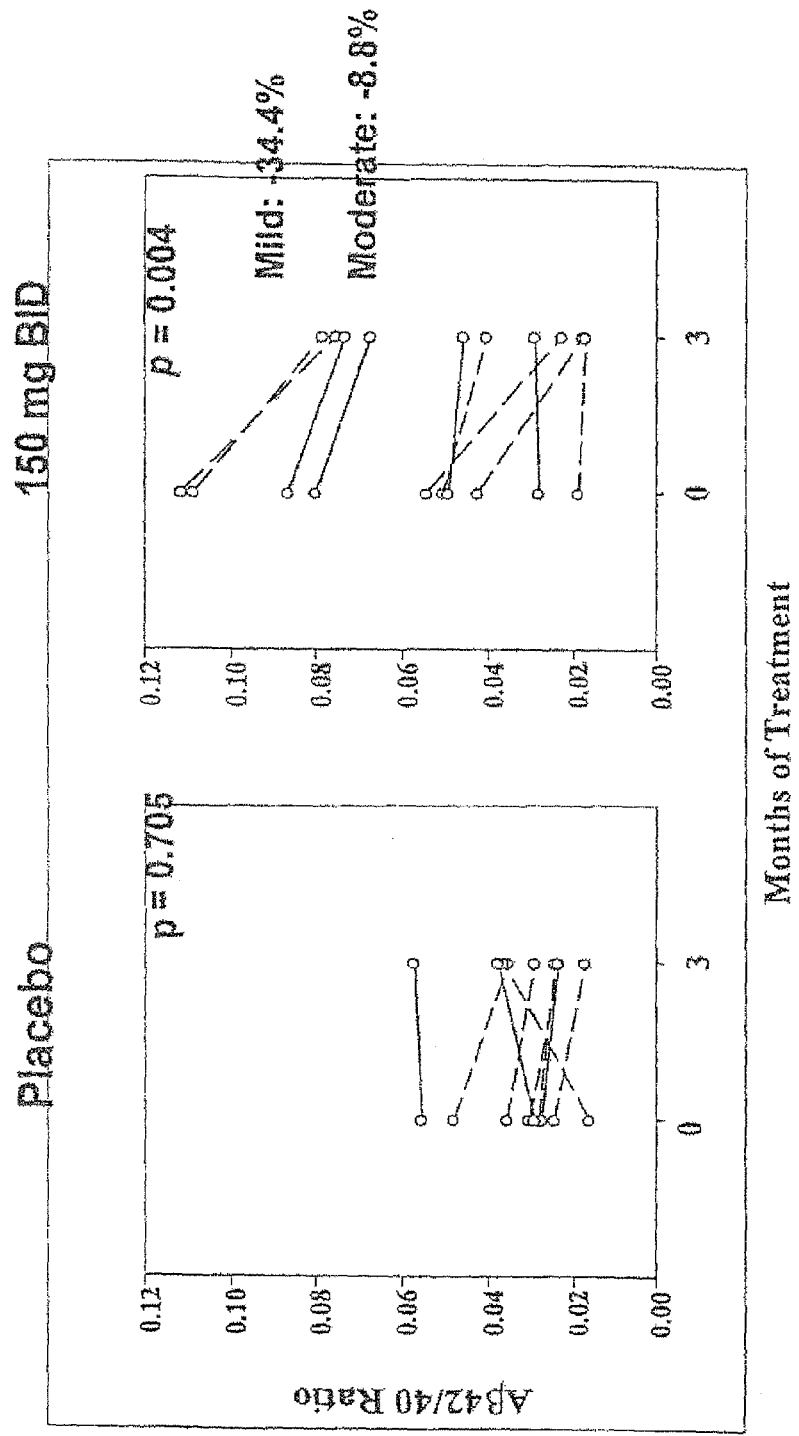
FIG. 2 Effect of 3-APS on CSF A$\beta_{42/40}$ Ratio in Mild-to-Moderate AD Patients—Placebo vs. 150 mg BID FIG. 3 Effect of 3-APS on CSF A$\beta_{42/40}$ Ratio in Mild-to-Moderate AD Patients 0 and 50 mg 3-APS FIG. 4 Effect of 3-APS on CSF A$\beta_{42/40}$ Ratio in Mild-to-Moderate AD Patients 100 and 150 mg 3-APS
Figure 3:
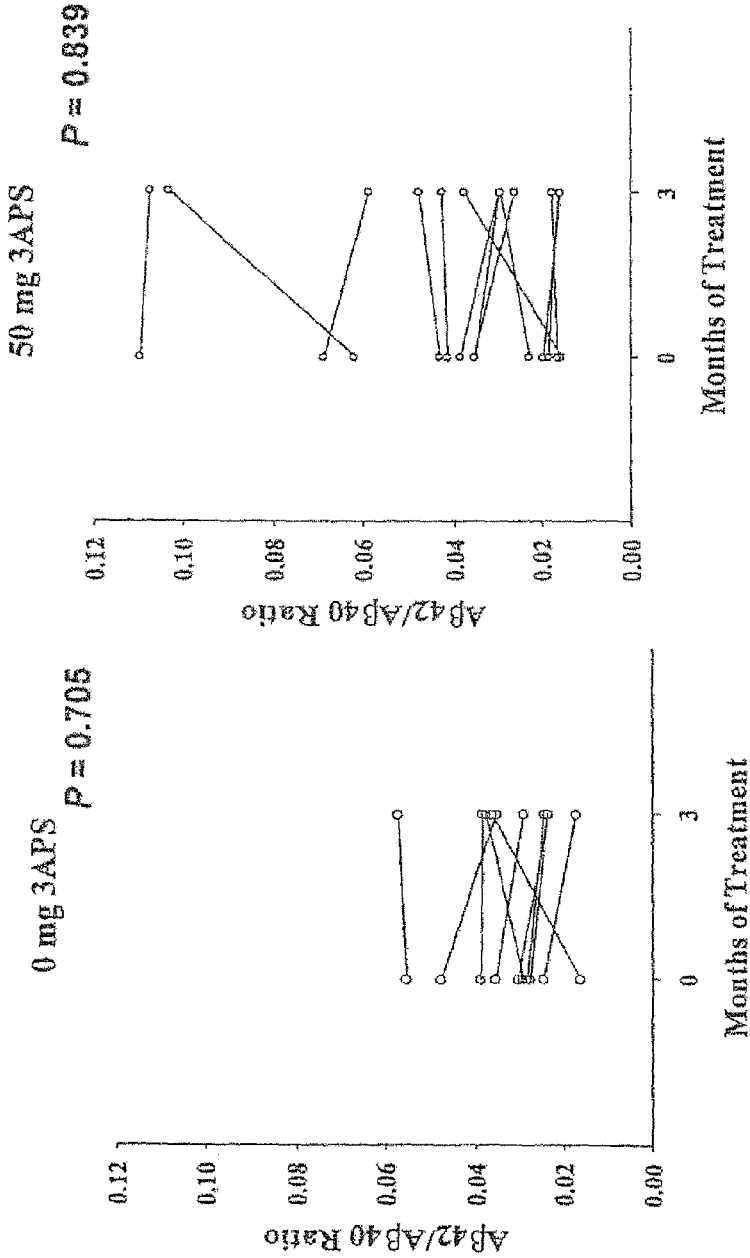

In additional tests, it was observed that the drug crossed the blood/brain barrier, reduced baseline CSF $A\beta_{42}$ (see FIG. 1), and reduced the ratio of $A\beta_{42}/A\beta_{40}$ (see FIGS. 2, 3 and 4).

We claim:

1. An oral formulation comprising an effective amount of 3-amino-1-propanesulfonic acid to treat amyloidosis, inhibit amyloid deposition and/or treat an amyloid deposition-related disease, a pharmaceutically acceptable vehicle and an enteric coating, wherein the formulation results in lesser gastrointestinal intolerance in comparison to an immediate release dosage form comprising 3-amino-1-propanesulfonic acid.

2. An oral formulation comprising an effective amount of 3-amino-1-propanesulfonic acid, a pharmaceutically acceptable vehicle and an enteric coating,
wherein the formulation results in lesser gastrointestinal intolerance in comparison to an immediate release dosage form comprising 3-amino-1-propanesulfonic acid.

3. A formulation of claim 2 wherein the amount of 3-amino-1-propanesulfonic acid is effective for stabilizing cognitive function or decreasing the rate of decline in cognitive function.

4. A formulation of claim 2 wherein the amount of 3-amino-1-propanesulfonic acid is effective for inhibiting neurodegeneration or cellular toxicity induced by amyloid-β.

5. An oral formulation comprising 3-amino-1-propanesulfonic acid, a pharmaceutical acceptable carrier and an enteric coating wherein the formulation results in lesser gastrointestinal intolerance in comparison to an immediate release dosage form comprising 3-amino-1-propane sulfonic acid.

6. The formulation of claim 5 wherein 20% or less dissolution of 3-amino-1-propanesulfonic acid occurs in the acidic environment of the stomach but dissolution occurs in the more neutral or alkaline environments of the GI tract.

7. The formulation of claim 5 wherein less than or equal to 10% dissolution of the active ingredient occurs within 2 hours.

8. A method for stabilizing cognitive function or decreasing the rate of decline in cognitive function in a subject in need thereof comprising administering a formulation of claim 3.

9. A method for inhibiting neurodegeneration or cellular toxicity induced by amyloid in a subject in need thereof comprising administering a formulation of claim 4.

10. The method of claim 9 wherein said amyloid is amyloid-β.

11. A method for treating amyloidosis in a subject in need thereof comprising administering a formulation of claim 4.

12. A method for inhibiting amyloid deposition in a subject in need thereof comprising administering a formulation of claim 4.

13. A method for treating an amyloid-related diseases or conditions in a subject in need thereof comprising administering a formulation of claim 4.

14. The method of claim 13 wherein said amyloid-related disease or condition is an amyloid-β-related disease or condition.

15. The method of claim 8 wherein said subject is an elderly individual.

16. The method of claim 14 wherein said amyloid-related disease or condition is selected from Alzheimer's disease, cerebral amyloid angiopathy, Down's syndrome, and mild cognitive impairment.

17. The method of claim 14 wherein said amyloid-related disease or condition is Alzheimer's disease or mild cognitive impairment.

18. A method for treating an amyloid-related disease in a human with brain amyloidosis comprising administering to the subject a therapeutic amount of a formulation of claim 3, such that cognitive function is improved or stabilized or further deterioration in cognitive function is slowed.

\* \* \* \* \*

UNITED STATES PATENT AND TRADEMARK OFFICE
CERTIFICATE OF CORRECTION

PATENT NO.        : 8,835,500 B2
APPLICATION NO.   : 12/362971
DATED             : September 16, 2014
INVENTOR(S)       : Denis Garceau et al.

It is certified that error appears in the above-identified patent and that said Letters Patent is hereby corrected as shown below:

On the Title Page

Item (12): Delete "Laurin" and insert --Garceau--

Item (75) Inventors:   Delete "Julie Laurin, St-Lazare (CA)."
                       After Denis Garceau, Kirkland (CA) insert
                       --Audley Legore, Laval (CA)--

Signed and Sealed this
Second Day of December, 2014

Michelle K. Lee
*Deputy Director of the United States Patent and Trademark Office*